United States Patent [19]
Sagane et al.

[11] Patent Number: 5,837,791
[45] Date of Patent: Nov. 17, 1998

[54] UNSATURATED COPOLYMER OF ETHYLENE AND PROCESS FOR PREPARING THE SAME

[75] Inventors: Toshihiro Sagane, Tokyo; Masaaki Kawasaki; Hidenari Nakahama, both of Ichihara; Tatsuyoshi Ishida, Kuga-gun; Katsuya Takahashi, Ichihara; Toshiyuki Tsutsui, Kuga-gun; Hitoshi Onishi, Kuga-gun; Masaaki Yasuda, Kuga-gun; Noriaki Kihara, Kuga-gun, all of Japan

[73] Assignee: Mitsui Petrochemical Industries, Ltd., Tokyo, Japan

[21] Appl. No.: 915,914

[22] Filed: Aug. 21, 1997

Related U.S. Application Data

[63] Continuation of Ser. No. 499,553, Jul. 6, 1995, abandoned.

[30] Foreign Application Priority Data

| Jul. 6, 1994 | [JP] | Japan | 6-154952 |
| Jul. 14, 1994 | [JP] | Japan | 6-162475 |
| Mar. 28, 1995 | [JP] | Japan | 7-069986 |
| Mar. 31, 1995 | [JP] | Japan | 7-075289 |

[51] Int. Cl.$^6$ ............................................. G08F 236/20
[52] U.S. Cl. .................... 526/336; 526/337; 526/339; 526/348.2; 526/348.3
[58] Field of Search ......................... 526/336, 339, 526/337

[56] References Cited

U.S. PATENT DOCUMENTS

| 3,480,599 | 11/1969 | Parr ........................................... 526/336 |
| 3,846,387 | 11/1974 | Su . |
| 3,887,531 | 6/1975 | Schneider et al. . |
| 3,900,452 | 8/1975 | Valvasseri et al. . |

FOREIGN PATENT DOCUMENTS

| 0219166 | 4/1987 | European Pat. Off. . |
| 2179772 | 11/1973 | France . |
| 2-051512 | 2/1990 | Japan . |
| 6-128427 | 5/1994 | Japan . |
| 6-179722 | 6/1994 | Japan . |
| 6-179723 | 6/1994 | Japan . |
| 1090124 | 11/1967 | United Kingdom . |

*Primary Examiner*—Fred Zitomer
*Attorney, Agent, or Firm*—Sherman and Shalloway

[57] ABSTRACT

A novel unsaturated copolymer of ethylene comprises a random copolymer of (i) ethylene, (ii) an α-olefin of 3 to 20 carbon atoms and (iii) at least one straight chain or branched chain nonconjugated triene or tetraene having one vinyl group in the molecule, which contains 30–92% by mol of ethylene units (i), 6–70% by mol of α-olefin units (ii) and 0.1–30% by mol of triene or tetraene units (iii), and which has a molar ratio of ethylene units (i) to α-olefin units (ii) of 40/60 to 92/8 (ethylene units (i)/α-olefin units (ii)) and an intrinsic viscosity (η), measured in Decalin at 135° C., of 0.05 to 10 dl/g. This novel unsaturated copolymer of ethylene is excellent in weathering resistance, heat resistance and ozone resistance and has a high vulcanizing rate.

13 Claims, No Drawings

UNSATURATED COPOLYMER OF ETHYLENE AND PROCESS FOR PREPARING THE SAME

This application is a continuation, division of application Ser. No. 08/499,553, filed Jul. 6, 1995, now abandoned.

FIELD OF THE INVENTION

The present invention relates to an unsaturated copolymer of ethylene and a process for preparing said copolymer. More particularly, the invention relates to a novel unsaturated copolymer of ethylene excellent in weathering resistance, heat resistance and ozone resistance and having a high vulcanizing rate, and to a process for preparing said copolymer.

BACKGROUND OF THE INVENTION

Unsaturated copolymers of ethylene are vulcanizable polymers, and because of their excellent weathering resistance, heat resistance and ozone resistance, they have been used for various rubber products, for example, automotive industrial parts, industrial rubber products, electrical insulating materials, civil engineering materials, building materials and rubberized fabrics. Further, they have been widely used as blending materials for plastics such as polypropylene and polystyrene.

Conventionally known unsaturated copolymers of ethylene include an ethylene-propylene-5-ethylidene-2-norbornene copolymer, an ethylene-propylene-dicyclopentadiene copolymer and an ethylene-propylene-1,4-hexadiene copolymer. Of these, the ethylene-propylene-5-ethylidene- 2-norbornene copolymer is particularly widely used, because it has a higher vulcanizing rate as compared with other unsaturated copolymers of ethylene.

However, these conventional unsaturated copolymers of ethylene are now desired to be further improved in the vulcanizing rate. That is, the unsaturated copolymers of ethylene, for example, even the ethylene-propylene-5-ethylidene-2-norbornene copolymer, are lower in the vulcanizing rate as compared with diene type rubbers such as natural rubber, styrene-butadiene rubber, isoprene rubber, butadiene rubber and nitrile rubber. Therefore, the covulcanizability of the unsaturated copolymer of ethylene and the diene type rubber is insufficient.

The unsaturated copolymers of ethylene are low in the vulcanizing rate, so that it is difficult to prepare vulcanized rubbers therefrom with high productivity by shortening the vulcanizing time, lowering the vulcanizing temperature or reducing the consumption of energy in the vulcanization stage.

The vulcanizing rate of the unsaturated copolymers of ethylene can be increased by increasing the amount of a vulcanizing agent used. However, if the unsaturated copolymers of ethylene are vulcanized using a large amount of a vulcanizing agent, blooming of the vulcanizing agent onto the surfaces of the resulting vulcanized rubbers sometimes takes place so that it is unfavorable from the appearance viewpoint, and further, there is a possibility of pollution by the blooming in the use of the vulcanized rubbers.

Accordingly, the advent of an unsaturated copolymer of ethylene excellent in weathering resistance, heat resistance and ozone resistance and having a high vulcanizing rate has been desired.

The present inventors have earnestly studied on the unsaturated ethylene copolymers and have found that an unsaturated copolymer of ethylene having constituent units derived from ethylene, an α-olefin and a specific straight or branched chain polyene and containing unsaturated bonds is excellent in weathering resistance, heat resistance and ozone resistance and has a high vulcanizing rate. Based on this finding, the present inventors have accomplished the present invention.

OBJECT OF THE INVENTION

The present invention is intended to solve the problems associated with the prior art technique as described above, and it is an object of the invention to provide an unsaturated copolymer of ethylene which is excellent in weathering resistance, heat resistance and ozone resistance and which has a high vulcanizing rate and to provide a process for preparing said copolymer.

SUMMARY OF THE INVENTION

The unsaturated copolymer of ethylene according to the present invention is characterized in that:

(A) said copolymer is a random copolymer of:
(i) ethylene,
(ii) an α-olefin of 3 to 20 carbon atoms, and
(iii) at least one straight chain or branched chain nonconjugated triene or tetraene having one vinyl group in the molecule;

(B) said copolymer comprises:
(i) constituent units from ethylene in amounts of 30 to 92% by mol,
(ii) constituent units from the α-olefin of 3 to 20 carbon atoms in amounts of 6 to 70% by mol,
(iii) constituent units from the nonconjugated triene or tetraene in amounts of 0.1 to 30% by mol, in which
(iv) a molar ratio of the constituent units derived from ethylene (i) to the constituent units derived from the α-olefin of 3 to 20 carbon atoms (ii) is in the range of 40/60 to 92/8; and (C) said copolymer has an intrinsic viscosity (η), as measured in Decalin (decahydronaphthalene—E.I. Du Pont de Nemours & Co.) at 135° C., of 0.05 to 10 dl/g.

In one preferred embodiment of the unsaturated copolymer of ethylene according to the invention, the nonconjugated triene or tetraene (iii) in (A) is a nonconjugated triene or tetraene in which one straight chain or branched chain hydrocarbon group and two hydrogen atoms are bonded to the carbon atom adjacent to the vinyl group.

In a particularly preferred embodiment of the unsaturated copolymer of ethylene according to the invention, the nonconjugated triene or tetraene (iii) in (A) is represented by the following formula (H-1), and the constituent units from the nonconjugated triene or tetraene (iii) in (B) are represented by the following formula (H-2):

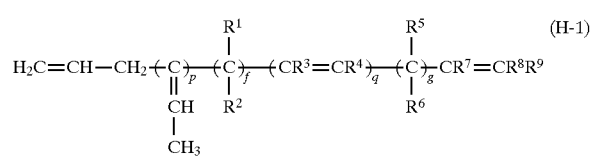

wherein p and q are each 0 or 1, with the proviso that each of p and q is not 0 at the same time; f is an integer of 0 to 5, with the proviso that when p and q are each 1, f is not 0; g is an integer of 1 to 6; $R^1$, $R^2$, $R^3$, $R^4$, $R^5$, $R^6$ and $R^7$ are each hydrogen or an alkyl group of 1 to 5 carbon atoms; $R^8$ is an alkyl group of 1 to 5 carbon atoms; and $R^9$ is hydrogen, an alkyl group of 1 to 5 carbon atoms or a group represented by the formula $-(CH_2)_n-CR^{10}=CR^{11}R^{12}$, where n is an integer of 1 to 5, $R^{10}$ and $R^{10}$ are each hydrogen or an alkyl group of 1 to 5 carbon atoms, and $R^{12}$ is an alkyl group of 1 to 5 carbon atoms, with the proviso that when p and q are each 1, $R^9$ is hydrogen or an alkyl group of 1 to 5 carbon atoms;

$$-\!\!\left(CH_2-CH\right)\!\!- \quad CH_2\!\!-\!\!\left(\underset{\underset{CH_3}{\overset{\overset{CH}{\|}}{C}}}{C}\right)_{\!p}\!\!-\!\!\left(\underset{R^2}{\overset{R^1}{C}}\right)_{\!f}\!\!-\!\!(CR^3\!=\!CR^4)_{\!q}\!\!-\!\!\left(\underset{R^6}{\overset{R^5}{C}}\right)_{\!g}\!\!-\!CR^7\!=\!CR^8R^9 \qquad (H\text{-}2)$$

wherein p, q, f, g and $R^1$ to $R^9$ have the same meanings as described in the formula (H-1).

In another preferred embodiment of the unsaturated copolymer of ethylene according to the invention, the nonconjugated triene or tetraene (iii) in (A) is represented by the following formula (Ia), and the constituent units from the nonconjugated triene or tetraene (iii) in (B) are represented by the following formula (IIa):

$$H_2C\!=\!CH\!-\!CH_2\!-\!\!\left(\underset{R^2}{\overset{R^1}{\underset{|}{\overset{|}{C}}}}\right)_{\!f}\!\!-\!CR^3\!=\!CR^4\!-\!\!\left(\underset{R^6}{\overset{R^5}{\underset{|}{\overset{|}{C}}}}\right)_{\!g}\!\!-\!CR^7\!=\!CR^8R^9 \qquad (Ia)$$

wherein f is an integer of 0 to 5; g is an integer of 1 to 6; $R^1$, $R^2$, $R^3$, $R^4$, $R^5$, $R^6$ and $R^7$ are each hydrogen or an alkyl group of 1 to 5 carbon atoms; this an alkyl group of 1 to 5 carbon atoms; and $R^9$ is hydrogen, an alkyl group of 1 to 5 carbon atoms or a group represented by the formula $-(CH_2)_n-CR^{10}=CR^{11}R^{12}$ where n is an integer of 1 to 5, $R^{10}$ and $R^{11}$ are each hydrogen or an alkyl group of 1 to 5 carbon atoms, and $R^{12}$ is an alkyl group of 1 to 5 carbon atoms;

$$-\!\!\left(H_2C\!-\!CH\right)\!\!- \quad CH_2\!\!-\!\!\left(\underset{R^2}{\overset{R^1}{\underset{|}{\overset{|}{C}}}}\right)_{\!f}\!\!-\!CR^3\!=\!CR^4\!-\!\!\left(\underset{R^6}{\overset{R^5}{\underset{|}{\overset{|}{C}}}}\right)_{\!g}\!\!-\!CR^7\!=\!CR^8R^9 \qquad (IIa)$$

wherein f, g and $R^1$ to $R^9$ have the same meanings as described in the formula (Ia).

Of these, preferred are the compounds of the formulas (Ia) and (IIa) wherein $R^1$, $R^2$, $R^5$ and $R^6$ are each hydrogen.

In another preferred embodiment of the unsaturated copolymer of ethylene according to the invention, the nonconjugated triene or tetraene (iii) in (A) is represented by the following formula (Ib), and the constituent units from the nonconjugated triene or tetraene (iii) in (B) are represented by the following formula (IIb):

$$H_2C\!=\!CH\!-\!CH_2\!-\!\underset{CH(CH_3)}{\overset{\overset{\|}{C}}{C}}\!-\!(CR^1R^2)_f\!-\!(CR^5R^6)_g\!-\!CR^7\!=\!CR^8R^9 \qquad (Ib)$$

wherein f is an integer of 0 to 6; g is an integer of 1 to 5; $R^1$, $R^2$, $R^5$, $R^6$ and $R^7$ are each hydrogen or an alkyl group of 1 to 5 carbon atoms; $R^8$ is an alkyl group of 1 to 5 carbon atoms; and $R^9$ is hydrogen, an alkyl group of 1 to 5 carbon atoms or a group represented by the formula $-(CH_2)_n-CR^{10}=CR^{11}R^{12}$, where n is an integer of 1 to 5, $R^{10}$ and $R^{11}$ are each hydrogen or an alkyl group of 1 to 5 carbon atoms, and $R^{12}$ is an alkyl group of 1 to 5 carbon atoms;

$$-\!\!\left(H_2C\!-\!CH\right)\!\!- \quad CH_2\!-\!\underset{CH(CH_3)}{\overset{\overset{\|}{C}}{C}}\!-\!(CR^1R^2)_f\!-\!(CR^5R^6)_g\!-\!CR^7\!=\!CR^8R^9 \qquad (IIb)$$

wherein f, g, $R^1$, $R^2$ and $R^5$ to $R^9$ have the same meanings as described in the formula (Ib).

More preferably, the nonconjugated tetraene (iii) in (A) is represented by the following formula (Ib'), and the constituent units from the nonconjugated tetraene (iii) in (B) are represented by the following formula (IIb'):

$$H_2C\!=\!CH\!-\!CH_2\!\!-\!\!\left(\underset{\underset{CH_3}{\overset{\overset{CH}{\|}}{C}}}{C}\right)\!\!-\!\!\left(\underset{R^2}{\overset{R^1}{C}}\right)_{\!f}\!\!-\!\!\left(\underset{R^6}{\overset{R^5}{C}}\right)_{\!g}\!\!-\!\!\overset{R^7}{\underset{|}{C}}\!=\!\overset{R^8}{\underset{|}{C}}\!-\!(CH_2)_n\!-\!\overset{R^{10}}{\underset{|}{C}}\!=\!CR^{11}R^{12} \qquad (Ib')$$

wherein f is an integer of 0 to 5; g is an integer of 1 to 6; $R^1$, $R^2$, $R^5$, $R^6$ and $R^7$ are each hydrogen or an alkyl group of 1 to 5 carbon atoms; $R^8$ is an alkyl group of 1 to 5 carbon atoms; n is an integer of 1 to 5; $R^{10}$ and $R^{11}$ are each hydrogen or an alkyl group of 1 to 5 carbon atoms; and $R^{12}$ is an alkyl group of 1 to 5 carbon atoms;

$$-\!\!\left(H_2C\!-\!CH\right)\!\!- \quad CH_2\!\!-\!\!\left(\underset{\underset{CH_3}{\overset{\overset{CH}{\|}}{C}}}{C}\right)\!\!-\!\!\left(\underset{R^2}{\overset{R^1}{C}}\right)_{\!f}\!\!-\!\!\left(\underset{R^6}{\overset{R^5}{C}}\right)_{\!g}\!\!-\!\!\overset{R^7}{\underset{|}{C}}\!=\!\overset{R^8}{\underset{|}{C}}\!-\!(CH_2)_n\!-\!\overset{R^{10}}{\underset{|}{C}}\!=\!CR^{11}R^{12} \qquad (IIb')$$

wherein f, g and $R^1$, $R^2$, $R^5$ to $R^8$, n and $R^{10}$ to $R^{12}$ have the same meanings as described in the formula (Ib').

In a still further preferred embodiment of the unsaturated copolymer according to the invention, $R^1$, $R^2$, $R^5$ and $R^6$ in the formulas (Ib), (Ib'), (IIb) and (IIb') are each hydrogen.

Of these, preferred is the nonconjugated triene represented by the following formula (Ic), and the constituent units from the nonconjugated triene represented by the following formula (IIc);

$$H_2C\!=\!CH\!-\!CH_2\!-\!\underset{CH(CH_3)}{\overset{\overset{\|}{C}}{C}}\!-\!(CR^1R^2)_f\!-\!(CR^5R^6)_g\!-\!CR^7\!=\!CR^8R^9 \qquad (Ic)$$

wherein f is an integer of 0 to 5; g is an integer of 1 to 6; $R^1$, $R^2$, $R^5$, $R^6$ and $R^7$ are each hydrogen or an alkyl group of 1 to 5 carbon atoms; $R^8$ is an alkyl group of 1 to 5 carbon atoms; and $R^9$ is hydrogen or an alkyl group of 1 to 5 carbon atoms;

$$-\!\!\left(H_2C\!-\!CH\right)\!\!- \quad CH_2\!-\!\underset{CH(CH_3)}{\overset{\overset{\|}{C}}{C}}\!-\!(CR^1R^2)_f\!-\!(CR^5R^6)_g\!-\!CR^7\!=\!CR^8R^9 \qquad (IIc)$$

wherein f, g, $R^1$, $R^2$ and $R^5$ to $R^9$ have the same meanings as described in the formula (Ic).

In a still further preferred embodiment of the unsaturated copolymer of ethylene according to the invention, $R^1$, $R^2$, $R^5$ and $R^6$ in the formulas (Ic) and (IIc) are each hydrogen.

In a still further preferred embodiment of the unsaturated ethylene copolymer according to the invention, the total number of the hydrogen atoms directly bonded to the carbon atoms adjacent to all the carbon-to-carbon double bonds in the nonconjugated triene or tetraene (iii) in (A) is 9 to 33, preferably 12 to 33, more preferably 14 to 33.

The process for preparing an unsaturated copolymer of ethylene according to the present invention comprises copolymerizing:

(i) ethylene,
(ii) an α-olefin of 3 to 20 carbon atoms, and
(iii) at least one straight chain or branched chain nonconjugated triene or tetraene having one vinyl group in the molecule;

in the presence of a catalyst formed from a transition metal compound, and an organoaluminum compound and/or an ionized ionic compound, to obtain an unsaturated copolymer of ethylene characterized in that:

(A) said copolymer is a random copolymer of:
  (i) ethylene,
  (ii) an α-olefin of 3 to 20 carbon atoms, and
  (iii) at least one straight chain or branched chain nonconjugated triene or tetraene having one vinyl group in the molecule;
(B) said copolymer comprises:
  (i) constituent units from ethylene in amounts of 30 to 92% by mol,
  (ii) constituent units from the α-olefin of 3 to 20 carbon atoms in amounts of 6 to 70% by mol,
  (iii) constituent units from the nonconjugated triene or tetraene in amounts of 0.1 to 30% by mol, in which
  (iv) a molar ratio of the constituent units from ethylene (i) to the constituent units from the α-olefin of 3 to 20 carbon atoms (ii) is in the range of 40/60 to 92/8; and
(C) said copolymer has an intrinsic viscosity (η), as measured in Decalin at 135° C., of 0.05 to 10 dl/g.

In a preferred embodiment of the process for preparing an unsaturated copolymer of ethylene according to the invention, the nonconjugated triene or tetraene (iii) in (A) is a nonconjugated triene or tetraene in which one straight chain or branched chain hydrocarbon group other than vinyl group and two hydrogen atoms are bonded to the carbon atom adjacent to the vinyl group, and the constituent units derived from the nonconjugated triene or tetraene (iii) in (B) are constituent units in which one straight chain or branched chain hydrocarbon group and two hydrogen atoms are bonded to a carbon atom adjacent to a carbon atom contained in the main chain of the copolymer.

In a more preferred embodiment of the process for preparing an unsaturated copolymer of ethylene according to the invention, the nonconjugated triene or tetraene (iii) in (A) is represented by the above formula (H-1), and the constituent units from the nonconjugated triene or tetraene (iii) in (B) are represented by the above formula (H-2).

In one of more preferred embodiments of the process for preparing an unsaturated copolymer of ethylene according to the invention, the nonconjugated triene or tetraene (iii) in (A) is represented by the above formula (Ia), and the constituent units from the nonconjugated triene or tetraene (iii) in (B) are represented by the above formula (IIa), and desirably $R^1$, $R^2$, $R^5$ and $R^6$ in the formulas (Ia) and (IIa) are each hydrogen.

In another more preferred embodiment of the process for preparing an unsaturated copolymer of ethylene according to the invention, the nonconjugated triene or tetraene (iii) in (A) is represented by the above formula (Ib), and the constituent units from the nonconjugated triene or tetraene (iii) in (B) are represented by the above formula (IIb), preferably the nonconjugated tetraene (iii) in (A) is represented by the above-formula (Ib'), and the constituent units from the nonconjugated tetraene (iii) in (B) are represented by the above formula (IIb'), and particularly $R^1$, $R^2$, $R^5$ and $R^6$ in the formulas (Ib), (IIb), (Ib') and (IIb') are each hydrogen.

In a still further preferred embodiment of the process for preparing an unsaturated copolymer of ethylene according to the invention, the nonconjugated triene or tetraene (iii) in (A) is represented by the above formula (Ic), and the constituent units from the nonconjugated triene or tetraene (iii) in (B) are represented by the above formula (IIc), and desirably $R^1$, $R^2$, $R^5$ and $R^6$ in the formulas (Ic) and (IIc) are each hydrogen.

In a still further preferred embodiment of the process for preparing an unsaturated copolymer of ethylene according to the invention, the total number of the hydrogen atoms directly bonded to the carbon atoms adjacent to all of the carbon-to-carbon double bonds in the nonconjugated triene or tetraene (iii) in (A) is 9 to 33, preferably 12 to 33, more preferably 14 to 33.

The rubber composition according to the present invention comprises:

the unsaturated copolymer of ethylene as described above, and
at least one component selected from the following agents (a), (b) and (c):
(a) a reinforcing agent in an amount of not more than 300 parts by weight based on 100 parts by weight of the unsaturated ethylene copolymer,
(b) a softening agent in an amount of not more than 200 parts by weight based on 100 parts by weight of the unsaturated ethylene copolymer, and
(c) a vulcanizing agent.

The rubber composition according to the invention is excellent in weathering resistance, heat resistance and ozone resistance, and has a high vulcanizing rate.

DETAILED DESCRIPTION OF THE INVENTION

The unsaturated copolymer of ethylene and the process for preparing said copolymer according to the invention will be described in detail hereinafter.

Unsaturated copolymer of ethylene

The unsaturated copolymer according to the invention is (A) a random copolymer of:
(i) ethylene,
(ii) an α-olefin of 3 to 20 carbon atoms, and
(iii) at least one straight chain or branched chain nonconjugated triene or tetraene having one vinyl group in the molecule (triene and tetraene are sometimes referred to as "polyene").

Examples of the α-olefins (ii) of 3 to 20 carbon atoms include propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene and 1-eicosene. Of these, preferred are propylene, 1-butene, 1-hexene and 1-octene. These α-olefins may be used singly or in combination of two or more kinds.

In the present invention, the nonconjugated triene or tetraene (iii) in (A) is a hydrocarbon compound. The total number of carbon atoms of the hydrocarbon compound (in case of two or more compounds, an average of carbon atoms thereof) is not specifically limited, but it is preferably 9 to 30, more preferably 10 to 25, particularly preferably 10 to 22. These compounds having the total number of carbon atoms within the above range have advantages, e.g., good handleability due to their ease of purification. The term "triene" means a compound (hydrocarbon compound) having three carbon-to-carbon double bonds (C=C), and the term "tetraene" means a compound (hydrocarbon compound) having four carbon-to-carbon double bonds. The carbon-to-carbon double bonds include the carbon-to-carbon double bond of the vinyl group ($CH_2$=CH—)

The nonconjugated triene or tetraene (iii) in (A) has one vinyl group ($CH_2$=CH—) in the molecule.

The nonconjugated triene or tetraene (iii) in (A) has three (in the case of triene) or four (in the case of tetraene) carbon-to-carbon double bonds (C=C), inclusive of the vinyl group. There is no specific limitation on the total number of the hydrogen atoms directly bonded to the carbon atoms adjacent to all the carbon-to-carbon double bonds contained in the molecule of the nonconjugated triene or tetraene (iii), but it is preferably 9 to 33, more preferably 12 to 33, particularly preferably 14 to 33. These compounds having the total number of hydrogen atoms within the above range are preferred from the view point of obtaining copolymers having a high vulcanization rate.

In the invention, preferred is a nonconjugated triene or tetraene in which a methylene group (—$CH_2$—) is bonded to the vinyl group. When two or more of the nonconjugated trienes or tetraenes are used, the number of hydrogen atoms is expressed by an average of the hydrogen atoms thereof.

The number of hydrogen atoms is now described in more detail.

For example, in the following compound, the carbon-to-carbon double bonds are present at the positions of 1–2 carbons (of vinyl group), 4–5 carbons, 12–14 carbons and 16–17 carbons, and the carbons adjacent to the carbon-to-carbon double bonds are those of 3, 6, 7, 11, 13, 15 and 18 (carbons of 8, 9, 10 and 19 are not included). Therefore, the total number of the hydrogen atoms bonded to the carbon atoms adjacent to the carbon-to-carbon double bonds amounts to 16 (2 (carbon 3)+3 (carbon 6)+2 (carbon 7)+2 (carbon 11)+3 (carbon 13)+2 (carbon 15)+2 (carbon 18)= 16).

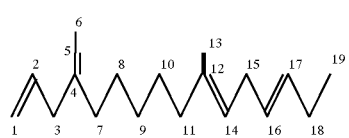

In the following compound (5-ethylidene-2-norbornene) which is used in the Comparative Examples described later, the carbon-to-carbon double bonds are present at the positions of 2–3 carbons and 5–8 carbons, and the carbons adjacent to the carbon-to-carbon double bonds are those of 1, 4, 6 and 9 (carbon 7 is not included). Therefore, the total number of the hydrogen atoms bonded to the carbon atoms adjacent to the carbon-to-carbon double bonds amounts to 7 [1 (carbon 1)+1 (carbon 4)+2 (carbon 6)+3 (carbon 9)=7].

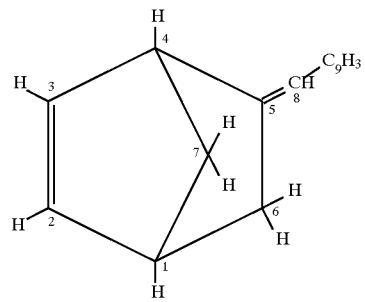

In the present invention, at least one straight chain or branched chain nonconjugated triene or tetraene may be used.

The nonconjugated triene or tetraene (iii) is preferably represented by the following formula (H-1):

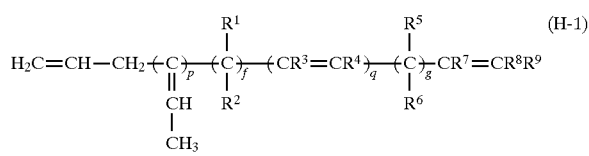

wherein p and q are each 0 or 1, with the proviso that each of p and q is not 0 at the same time; f is an integer of 0 to 5, with the proviso that when p and q are each 1, f is not 0; g is an integer of 1 to 6; $R^1$, $R^2$, $R^3$, $R^4$, $R^5$, $R^6$ and $R^7$ are each hydrogen or an alkyl group of 1 to 5 carbon atoms; $R^8$ is an alkyl group of 1 to 5 carbon atoms; and $R^9$ is hydrogen, an alkyl group of 1 to 5 carbon atoms or a group represented by the formula —$(CH_2)_n$—$CR^{10}$=$CR^{11}R^{12}$, where n is an integer of 1 to 5, $R^{10}$ and $R^{11}$ are each hydrogen or an alkyl group of 1 to 5 carbon atoms, and $R^{12}$ is an alkyl group of 1 to 5 carbon atoms, with the proviso that when p and q are each 1, $R^9$ is hydrogen or an alkyl group of 1 to 5 carbon atoms.

Of the nonconjugated trienes or tetraenes represented by the formula (H-1), preferred are the nonconjugated trienes or tetraenes represented by the formulas (Ia) and (Ib). Of the nonconjugated polyene (Ib), more preferred are the tetraene (Ib') and the triene (Ic).

Details of these preferred nonconjugated triene or tetraene (iii) are described below in order.

Nonconjugated triene or tetraene (Ia)

The preferred nonconjugated triene or tetraene (iii) among the above compounds (H-1) is a straight chain triene or tetraene (sometimes referred to as "straight chain polyene") represented by the following formula (Ia).

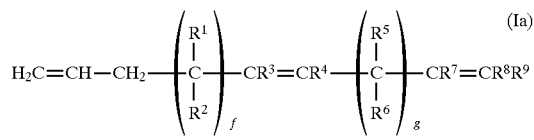

This nonconjugated triene or tetraene (Ia) is a nonconjugated triene or tetraene of the above formula (H-1) wherein p is 0; q is 1; f is an integer of 0 to 5; and g is an integer of 1 to 6; and $R^1$ to $R^9$ have the meanings as defined above.

Preferably, $R^1$, $R^2$, $R^3$, $R^4$, $R^5$ and $R^6$ are each hydrogen or an alkyl group of 1 to 5 carbon atoms, more preferably hydrogen or an alkyl group of 1 to 3 carbon atoms, particularly preferably $R^1$, $R^2$, $R^5$ and $R^6$ are each hydrogen.

Preferably, $R^7$ is hydrogen or an alkyl group of 1 to 5 carbon atoms, more preferably hydrogen or an alkyl group or 1 to 3 carbon atoms.

Preferably, $R^8$ is an alkyl group of 1 to 5 carbon atoms, more preferably an alkyl group of 1 to 3 carbon atoms.

Preferably, $R^9$ is hydrogen, an alkyl group of 1 to 5, preferably 1 to 3 carbon atoms, or a group represented by the formula $-(CH_2)_n-CR^{10}=CR^{11}R^{12}$, where n is an integer of 1 to 5, preferably 1 to 3; $R^{10}$ and $R^{10}$ are each hydrogen or an alkyl group of 1 to 5, preferably 1 to 3 carbon atoms; and $R^{12}$ is an alkyl group of 1 to 5, preferably 1 to 3 carbon atoms.

Examples of the alkyl groups of 1 to 5 carbon atoms in the formula (Ia) include methyl, ethyl, n-propyl, i-propyl, n-butyl, i-butyl, sec-butyl, t-butyl and pentyl.

Listed below are examples of the straight chain trienes or tetraenes (iii), and preferably used are 6,10-dimethyl-1,5,9-undecatriene (DMUT), 5,9-dimethyl-1,4,8-decatriene (DMDT) and the compounds (17), (26), (58) and (78).

6,10-Dimethyl-1,5,9-undecatriene (DMUT)

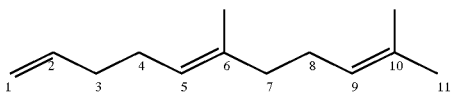

5,9-Dimethyl-1,4,8-decatriene (DMDT)

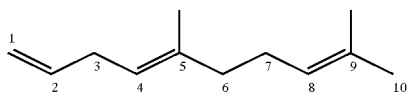

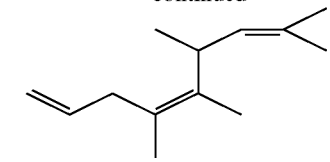
1

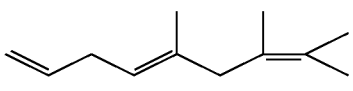
2

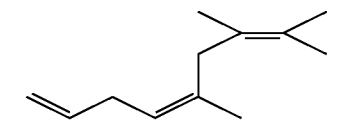
3

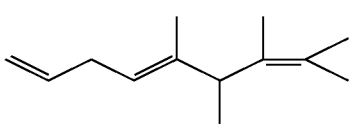
4

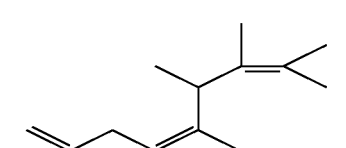
5

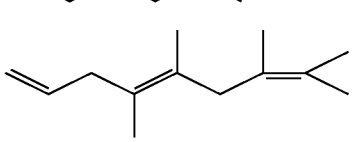
6

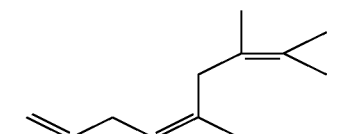
7

-continued

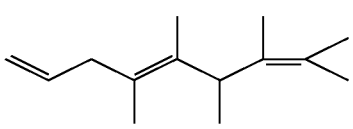
8
9
10
11

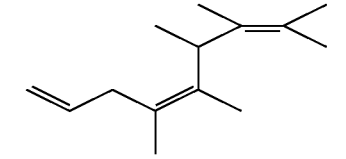
12
13
14
15

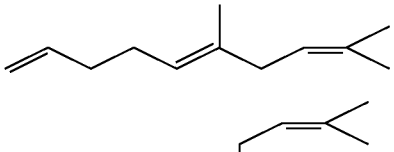
16
17

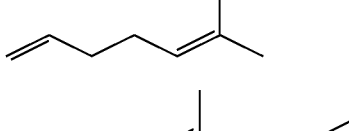
18

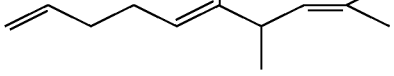
19

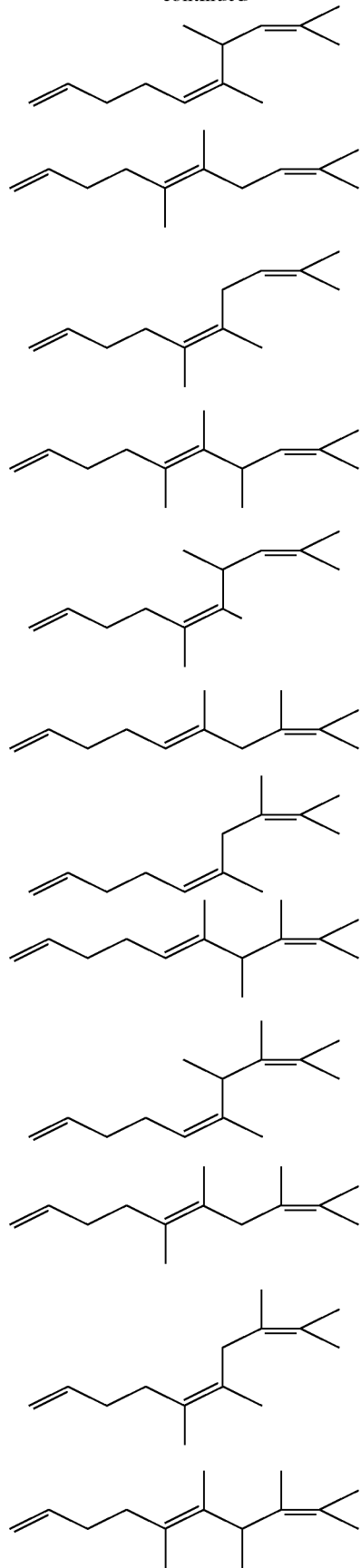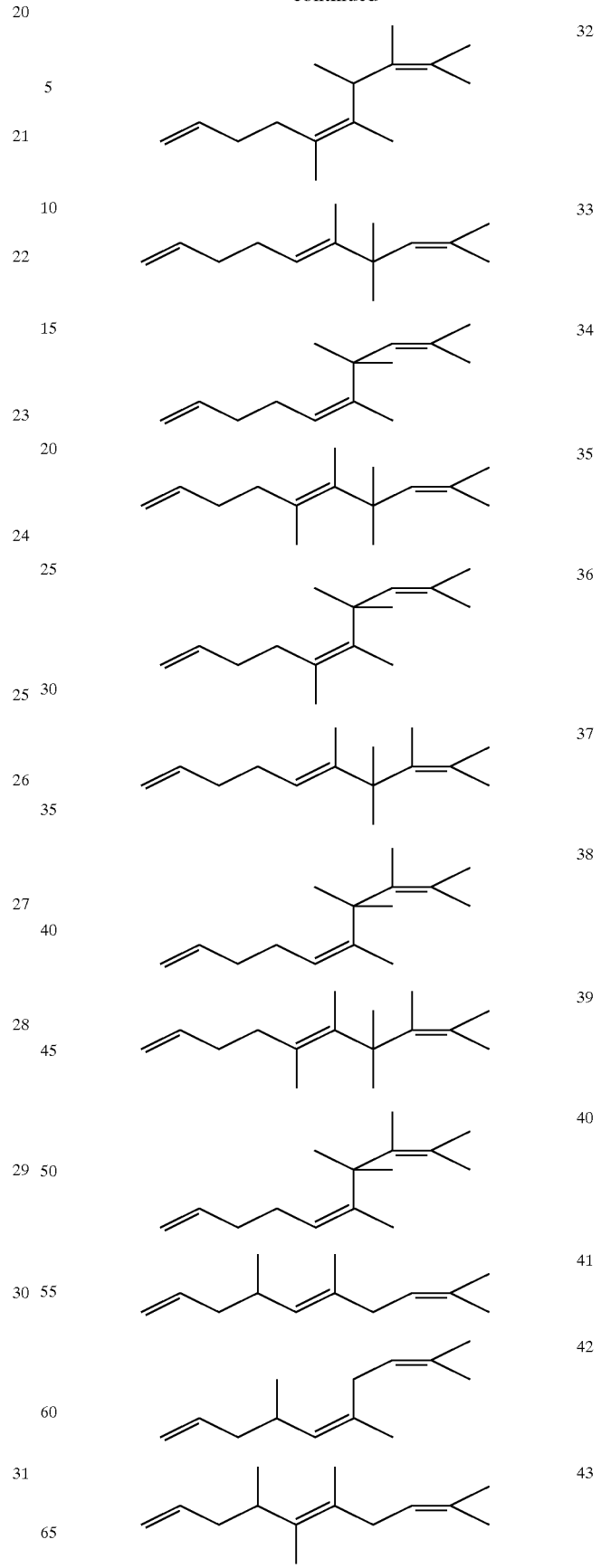

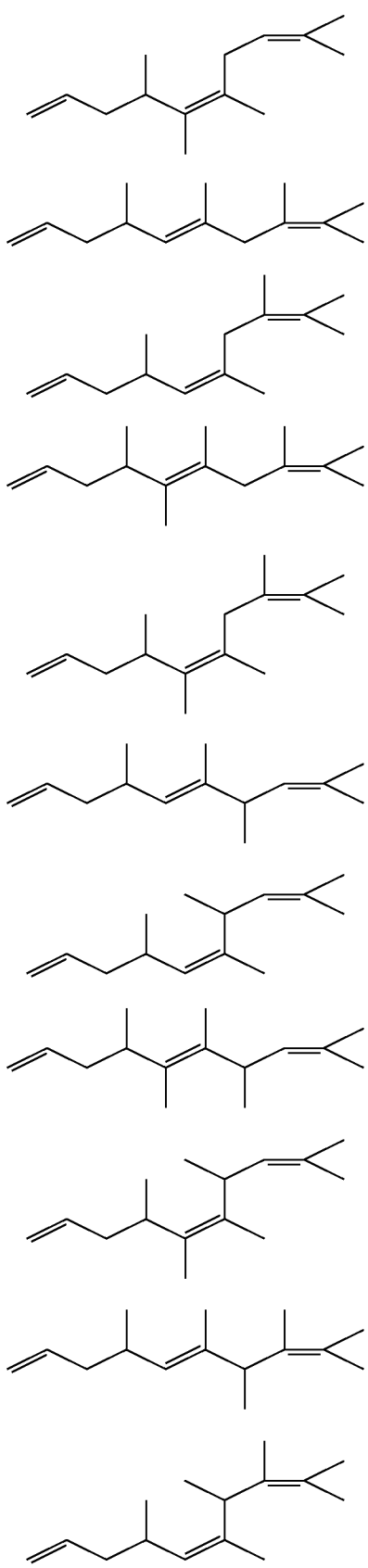
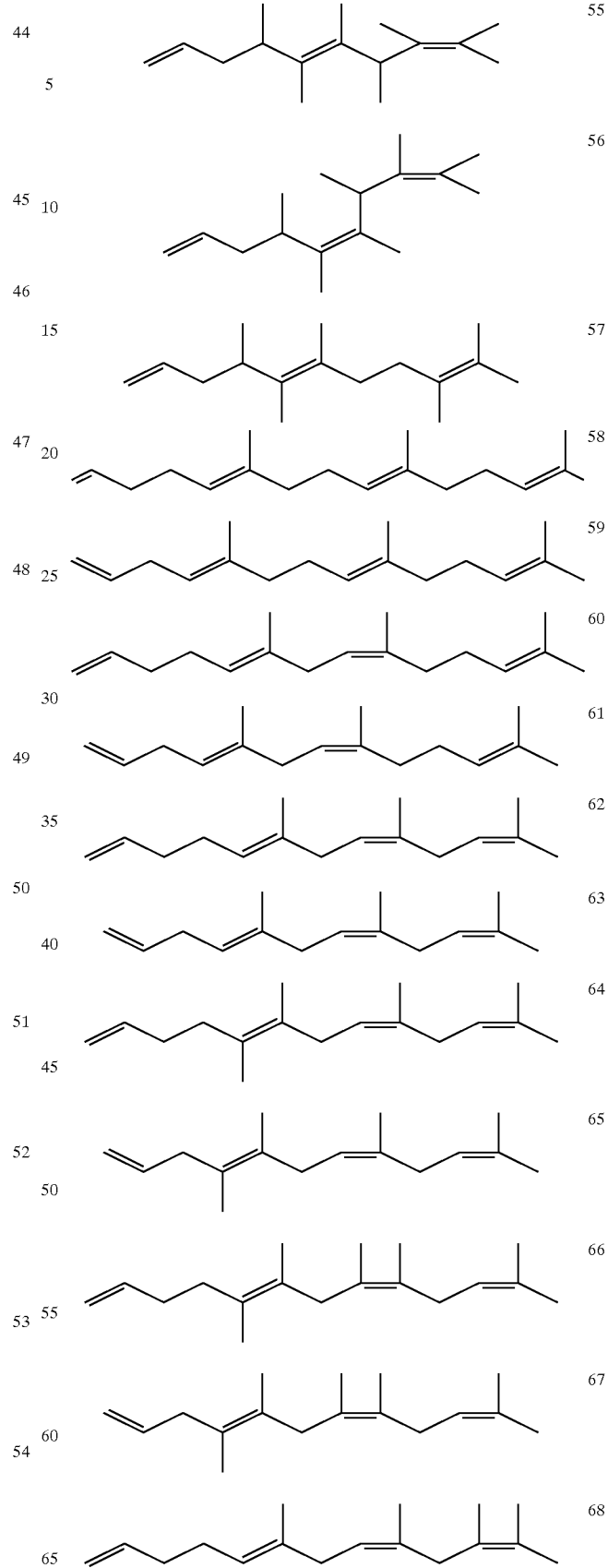

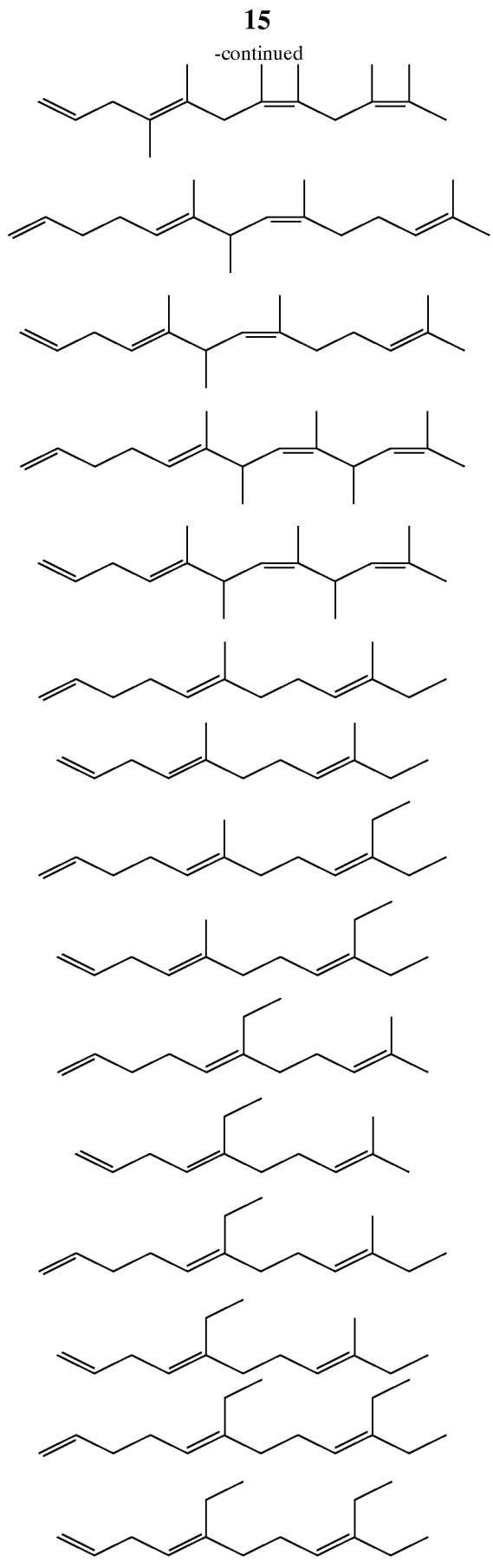

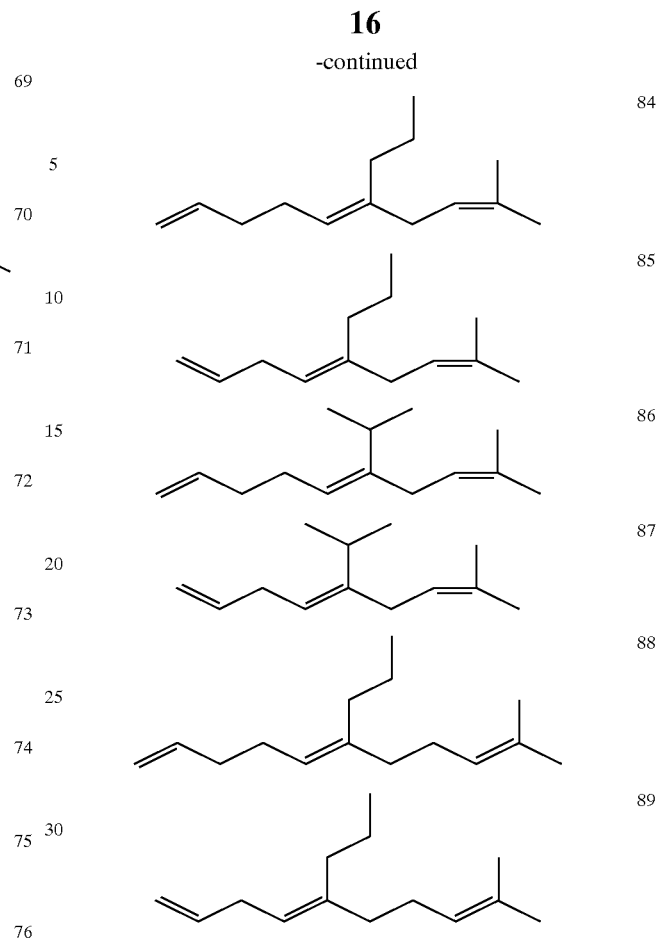

These compounds are used singly or in combination of two or more kinds.

The straight chain triene or tetraene (iii) can be prepared by, for example, a conventionally known process.

For example, a vinyl group-containing halide (e.g., allyl halide or vinyl halide) is reacted with metallic Mg to prepare a Grignard reagent (e.g., allyl-MgX or vinyl-MgX). This Grignard reagent is then reacted with a halogenated product of nonconjugated double bond-containing straight chain hydrocarbon (e.g., geranyl halide) by free radical reaction, so as to prepare the straight chain polyene (iii).

Nonconjugated triene or tetraene (Ib)

The preferred nonconjugated triene or tetraene (iii) among the above compound (H-1) is a branched chain triene or tetraene represented by the following formula (Ib) (sometimes referred to as branched chain polyene).

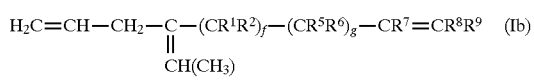

This nonconjugated triene or tetraene (Ib) is a nonconjugated triene or tetraene of the above formula (H-1) wherein p is 1; q is 0; f is an integer of 0 to 5; g is an integer of 1 to 6; and $R^1$ to $R^9$ have the meanings as defined above.

Preferably, $R^1$, $R^2$, $R^5$, $R^6$ and $R^7$ are each hydrogen or an alkyl group of 1 to 5 carbon atoms, preferably hydrogen or an alkyl group of 1 to 3 carbon atoms. Particularly preferably, $R^1$, $R^2$, $R^5$ and $R^6$ are all hydrogen.

Preferably, $R^8$ is an alkyl group of 1 to 5, preferably 1 to 3 carbon atoms.

Preferably, $R^9$ is hydrogen, an alkyl group of 1 to 5, preferably 1 to 3 carbon atoms, or a group represented by the formula $-(CH_2)_n-CR^{10}=CR^{11}R^{12}$, where n is an integer of 1 to 5, preferably 1 to 3; $R^{10}$ is hydrogen or an alkyl group of 1 to 5 carbon atoms, preferably 1 to 3; $R^{11}$ is hydrogen or an alkyl of 1 to 5, preferably 1 to 3 carbon atoms; and $R^{12}$ is an alkyl group of 1 to 5, preferably 1 to 3 carbon atoms. Most preferred as $R^9$ is an alkyl group of the above-mentioned carbon atoms.

Of the nonconjugated trienes or tetraenes (Ib), preferably used are the nonconjugated trienes of the formula (Ic) or the nonconjugated tetraenes of the formula (Ib'), particularly preferably the compound of the formula (Ib), wherein $R^1$, $R^2$, $R^5$ and $R^6$ are each hydrogen, that is, a nonconjugated triene represented by the following formula (Ib-1) (branched chain triene) or a nonconjugated tetraene represented by the following formula (Ib') (branched chain tetraene). The nonconjugated triene (Ib-1) is especially preferred.

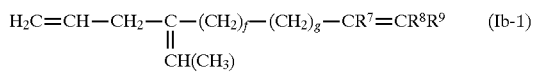

wherein f, g and $R^7$, $R^8$ and $R^9$ have the same meanings as described in the formula (Ib), and preferred ones are the same as above.

Examples of the branched chain polyenes (iii) (Ib-1) include the following compounds (1) to (24), and of the compounds, preferably used are the compounds (5), (6), (9), (11), (14), (19) and (20).

(1) 4-Ethylidene-1,6-octadiene,
(2) 7-Methyl-4-ethylidene-1,6-octadiene,
(3) 7-Methyl-4-ethylidene-1,6-nonadiene,
(4) 7-Ethyl-4-ethylidene-1,6-nonadiene,
(5) 6,7-Dimethyl-4-ethylidene-1,6-octadiene,
(6) 6,7-Dimethyl-4-ethylidene-1,6-nonadiene,
(7) 4-Ethylidene-1,6-decadiene,
(8) 7-Methyl-4-ethylidene-1,6-decadiene,
(9) 7-Methyl-6-propyl-4-ethylidene-1,6-octadiene,
(10) 4-Ethylidene-1,7-nonadiene,
(11) 8-Methyl-4-ethylidene-1,7-nonadiene (EMN),
(12) 4-Ethylidene-1,7-undecadiene,
(13) 8-Methyl-4-ethylidene-1,7-undecadiene,
(14) 7,8-Dimethyl-4-ethylidene-1,7-nonadiene,
(15) 7,8-Dimethyl-4-ethylidene-1,7-decadiene,
(16) 7,8-Dimethyl-4-ethylidene-1,7-undecadiene,
(17) 8-Methyl-7-ethyl-4-ethylidene-1,7-undecadiene,
(18) 7,8-Diethyl-4-ethylidene-1,7-decadiene,
(19) 9-Methyl-4-ethylidene-1,8-decadiene,
(20) 8,9-Dimethyl-4-ethylidene-1,8-decadiene,
(21) 10-Methyl-4-ethylidene-1,9-undecadiene,
(22) 9,10-Dimethyl-4-ethylidene-1,9-undecadiene,
(23) 11-Methyl-4-ethylidene-1,10-dodecadiene, and
(24) 10,11-Dimethyl-4-ethylidene-1,10-dodecadiene.

The chemical formulas of the above compounds (1) to (24) are described below.

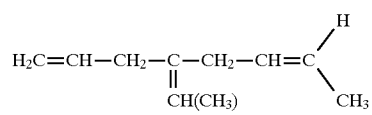

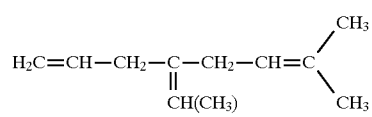

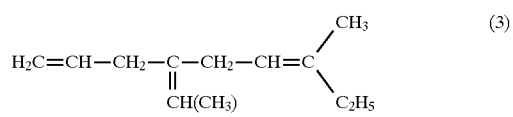

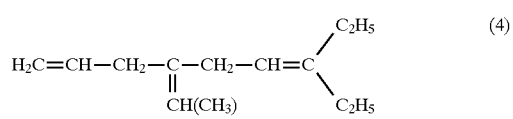

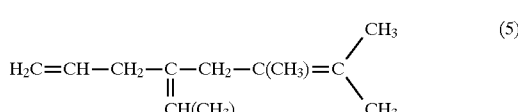

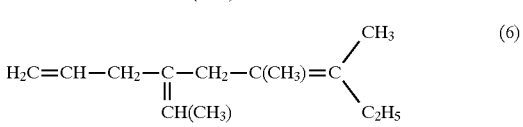

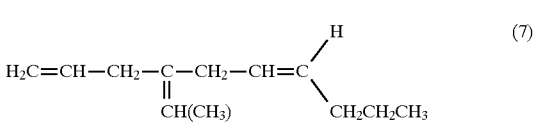

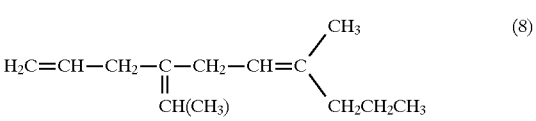

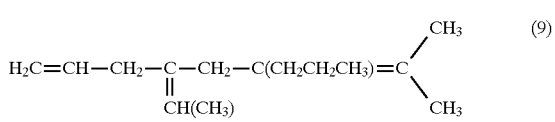

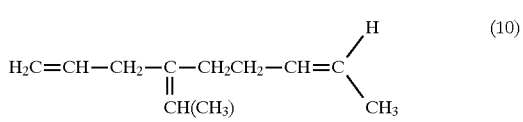

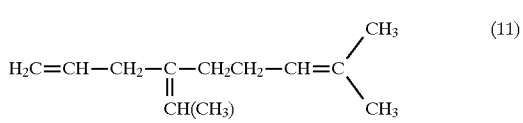

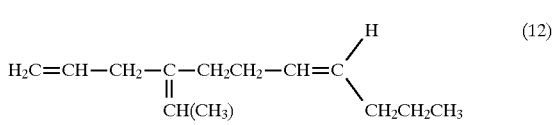

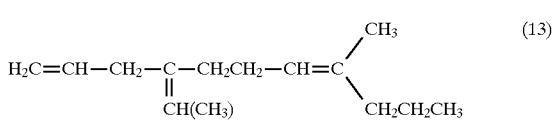

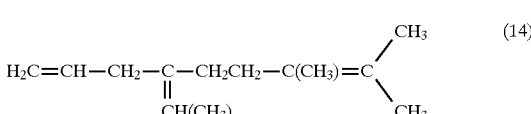

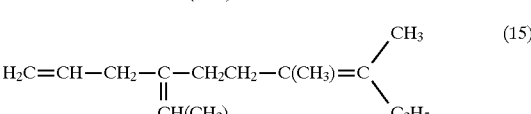

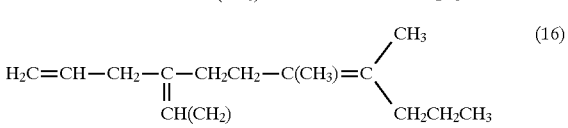

-continued

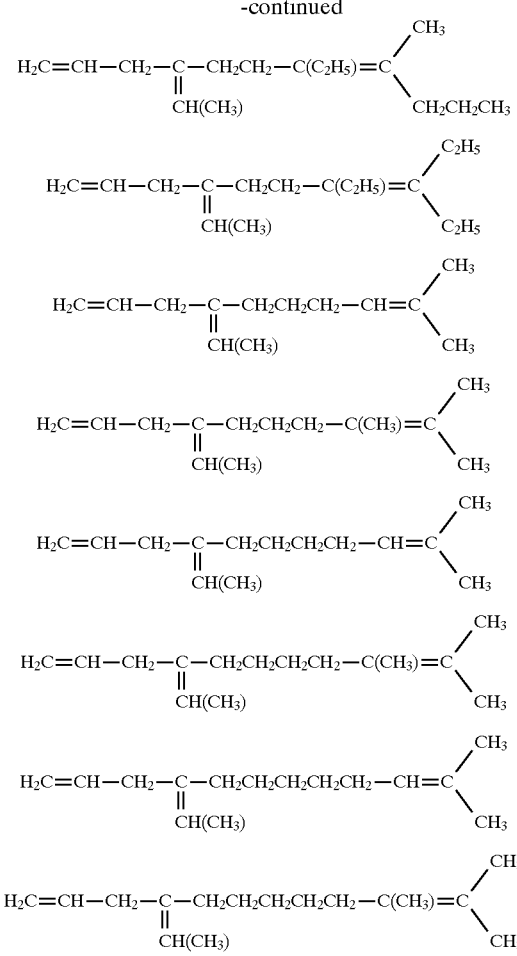

These compounds may be used singly or in combination of two or more kinds.

The branched chain triene or tetraene (Ib-1) used in the invention may be a mixture of a trans form and a cis form, or may be a trans form or a cis form alone.

The branched chain triene (iii) (Ib) can be prepared, for example, in accordance with the process described in Japanese Patent Application No. 154952/1995 by the present inventor.

That is, a compound having conjugated diene and represented by the following formula (I-a) is reacted with ethylene in the presence of a catalyst formed from a transition metal compound and an organoaluminum compound:

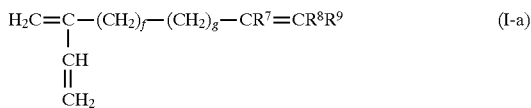

wherein f is an integer of 0 to 5; g is an integer of 1 to 6; $R^9$ is an alkyl group of 1 to 5 carbon atoms, and $R^7$ and $R^8$ are each independently hydrogen or an alkyl group of 1 to 5 carbon atoms.

Details of the process for preparing the branched chain polyene represented by the formula (Ib-1) are described later.

Among the nonconjugated polyene (Ib), more preferred is a compound represented by the following formula (Ib'):

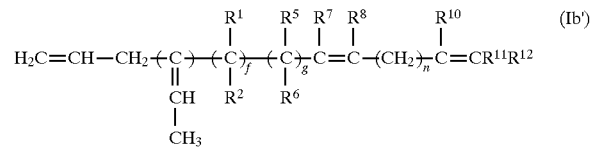

wherein f, g, n, $R^1$, $R^q$ and $R^5$ to $R^8$ and $R^{10}$ to $R^{12}$ have the meanings described in the formula (Ib), and preferred ones are the same as above.

Namely, this nonconjugated tetraene (branched chain tetraene) is the compound of the formula (Ib) wherein $R^9$ is particularly a group represented by the aforesaid formula —$(CH_2)_n$—$CR^{10}$=$CR^{11}R^{12}$, wherein n, $R^{10}$, $R^{11}$ and $R^{12}$ are the same as those in the formula (Ib). Employable as the compound (Ib') are for example, the following compounds (1) to (154), and of the compounds, preferably used is 4-ethylidene-8,12-dimethyl-1,7,11-tridecatriene (EDT, the compound 47).

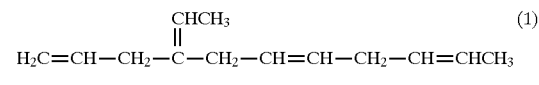
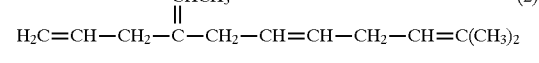
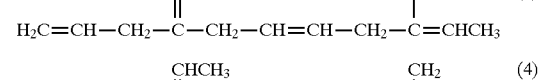
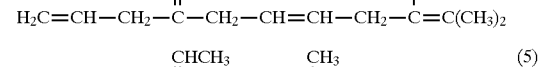
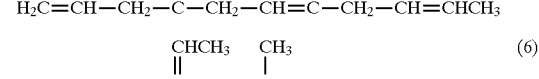
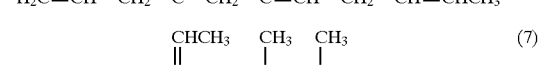
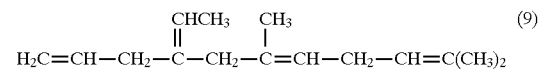
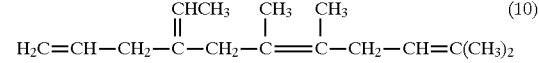
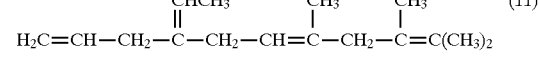
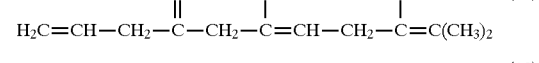
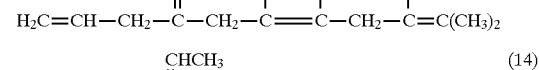
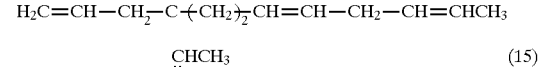
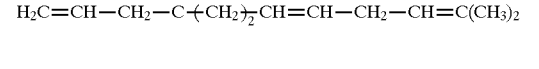

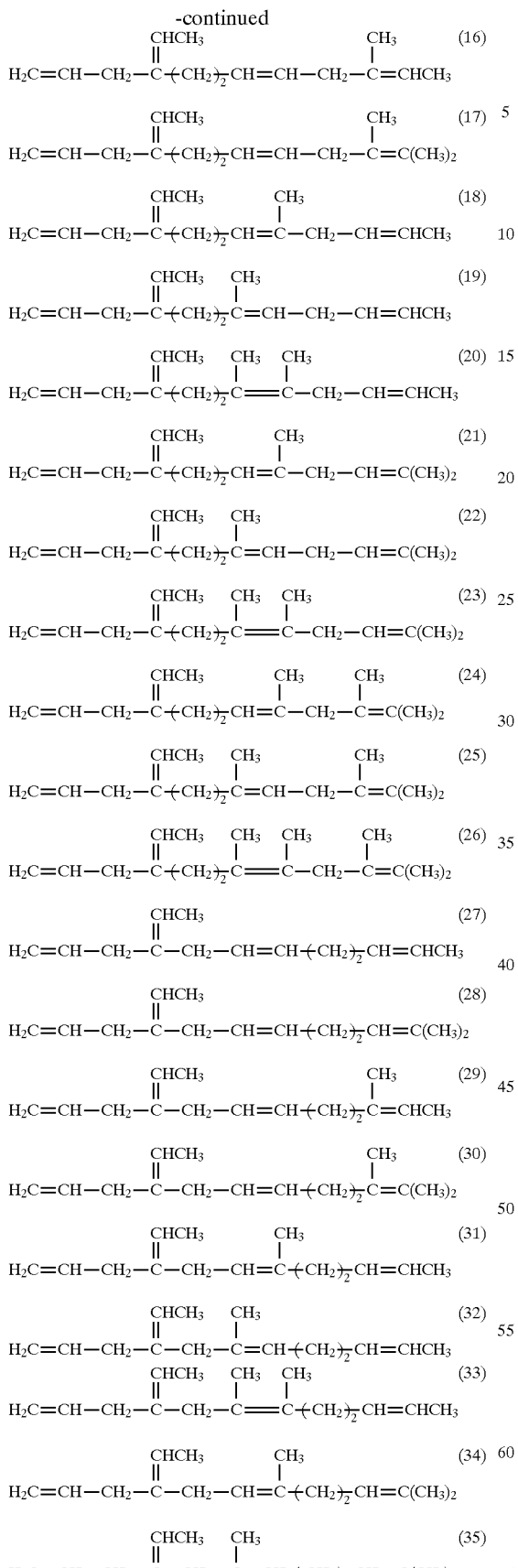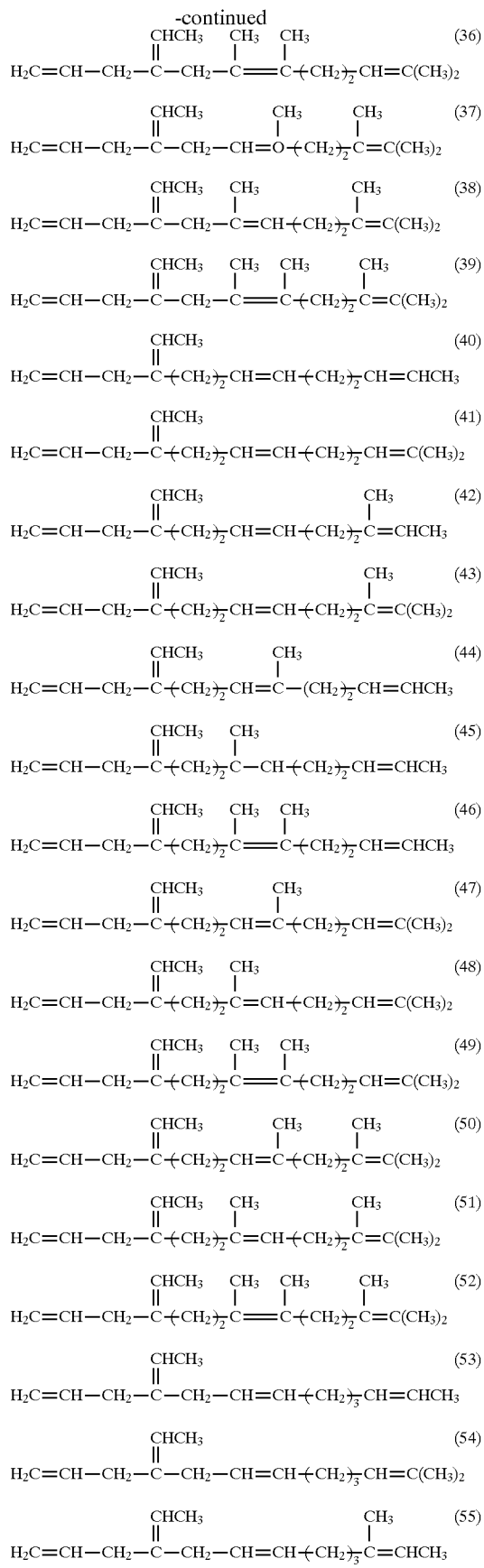

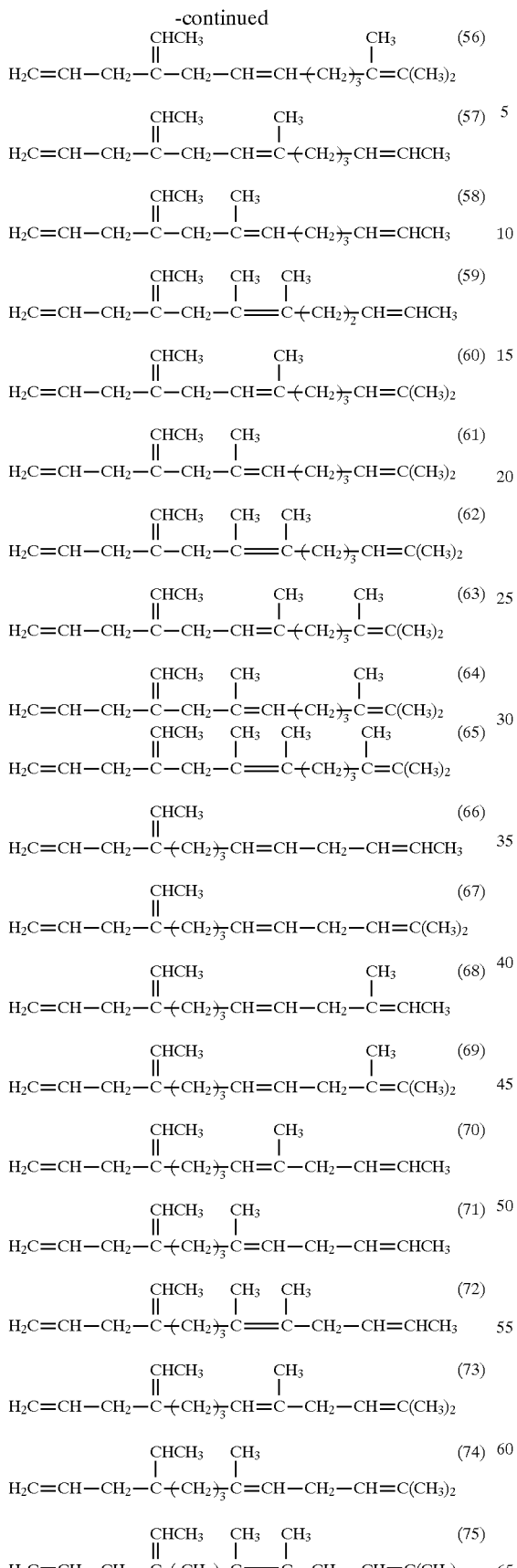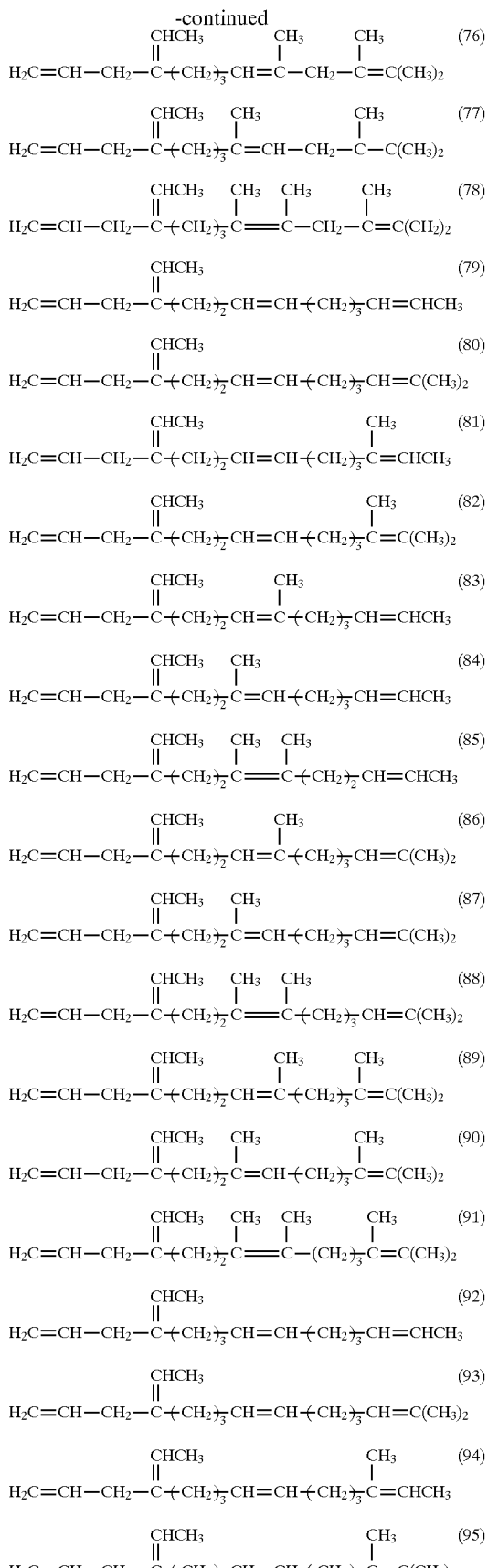

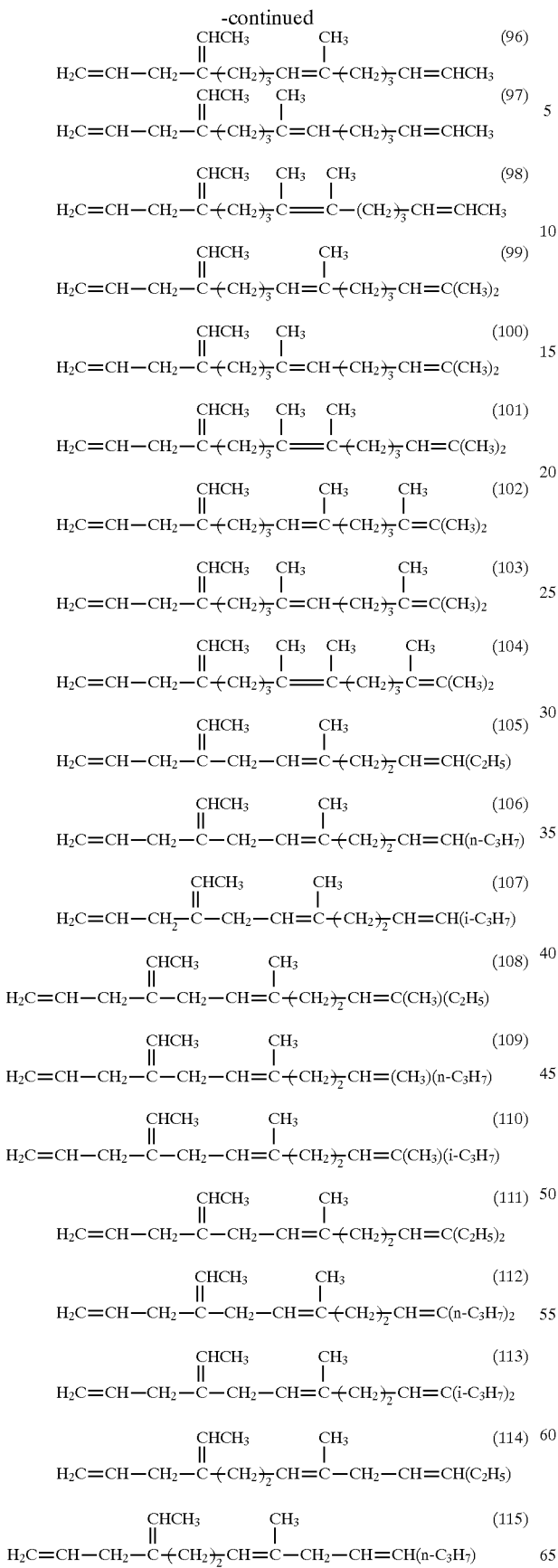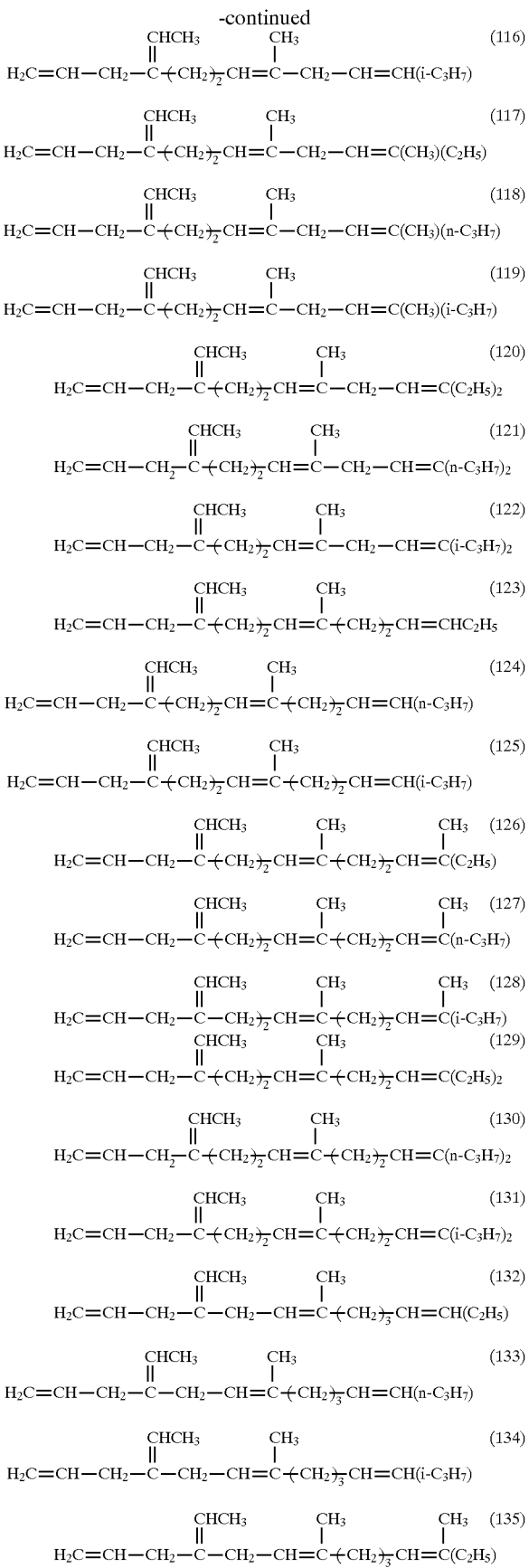

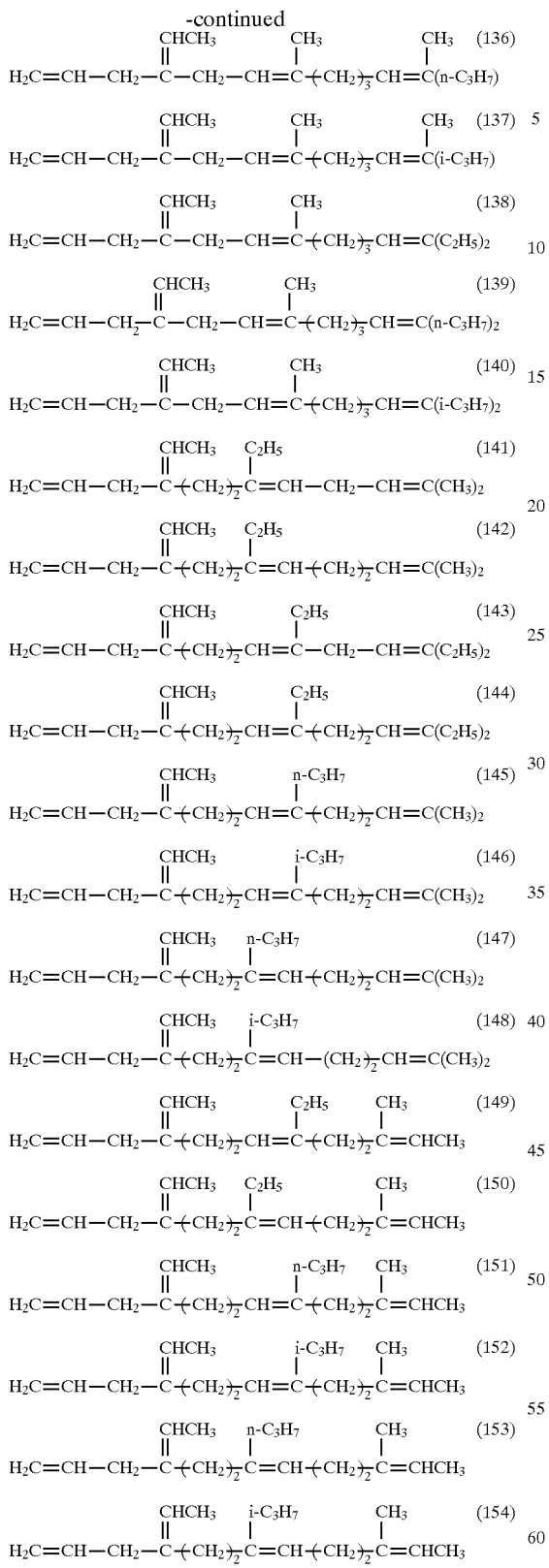

nonconjugated tetraene (1b'); or the straight chain nonconjugated triene or tetraene (Ia) and the branched chain polyene (Ib).

The structure of the branched chain tetraene (Ib') can be determined by, for example, mass spectrometric analysis or by measuring infrared absorption spectrum or proton NMR spectrum. The branched chain tetraene (Ib') generally has a geometrical isomeric structure (trans form or cis form). In the invention, the branched chain triene or tetraene may be a mixture of the above stereoisomers, or may be any one of the stereoisomers.

The branched chain tetraene (Ib') can be synthesized by a similar process to that of the nonconjugated triene or tetraene (Ib), which will be described later.

In the unsaturated copolymer of ethylene according to the invention, the constituent units derived from ethylene (i), the α-olefin (ii) and the nonconjugated triene or tetraene (iii) (sometimes referred to as polyene) are arranged at random and bonded to each other. Further, the unsaturated copolymer of ethylene has a branched structure caused by the nonconjugated triene or tetraene (polyene) (iii), and its main chain is of a substantially linear structure. That this copolymer has a substantially linear structure and does not substantially contain a polymer of crosslinked gel structure can be confirmed by the fact that the copolymer is dissolved in an organic solvent leaving substantially no insoluble component. For example, this can be confirmed by the fact that the copolymer is completely dissolved in Decalin at 135° C. in the measurement of the intrinsic viscosity ($\eta$).

The unsaturated copolymer of ethylene according to the invention comprises:

the constituent units from ethylene (i) in amounts of 30 to 92% by mol, preferably 40 to 90% by mol, more preferably 45 to 90% by mol;

the constituent units from the α-olefin of 3 to 20 carbon atoms (ii) in amounts of 6 to 70% by mol, preferably 8 to 60% by mol, more preferably 10 to 55% by mol; and the constituent units from the nonconjugated triene or tetraene (nonconjugated polyene) (iii) in amounts of 0.1 to 30% by mol, preferably 0.1 to 20% by mol, more preferably 0.2 to 10% by mol. When the copolymer containing the nonconjugated polyene (iii) is within the above range, the vulcanizing rate of the resulting rubber composition is increased and the vulcanized products therefrom have excellent properties.

In the unsaturated copolymer of ethylene, a molar ratio of the constituent units from the ethylene (i) to the constituent units from the α-olefin of 3 to 20 carbon atoms (ii) (ethylene (i)/α-olefin (ii)) is 40/60 to 92/8, preferably 45/55 to 90/10, more preferably 50/50 to 88/12. By the use of the unsaturated copolymer containing the ethylene (i) and the α-olefin (ii) within the above range of molar ratio, a composition excellent in vulcanizing properties and low-temperature properties can be obtained.

In the unsaturated copolymer of ethylene according to the invention, when the nonconjugated triene or tetraene (iii) in (A) is represented by the aforesaid formula (H-1), the constituent units from the nonconjugated triene or tetraene (iii) in (B) substantially have a structure represented by the following formula (H-2):

These nonconjugated polyenes may be used alone or in combination, for example, the branched chain nonconjugated triene (1c), preferably (Ib-1) and the branched chain

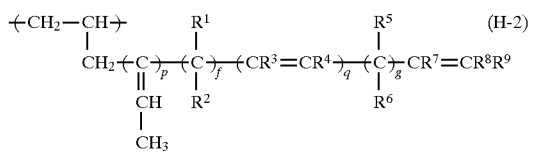

wherein p, q, f, g and $R^1$ to $R^9$ have the same meanings as described in the formula (H-1).

In the unsaturated copolymer of ethylene, when the nonconjugated triene or tetraene (iii) in (A) is represented by the aforesaid formula (Ia), the constituent units from the nonconjugated triene or tetraene (iii) in (B) substantially have a structure represented by the following formula (IIa):

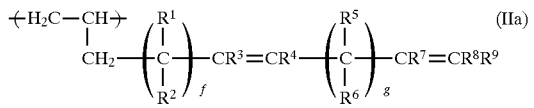

wherein f, g and $R^1$ to $R^9$ have the same meanings as described in the formula (Ia).

In the unsaturated copolymer of ethylene, when the nonconjugated triene or tetraene (iii) in (A) is represented by the aforesaid formula (Ib), the constituent units derived from the nonconjugated triene or tetraene (iii) in (B) substantially have a structure represented by the following formula (IIb):

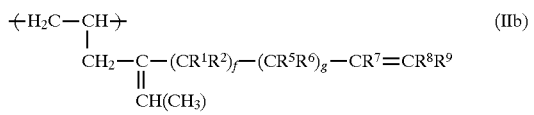

wherein f, g and $R^1$, $R^2$ and $R^5$ to $R^9$ have the same meanings as described in the formula (Ib).

That the constituent units derived from the nonconjugated triene or tetraene (polyene) have the above structures can be confirmed by measuring the $^{13}$C-NMR spectrum of the copolymer.

The unsaturated copolymer of ethylene according to the invention has an intrinsic viscosity (η), as measured in Decalin at 135° C., of 0.05 to 10 dl/g, preferably 0.1 to 7 dl/g, more preferably 0.2 to 5 dl/g.

The unsaturated copolymer of ethylene according to the invention is excellent in weathering resistance, heat resistance and ozone resistance and has a high vulcanizing rate.

The unsaturated copolymer of ethylene may be used in the unvulcanized state, or may be used in the vulcanized state by vulcanizing the copolymer through vulcanization methods described later. When the copolymer is used in the vulcanized state, its excellent properties are prominently exhibited.

The unsaturated copolymer of ethylene can be used as a resin modifier, or it can be used particularly preferably for various rubber products.

For example, if the unsaturated copolymer of ethylene is added as a resin modifier to polypropylene, polyethylene, polybutene or polystyrene, the impact resistance and the stress crack resistance is remarkably enhanced.

The unsaturated copolymer of ethylene may be used by vulcanizing it singly or in combination with other rubber materials.

Since this unsaturated copolymer of ethylene has a high vulcanizing rate, it can be vulcanized for a shorter period of time or at a lower temperature even when a large amount of a vulcanizing agent is not used, as compared with the conventional unsaturated copolymers of ethylene to produce vulcanized rubbers with high productivity.

The unsaturated copolymer of ethylene according to the invention shows good covulcanizability with, particularly, diene rubbers such as natural rubber, styrene-butadiene rubber, isoprene rubber, butadiene rubber, nitrile rubber and chloroprene rubber, and thus the resulting covulcanizates of the unsaturated copolymer of ethylene and the diene rubbers not only have excellent properties inherent in the diene rubbers such as high mechanical properties, abrasion resistance, dynamic fatigue resistance and oil resistance, but also excellent weathering resistance, ozone resistance and heat aging resistance.

For example, a covulcanizate of the unsaturated copolymer of ethylene according to the invention and a natural rubber exhibits excellent properties such as strength, weathering resistance, ozone resistance and dynamic properties.

A covulcanizate of the unsaturated copolymer of ethylene according to the invention and a nitrile rubber is excellent in weathering resistance, ozone resistance and oil resistance.

A covulcanizate of the unsaturated copolymer of ethylene according to the invention and a butadiene rubber is excellent in weathering resistance, ozone resistance and abrasion resistance.

Preparation of unsaturated copolymer of ethylene

The unsaturated copolymer of ethylene according to the invention can be obtained by copolymerizing (i) ethylene, (ii) an α-olefin of 3 to 20 carbon atoms and (iii) the nonconjugated triene or tetraene, preferably the nonconjugated triene or tetraene represented by the formula (H-1), more preferably (Ia) and (Ib'), in the presence of a catalyst. Among the nonconjugated polyene (Ib), particularly preferred are (Ib-1) and (Ib').

As the catalyst, catalysts comprising compounds of transition metals such as vanadium (V), zirconium (Zr) and titanium (Ti), and organoaluminum compounds (organoaluminum oxy-compound) and/or an ionized ionic compound are employable, and particularly preferably used in the invention are (a) a catalyst comprising a soluble vanadium compound and an organoaluminum compound, and (b) a catalyst comprising a metallocene compound of a transition metal selected from elements of Group IVB of the periodic table and an organoaluminum oxy-compound and/or an ionized ionic compound.

The soluble vanadium compound for forming the catalyst (a) is specifically represented by the following formula:

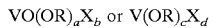

wherein R is a hydrocarbon group, X is a halogen atom, and a, b, c, d are numbers satisfying the conditions of $0 \leq a \leq 3$, $0 \leq b \leq 3$, $2 \leq a+b \leq 3$, $0 \leq c \leq 4$, $0 \leq d \leq 4$ and $3 \leq c+d \leq 4$.

Particular examples of the soluble vanadium compounds represented by the above formula include $VOCl_3$, $VO(OCH_3)Cl_2$, $VO(OC_2H_5)Cl_2$, $VO(OC_2H_5)_{1.5}Cl_{1.5}$, $VO(OC_2H_5)_2Cl$, $VO(O-n-C_3H_7)Cl_2$, $VO(O-iso-C_3H_7)Cl_2$, $VO(O-n-C_4H_9)Cl_2$, $VO(O-iso-C_4H_9)Cl_2$, $VO(O-sec-C_4H_9)Cl_2$, $VO(O-t-C_4H_9)Cl_2$, $VO(OC_2H_5)_3$, $VOBr_2$, $VCl_4$, $VOCl_2$, $VO(O-n-C_4H_9)_3$, and $VOCl_3 \cdot 20C_8H_{17}OH$.

These compounds are used singly or in combination of two or more kinds.

The soluble vanadium compounds may be used in the form of electron donor addition products of the soluble vanadium compounds which can be obtained by contacting these soluble vanadium compounds with the following electron donors.

Examples of the electron donors include:
oxygen-containing electron donors, such as alcohols, phenols, ketones, aldehydes, carboxylic acids, organic acid halides, esters of organic acids or inorganic acids, ethers, diethers, acid amides, acid anhydrides and alkoxysilanes; and nitrogen-containing electron donors, such as ammonias, amines, nitriles, pyridines and isocyanates.

More specifically, there can be mentioned:

alcohols of 1 to 18 carbon atoms, such as methanol, ethanol, propanol, butanol, pentanol, hexanol, 2-ethylhexanol, octanol, dodecanol, octadecyl alcohol, oleyl alcohol, benzyl alcohol, phenylethyl alcohol, cumyl alcohol, isopropyl alcohol and isopropylbenzyl alcohol;

halogen-containing alcohols of 1 to 18 carbon atoms, such as trichloromethanol, trichlorcethanol and trichlorohexanol;

phenols of 6 to 20 carbon atoms which may have alkyl groups, such as phenol, cresol, xylenol, ethylphenol, propylphenol, nonylphenol, cumylphenol and naphthol;

ketones of 3 to 15 carbon atoms, such as acetone, methyl ethyl ketone, methyl isobutyl ketone, acetophenone, benzophenone and benzoquinone;

aldehydes of 2 to 15 carbon atoms, such as acetaldehyde, propionaldehyde, octylaldehyde, benzaldehyde, tolualdehyde and naphthaldehyde;

organic acid esters of 2 to 18 carbon atoms, such as methyl formate, methyl acetate, ethyl acetate, vinyl acetate, propyl acetate, octyl acetate, cyclohexyl acetate, ethyl propionate, methyl butyrate, ethyl valerate, methyl chloroacetate, ethyl dichloroacetate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, methyl toluate, ethyl toluate, amyl toluate, ethyl ethylbenzoate, methyl anisate, ethyl anisate, ethyl ethoxybenzoate, γ-butyrolactone, δ-valerolactone, coumarin, phthalide and ethyl carbonate;

acid halides of 2 to 15 carbon atoms, such as acetyl chloride, benzoyl chloride, toluoyl chloride and anisoyl chloride;

ethers of 2 to 20 carbon atoms, such as methyl ether, ethyl ether, isopropyl ether, butyl ether, amyl ether, tetrahydrofuran, anisole and diphenyl ether;

acid anhydrides, such as acetic anhydride, phthalic anhydride and benzoic anhydride;

alkoxysilanes, such as ethyl silicate and diphenyldimethoxysilane;

acid amides, such as N,N-dimethylacetamide, N,N-diethylbenzamide and N,N-dimethyltoluamide;

amines, such as trimethylamine, triethylamine, tributylamine, tribenzylamine and tetramethylethylenediamine;

nitriles, such as acetonitrile, benzonitrile and tolunitrile; and pyridines, such as pyridine, methylpyridine, ethylpyridine and dimethylpyridine.

In the preparation of the electron donor addition products of the soluble vanadium compounds, the above electron donors may be used alone or in combination of two or more kinds.

In the present invention, the organoaluminum compound used for forming the catalyst (a) is represented by the following formula (III):

$$R^1{}_n AlX_{3-n} \quad (III)$$

wherein $R^1$ is a hydrocarbon group of 1 to 15, preferably 1 to 4 carbon atoms, X is a halogen atom or hydrogen, and n is 1 to 3.

The hydrocarbon group of 1 to 15 carbon atoms is, for example, an alkyl group, a cycloalkyl group or an aryl group, and particular examples include methyl, ethyl, n-propyl, isopropyl, isobutyl, pentyl, hexyl, octyl, cyclopentyl, cyclohexyl, phenyl and tolyl.

Examples of such organoaluminum compounds include:

trialkylaluminums, such as trimethylaluminum, triethylaluminum, triisopropylaluminum, triisobutylalumium, trioctylaluminum and tri-2-ethylhexylaluminum;

alkenylaluminums represented by the formula $(iC_4H_9)_x Al_y (C_5H_{10})_z$ (x, y and z are each a positive number, and $z \geq 2x$), such as isoprenylaluminum;

trialkenylaluminums, such as triisopropenylaluminum;

dialkylaluminum halides, such as dimethylaluminum chloride, diethylaluminum chloride, diisopropylaluminum chloride, diisobutylaluminum chloride and dimethylaluminum bromide;

alkylaluminum sesquihalides, such as methylaluminum sesquichloride, ethylaluminum sesquichloride, isopropylaluminum sesquichloride, butylaluminum sesquichloride and ethylaluminum sesquibromide;

alkylaluminum dihalides, such as methylaluminum dichloride, ethylaluminum dichloride, isopropylalumium dichloride and ethylaluminum dibromide;

dialkylaluminum hydrides, such as diethylaluminum hydride and dibutylaluminum hydride; and alkylaluminum dihydrides, such as ethylaluminum dihydride and propylaluminum dihydride.

Also employable as the organoaluminum compound is a compound represented by the following formula (IV):

$$R^1{}_n AlY_{3-n} \quad (IV)$$

wherein $R^1$ is the same as in the above formula (III); Y is $-OR^{10}$ group, $-OSiR^{11}{}_3$ group, $-OAlR^{12}{}_2$ group, $-NR^{13}{}_2$ group, $SiR^{14}{}_3$ group or $-N(R^{15})AlR^{16}{}_2$ group; $R^{10}$, $R^{11}$, $R^{12}$ and $R^{16}$ are each methyl, ethyl, isopropyl, isobutyl, cyclohexyl or phenyl; $R^{13}$ is hydrogen, methyl, ethyl, isopropyl, phenyl or trimethylsilyl; $R^{14}$ and $R^{15}$ are each methyl or ethyl; and n is 1 to 2.

The organoaluminum compounds represented by the formula (IV) include compounds of the following formulas wherein Me is methyl, Et is ethyl, Bu is butyl, and $R^1$ to $R^{16}$ are the same as those in the formula (IV).

(1) Compounds of the formula $R^1{}_n Al(OR^{10})_{3-n}$, e.g., dialkylaluminum alkoxides, such as dimethylaluminum methoxide, diethylaluminum ethoxide and diisobutylaluminum methoxide; partially alkoxylated alkylaluminums, such as ethylaluminum sesquiethoxide, butylaluminum sesquibutoxide and those having an average composition represented by, e.g., $R^1{}_{2.5}Al(OR^2)_{0.5}$; and partially alkoxylated and halogenated alkylaluminums, such as ethylaluminum ethoxychloride, butylaluminum butoxychloride and ethylaluminum ethoxybromide;

(2) Compounds of the formula $R^1{}_n Al(OSiR^{11}{}_3)_{3-n}$, e.g., $Et_2Al(OSiMe_3)$, $(iso-Bu)_2Al(OSiMe_3)$ and $(iso-Bu)_2Al(OSiEt_3)$;

(3) Compounds of the formula $R^1{}_n Al(OAlR^{12}{}_2)_{3-n}$, e.g., $Et_2AlOAlEt_2$ and $(iso-Bu)_2AlOAl(iso-Bu)_2$;

(4) Compounds of the formula $R^1{}_nAl(NR^{13}{}_2)_{3-n}$, e.g., $Me_2AlNEt_2$, $Et_2AlNHMe$, $Me_2AlNHEt$, $Et_2AlN(SiMe_3)_2$ and $(iso-Bu)_2AlN(SiMe_3)_2$;

(5) Compounds of the formula $R^1{}_nAl(SiR^{14}{}_3)_{3-n}$, e.g., $(iso-Bu)_2AlSiMe_3$; and (6) Compounds of the formula $R^1{}_nAl(N(R^{13})AlR^{16}{}_2)_{3-n}$, e.g., $Et_2AlN(Me)AlEt_2$ and $(iso-Bu)_2AlN(Et)Al(iso-Bu)_2$.

Of the above compounds, preferred are alkylaluminum halides, alkylaluminum dihalides or combinations thereof.

The organoaluminum compound used in the invention may contain an organometallic compound component of other metal than aluminum in a small amount.

Next, the catalyst (b) used in the invention, which comprises a metallocene compound and an organoaluminum oxy-compound or an ionized ionic compound, is described.

The metallocene compound of a transition metal selected from elements of Group IVB of the periodic table is represented by the following formula (V).

$$ML_x \qquad (V)$$

In the formula (V), M is a transition metal selected from elements of Group IVB of the periodic table, e.g., zirconium, titanium or hafnium, and x is a valence of the transition metal.

L is a ligand coordinated to the transition metal. At least one ligand L is a ligand having a cyclopentadienyl skeleton which may have a substituent.

Examples of the ligands having a cyclopentadienyl skeleton include alkyl or cycloalkyl substituted cyclopentadienyl groups, such as cyclopentadienyl, methylcyclopentadienyl, ethylcyclopentadienyl, n- or i-propylcyclopentadienyl, n-, i-, sec- or t-butylcyclopentadienyl, hexylcyclopentadienyl, octylcyclopentadienyl, dimethylcyclopentadienyl, trimethylcyclopentadienyl, tetramethylcyclopentadienyl, pentamethylcyclopentadienyl, methylethylcyclopentadienyl, methylpropylcyclopentadienyl, methylbutylcyclopentadienyl, methylhexylcyclopentadienyl, methylbenzylcyclopentadienyl, ethylbutylcyclopentadienyl, ethylhexylcyclopentadienyl and methylcyclohexylcyclopentadienyl.

Further, an indenyl group, a 4,5,6,7-tetrahydroindenyl group and a fluorenyl group can be also mentioned.

Those groups may be substituted with halogen atoms or trialkylsilyl groups.

Of the above ligands, particularly preferred are alkyl substituted cyclopentadienyl groups.

When the compound represented by the formula (V) has two or more ligands L having a cyclopentadienyl skeleton, two of the ligands having a cyclopentadienyl skeleton may be bonded to each other through an alkylene group such as ethylene or propylene, isopropylidene, a substituted alkylene group such as diphenylmethylene, a silylene group, or a substituted silylene group such as dimethylsilylene, diphenylsilylene or methylphenylsilylene.

Examples of L other than the ligand having a cyclopentadienyl skeleton include a hydrocarbon group of 1 to 12 carbon atoms, an alkoxyl group, an aryloxy group, a sulfonic acid-containing group ($—SO_3R^a$), a halogen atom or hydrogen, where $R^a$ is an alkyl group, an alkyl group substituted with a halogen atom, an aryl group, or an aryl group substituted with a halogen atom or an alkyl group.

Examples of the hydrocarbon groups of 1 to 12 carbon atoms include alkyl groups, cycloalkyl groups, aryl groups and aralkyl groups, more specifically, there can be mentioned:

alkyl groups, such as methyl, ethyl, n-propyl, isopropyl, n-butyl, isobutyl, sec-butyl, t-butyl, pentyl, hexyl, octyl, decyl and dodecyl;

cycloalkyl groups, such as cyclopentyl and cyclohexyl;

aryl groups, such as phenyl and tolyl; and aralkyl group, such as benzyl and neophyl.

Examples of the alkoxy groups include methoxy, ethoxy, n-propoxy, isopropoxy, n-butoxy, isobutoxy, sec-butoxy, t-butoxy, pentoxy, hexoxy and octoxy.

The aryloxy group is, for example, phenoxy.

Examples of the sulfonic acid-containing group ($—SO_3R^a$) include methanesulfonato, p-toluenesulfonato, trifluoromethansulfonate and p-chlorobenzenesulfonato.

Examples of the halogen atoms include fluorine, chlorine, bromine and iodine.

The metallocene compound of the above formula wherein the valence of the transition metal is 4 is more specifically represented by the following formula (VI):

$$R^2{}_KR^3{}_lR^4{}_mR^5{}_nM \qquad (VI)$$

wherein M is the above-mentioned transition metal, $R^2$ is a group (ligand) having a cyclopentadienyl skeleton, $R^3$, $R^4$ and $R^5$ are each independently a group having a cyclopentadienyl skeleton or the same as L other than the ligand having a cyclopentadienyl skeleton in the above formula (V), k is an integer of not less than 1, and k+l+m+n=4.

Listed below are examples of the metallocene compounds containing zirconium as M and containing at least two ligands having a cyclopentadienyl skeleton.

Bis(cyclopentadienyl)zirconium monochloride monohydride,
Bis(cyclopentadienyl)zirconium dichloride,
Bis(cyclopentadienyl)zirconium dibromide,
Bis(cyclopentadienyl)methylzirconium monochloride,
Bis(cyclopentadienyl)zirconium phenoxymonochloride,
Bis(methylcyclopentadienyl)zirconium dichloride,
Bis(ethylcyclopentadienyl)zirconium dichloride,
Bis(n-propylcyclopentadienyl)zirconium dichloride,
Bis(isopropylcyclopentadienyl)zirconium dichloride,
Bis(t-butylcyclopentadienyl)zirconium dichloride,
Bis(n-butylcyclopentadienyl)zirconium dichloride,
Bis(sec-butylcyclopentadienyl)zirconium dichloride,
Bis(isobutylcyclopentadienyl)zirconium dichloride,
Bis(hexylcyclopentadienyl)zirconium dichloride,
Bis(octylcyclopentadienyl)zirconium dichloride,
Bis(indenyl)zirconium dichloride,
Bis(4,5,6,7-tetrahydroindenyl)zirconium dichloride,
Bis(indenyl)zirconium dibromide,
Bis(cyclopentadienyl)zirconium dimethyl,
Bis(cyclopentadienyl)zirconium methoxychloride,
Bis(cyclopentadienyl)zirconium ethoxychloride,
Bis(fluorenyl)zirconium dichloride,
Bis(cyclopentadienyl)zirconiumbis(methanesulfonato),
Bis(cyclopentadienyl)zirconiumbis(p-toluenesulfonato),
Bis(cyclopentadienyl)zirconiumbis(trifluoromethanesulfonato),
Bis(methylcyclopentadienyl)zirconiumbis(trifluoromethanesulfonato),
Bis(ethylcyclopentadienyl)zirconiumbis(trifluoromethanesulfonato),
Bis(propylcyclopentadienyl)zirconiumbis(trifluoromethanesulfonato), Bis(butylcyclopentadienyl)zirconiumbis (trifluoromethanesulfonato),
Bis(hexylcyclopentadienyl)zirconiumbis (trifluoromethanesulfonato),
Bis(1,3-dimethylcyclopentadienyl)zirconiumbis (trifluoromethanesulfonato),
Bis(1-methyl-3-ethylcyclopentadienyl)zirconiumbis (trifluoromethanesulfonato),
Bis(1-methyl-3-propylcyclopentadienyl)zirconiumbis (trifluoromethanesulfonato),
Bis(1-methyl-3-butylcyclopentadienyl)zirconiumbis (trifluoromethanesulfonato),
Bis(1,3-dimethylcyclopentadienyl)zirconium dichloride,
Bis(1-methyl-3-ethylcyclopentadienyl)zirconium dichloride,
Bis(1-methyl-3-propylcyclopentadienyl)zirconium dichloride,
Bis(1-methyl-3-butylcyclopentadienyl)zirconium dichloride,
Bis(1-methyl-3-hexylcyclopentadienyl)zirconium dichloride,
Bis(1-methyl-3-octylcyclopentadienyl)zirconium dichloride,
Bis(1-ethyl-3-butylcyclopentadienyl)zirconium dichloride,
Bis(trimethylcyclopentadienyl)zirconium dichloride,
Bis(tetramethylcyclopentadienyl)zirconium dichloride,
Bis(pentamethylcyclopentadienyl)zirconium dichloride,
Bis(methylbenzylcyclopentadienyl)zirconium dichloride,
Bis(ethylhexylcyclopentadienyl)zirconium dichloride, and
Bis(methylcyclohexylcyclopentadienyl)zirconium dichloride.

Also employable in the invention are those compounds wherein the 1,3-position substituted cyclopentadienyl group is replaced with a 1,2-position substituted cyclopentadienyl group.

Other examples are bridge type metallocene compounds of the above formula (VI) wherein at least two of $R^2$, $R^3$, $R^4$ and R5, e.g., $R^2$ and $R^3$, are groups (ligands) having a cyclopentadienyl skeleton, and the at least two groups are bonded to each other through an alkylene group, a substituted alkylene group, a silylene group or a substituted silylene group. In these compounds, $R^4$ and $R^5$ are each independently the same as L other than the ligand having a cyclopentadienyl skeleton, as described in the formula (V).

Listed below are examples of such bridge type metallocene compounds.
Ethylenebis(indenyl)dimethylzirconium,
Ethylenebis(indenyl)zirconium dichloride,
Ethylenebis(indenyl)zirconiumbis (trifluoromethanesulfonato),
Ethylenebis(indenyl)zirconiumbis(methanesulfonato),
Ethylenebis(indenyl)zirconiumbis(p-toluenesulfonato),
Ethylenebis(indenyl)zirconiumbis(p-chlorobenzenesulfonato),
Ethylenebis(4,5,6,7-tetrahydroindenyl)zirconium dichloride,
Isopropylidene(cyclopentadienyl-fluorenyl)zirconium dichloride,
Isopropylidene(cyclopentadienyl-methylcyclopentadienyl)zirconium dichloride,
Dimethylsilylenebis(cyclopentadienyl)zirconium dichloride,
Dimethylsilylenebis(methylcyclopentadienyl)zirconium dichloride,
Dimethylsilylenebis(dimethylcyclopentadienyl) zirconium dichloride,
Dimethylsilylenebis(trimethylcyclopentadienyl) zirconium dichloride,
Dimethylsilylenebis(indenyl)zirconium dichloride,
Dimethylsilylenebis(indenyl)zirconiumbis (trifluoromethanesulfonato),
Dimethylsilylenebis(4,5,6,7-tetrahydroindenyl)zirconium dichloride,
Dimethylsilylenebis(cyclopentadienylfluorenyl) zirconium dichloride,
Diphenylsilylenebis(indenyl)zirconium dichloride, and
Methylphenylsilylenebis(indenyl)zirconium dichloride.

Further, a metallocene compound of the following formula (A), which is described in Japanese Patent Laid-Open Publication No. 268307/1992, is also employable.

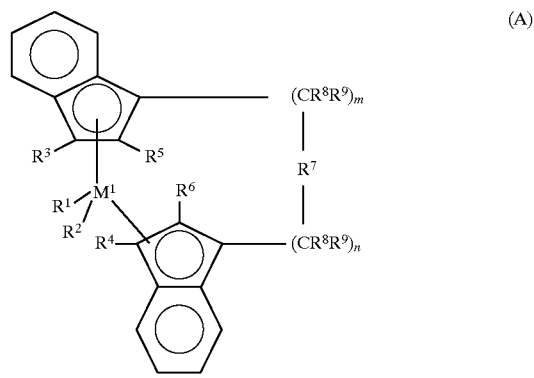

(A)

In the formula (A), $M^1$ is a metal of Group IVB of the periodic table, e.g., titanium, zirconium or hafnium.

$R^1$ and $R^2$ may be the same or different, and are each hydrogen, an alkyl group of 1 to 10, preferably 1 to 3 carbon atoms, an alkoxy group of 1 to 10, preferably 1 to 3 carbon atoms, an aryl group of 6 to 10, preferably 6 to 8 carbon atoms, an aryloxy group of 6 to 10, preferably 6 to 8 carbon atoms, an alkenyl group of 2 to 10, preferably 2 to 4 carbon atoms, an arylalkyl group of 7 to 40, preferably 7 to 10 carbon atoms, an alkylaryl group of 7 to 40, preferably 7 to 12 carbon atoms, an arylalkenyl group of 8 to 40, preferably 8 to 12 carbon atoms, or a halogen atom, preferably chlorine.

$R^3$ and $R^4$ may be the same or different, and are each hydrogen, a halogen atom, preferably fluorine, chlorine or bromine, an alkyl group of 1 to 10, preferably 1 to 4 carbon atoms which may be halogenated, an aryl group of 6 to 10, preferably 6 to 8 carbon atoms, or a group of —$NR^{10}{}_2$, —$SR^{10}$, —$OSiR^{10}{}_3$, —$SiR^{10}{}_3$ or —$PR^{10}{}_2$, where $R^{10}$ is a halogen atom, preferably chlorine, an alkyl group of 1 to 10, preferably 1 to 3 carbon atoms, or an aryl group of 6 to 10, preferably 6 to 8 carbon atoms.

$R^3$ and $R^4$ are each particularly preferably hydrogen.

$R^5$ and $R^6$ may be the same or different, preferably the same, and have the same meanings as described for $R^3$ and $R^4$ with the proviso that each of $R^5$ and $R^6$ is not hydrogen. $R^5$ and $R^6$ are each preferably an alkyl group of 1 to 4 carbon atoms which may be halogenated, for example, methyl, ethyl, propyl, isopropyl, butyl, isobutyl or trifluoromethyl, preferably methyl.

$R^7$ is

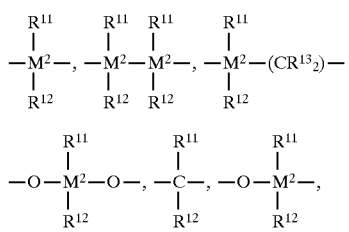

$=BR^{11}$, $=AlR^{11}$, —Ge—, —Sn—, —O—, —S—, $=SO$, $=SO_2$, $=NR^{11}$, $=CO$, $=PR^{11}$ or $=P(O)R^{11}$, where $R^{11}$, $R^{12}$ and $R^{13}$ may be the same or different, and are each hydrogen, a halogen atom, an alkyl group of 1 to 10, preferably 1 to 4 carbon atoms, more preferably methyl, a fluoroalkyl group of 1 to 10 carbon atoms, preferably $CF_3$, an aryl group of 6 to 10, preferably 6 to 8 carbon atoms, a fluoroaryl group of 6 to 10 carbon atoms, preferably pentafluorophenyl, an alkoxy group of 1 to 10, preferably 1 to 4 carbon atoms, particularly preferably methoxy, an alkenyl group of 2 to 10, preferably 2 to 4 carbon atoms, an arylalkyl group of 7 to 40, preferably 7 to 10 carbon atoms, an arylalkenyl group of 8 to 40, preferably 8 to 12 carbon atoms, or an alkylaryl group of 7 to 40, preferably 7 to 12 carbon atoms, or $R^{11}$ and $R^{12}$, or $R^{11}$ and $R^{13}$ may form together with the carbon atoms to which they are bonded a ring.

$M^2$ is silicon, germanium or tin, preferably tin or germanium.

$R^7$ is preferably $=CR^{11}R^{12}$, $=SiR^{11}R^{12}$, $=GeR^{11}R^{12}$, —O—, —S—, $=SO$, $=PR^{11}$ or $=P(O)PR^{11}$.

$R^8$ and $R^9$ may be the same or different, and have the same meaning as described for $R^{11}$.

m and n may be the same or different, and are each 0, 1 or 2, preferably 0 or 1, and m+n is 0, 1 or 2, preferably 0 or 1.

Particularly preferred metallocene compounds satisfying the above conditions are compounds represented by the following formulas (i) to (iii).

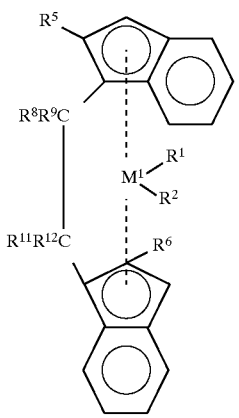

(i)

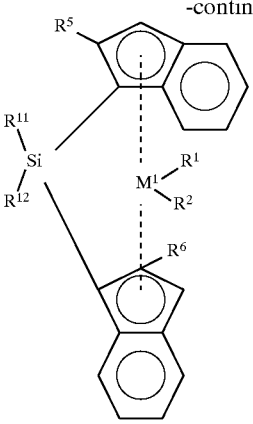

(ii)

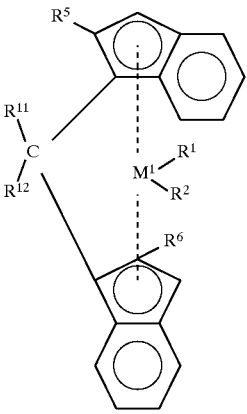

(iii)

In the above formulas (i), (ii) and (iii), $M^1$ is Zr or Hf, $R^1$ and $R^2$ are each methyl or chlorine, $R^5$ and $R^6$ are each methyl, ethyl or trifluoromethyl, and $R^8$, $R^9$, $R^{10}$ and $R^{12}$ have the same meanings as described above.

Of the compounds represented by the formulas (i), (ii) and (iii), particularly preferred are the following compounds:

rac-ethylene(2-methyl-1-indenyl)$_2$-zirconium dichloride, rac-dimethylsilylene(2-methyl-1-indenyl)$_2$-zirconium dichloride, rac-dimethylsilylene(2-methyl-1-indenyl)$_2$-zirconium dimethyl, rac-ethylene(2-methyl-1-indenyl)$_2$-zirconium dimethyl, rac-phenyl(methyl)silylene-(2-methyl-1-indenyl)$_2$-zirconium dichloride, rac-diphenyl-silylene-(2-methyl-1-indenyl)$_2$-zirconium dichloride, rac-methylethylene(2-ethyl-1-indenyl)$_2$-zirconium dichloride, and rac-dimethylsilylene(2-ethyl-1-indenyl)$_2$-zirconium dichloride.

These metallocene compounds can be prepared by conventionally known processes (see, for example, Japanese Patent Laid-Open Publication No. 26830/1992).

In the present invention, a transition metal compound (metallocene compound) represented by the following formula (B) is also employable.

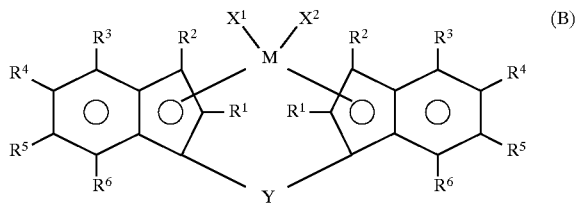

(B)

In the formula (B), M is a transition metal atom of Group IVB of the periodic table, specifically, titanium, zirconium or hafnium.

$R^1$ and $R^2$ are each independently hydrogen, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group.

Examples of the halogen atoms include fluorine, chlorine, bromine and iodine.

Examples of the hydrocarbon groups of 1 to 20 carbon atoms include alkyl groups, such as methyl, ethyl, propyl, butyl, hexyl, cyclohexyl, octyl, nonyl, dodecyl, eicosyl, norbornyl and adamantyl; alkenyl groups, such as vinyl, propenyl and cyclohexenyl; arylalkyl groups, such as benzyl, phenylethyl and phenylpropyl; and aryl groups, such as phenyl, tolyl, dimethylphenyl, trimethylphenyl, ethylphenyl, propylphenyl, biphenyl, naphthyl, methylnaphthyl, anthracenyl and phenanthryl.

Examples of the halogenated hydrocarbon groups include the above-exemplified hydrocarbon groups which are substituted with halogen atoms.

Examples of the silicon-containing groups include monohydrocarbon-substituted silyls, such as methylsilyl and phenylsilyl; dihydrocarbon-substituted silyls, such as dimethylsilyl and diphenylsilyl; trihydrocarbon-substituted silyls, such as trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl; silyl ethers of hydrocarbon-substituted silyls, such as trimethylsilyl ether; silicon-substituted alkyl groups, such as trimethylsilylmethyl; and silicon-substituted aryl groups, such as trimethylsililphenyl.

Examples of the oxygen-containing groups include hydroxy groups; alkoxy groups, such as methoxy, ethoxy, propoxy and butoxy; aryloxy groups, such as phenoxy, methylphenoxy, dimethylphenoxy and naphthoxy; and arylalkoxy groups, such as phenylmethoxy and phenylethoxy.

Examples of the sulfur-containing groups include those wherein oxygen is replaced with sulfur in the above-exemplified oxygen-containing group.

Examples of the nitrogen-containing groups include amino group; alkylamino groups, such as methylamino, dimethylamino, diethylamino, dipropylamino, dibutylamino and dicyclohexylamino; and arylamino or alkylarylamino groups, such as phenylamino, diphenylamino, ditolylamino, dinaphthylamino and methylphenylamino.

Examples of the phosphorus-containing groups include phosphino groups, such as dimethylphosphino and diphenylphosphino.

Of these, $R^1$ is preferably a hydrocarbon group, particularly preferably a hydrocarbon group of 1 to 3 carbon atoms (methyl, ethyl or propyl). $R^2$ is preferably hydrogen or a hydrocarbon group, particularly preferably hydrogen or a hydrocarbon group of 1 to 3 carbon atoms (methyl, ethyl or propyl).

$R^3$, $R^4$, $R^5$ and $R^6$ are each independently hydrogen, a halogen atom, a hydrocarbon group of 1 to 20 carbon atoms or a halogenated hydrocarbon group of 1 to 20 carbon atoms. Of these, preferred is hydrogen, the hydrocarbon group or the halogenated hydrocarbon group. At least one combination of $R^3$ and $R^4$, $R^4$ and $R^5$, or $R^5$ and $R^6$ may form together with the carbon atoms to which they are bonded a monocyclic aromatic ring.

When there are two or more hydrocarbon groups or halogenated hydrocarbon groups, excluding the groups for forming the aromatic ring, they may be bonded to each other to form a ring. When $R^6$ is a substituent other than the aromatic group, it is preferably hydrogen.

Examples of the halogen atoms, the hydrocarbon groups of 1 to 20 carbon atoms and the halogenated hydrocarbon groups of 1 to 20 carbon atoms are those described for $R^1$ and $R^2$.

As the ligand which contains a monocyclic aromatic ring formed by at least one combination of $R^3$ and $R^4$, $R^4$ and $R^5$, or $R^5$ and $R^6$, as mentioned above, and is coordinated to M, there can be mentioned the following ones.

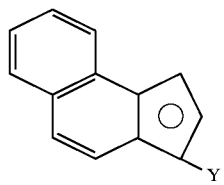

(1)

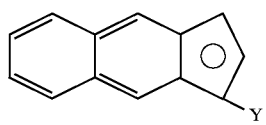

(2)

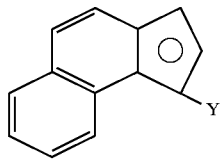

(3)

Of these, preferred is the ligand represented by the formula (1).

The aromatic ring mentioned above may be substituted with a halogen atom, a hydrocarbon group of 1 to 20 carbon atoms or a halogenated hydrocarbon group of 1 to 20 carbon atoms.

Examples of the halogen atoms, the hydrocarbon groups of 1 to 20 carbon atoms and the halogenated hydrocarbon groups of 1 to 20 carbon atoms for substituting the aromatic ring are those described for $R^1$ and $R^2$.

$X^1$ and $X^2$ are each independently hydrogen, a halogen atom, a hydrocarbon group of 1 to 20 carbon atoms, a halogenated hydrocarbon group of 1 to 20 carbon atoms, an oxygen-containing group or a sulfur-containing group.

Examples of the halogen atoms, the hydrocarbon groups of 1 to 20 carbon atoms, the halogenated hydrocarbon groups of 1 to 20 carbon atoms and the oxygen-containing groups are those described for $R^1$ and $R^2$.

Examples of the sulfur-containing groups include those described for $R^1$ and $R^2$; and further sulfonato groups, such as methylsulfonato, trifluoromethanesulfonato, phenylsulfonato, benzylsulfonato, p-toluenesulfonato, trimethylbenzenesulfonato, triisobutylbenzenesulfonato, p-chlorobenzenesulfonato and pentafluorobenzenesulfonato; and sulfinato groups, such as methylsulfinato, phenylsulfinato, benzylsulfinato, p-toluenesulfinato, trimethylbenzenesulfinato and pentafluorobenzenesulfinato.

Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^7$—, —P(R$^7$)—, —P(O) (R$^7$)—, —BR$^7$— or —AlR$^7$—, where R$^7$ is hydrogen, a halogen atom, a hydrocarbon group of 1 to 20 carbon atoms or a halogenated hydrocarbon group of 1 to 20 carbon atoms.

Examples of the divalent hydrocarbon groups of 1 to 20 carbon atoms include alkylene groups, such as methylene, dimethylmethylene, 1,2-ethylene, dimethyl-1,2-ethylene, 1,3-trimethylene, 1,4-tetramethylene, 1,2-cyclohexylene and 1,4-cyclohexylene, and arylalkylene groups, such as diphenylmethylene and diphenyl-1,2-ethylene.

Examples of the divalent halogenated hydrocarbon groups include the above-mentioned divalent hydrocarbon groups of 1 to 20 carbon atoms, which are halogenated, such as chloromethylene.

Examples of the divalent silicon-containing groups include alkylsilylene, alkylarylsilylene and arylsilylene groups, such as methylsilylene, dimethylsilylene, diethylsilylene, di(n-propyl)silylene, di(i-propyl)silylene, di(cyclohexyl)silylene, methylphenylsilylene, diphenylsilylene and di(p-tolyl)silylene; and alkyldisilylene, alkylaryldisilylene and aryldisilylene groups, such as tetramethyl-1,2-disilylene and tetraphenyl-1,2-disilylene.

Examples of the divalent germanium-containing groups include those wherein silicon is replaced with germanium in the above-mentioned divalent silicon-containing groups.

Examples of the divalent tin-containing groups include those wherein silicon is replaced with tin in the above-mentioned divalent silicon-containing groups.

R$^7$ is a halogen atom, a hydrocarbon group of 1 to 20 carbon atoms or a halogenated hydrocarbon group of 1 to 20 carbon atoms, examples of which are -hose described for R$^1$ and R$^2$.

Of the above groups, preferred are divalent silicon-containing groups, divalent germanium-containing groups and divalent tin-containing group, and more preferred are divalent silicon-containing groups. Of these, particularly preferred are alkylsilylene, alkylarylsilylene and arylsilylene.

Listed below are examples of the transition metal compounds represented by the formula (B).

| R$^1$ | R$^2$ | R$^5$ | R$^6$ | R$^8$ | R$^9$ | R$^{10}$ | R$^{11}$ | Y | X$^1$ | X$^2$ | M |
|---|---|---|---|---|---|---|---|---|---|---|---|
| H | H | H | H | H | H | H | H | SiMe$_2$ | Cl | Cl | Zr |
| CH$_3$ | H | H | H | H | H | H | H | SiMe$_2$ | Cl | Cl | Zr |
| CH$_3$ | H | H | H | H | H | H | H | SiMePh | Cl | Cl | Zr |
| CH$_3$ | H | H | H | H | H | H | H | SiPh$_2$ | Cl | Cl | Zr |
| CH$_3$ | H | H | H | H | H | H | H | Si(pMePh)$_2$ | Cl | Cl | Zr |
| CH$_3$ | H | H | H | H | H | H | H | Si(pClPh)$_2$ | Cl | Cl | Zr |
| CH$_3$ | H | H | H | H | H | H | H | C$_2$H$_4$ | Cl | Cl | Zr |
| CH$_3$ | H | H | H | H | H | H | H | GeMe$_2$ | Cl | Cl | Zr |
| CH$_3$ | H | H | H | H | H | H | H | SnMe$_2$ | Cl | Cl | Zr |
| CH$_3$ | H | H | H | H | H | H | H | SiMe$_2$ | Br | Br | Zr |
| CH$_3$ | H | H | H | H | H | H | H | SiMe$_2$ | Cl | OSO$_2$CH$_3$ | Zr |
| CH$_3$ | H | H | H | H | H | H | H | SiMe$_2$ | Cl | SO$_2$CH$_3$ | Zr |
| CH$_3$ | H | H | H | H | H | H | H | SiMe$_2$ | Cl | Cl | Ti |
| CH$_3$ | H | H | H | H | H | H | H | SiMe$_2$ | Cl | Cl | Hf |
| C$_2$H$_5$ | H | H | H | H | H | H | H | SiMe$_2$ | Cl | Cl | Zr |
| nC$_3$H$_7$ | H | H | H | H | H | H | H | SiMe$_2$ | Cl | Cl | Zr |
| C$_6$H$_5$ | H | H | H | H | H | H | H | SiMe$_2$ | Cl | Cl | Zr |
| CH$_3$ | CH$_3$ | H | H | H | H | H | H | SiMe$_2$ | Cl | Cl | Zr |
| CH$_3$ | CH$_3$ | H | H | H | H | H | H | SiPh$_2$ | Cl | Cl | Zr |
| CH$_3$ | CH$_3$ | CH$_3$ | H | H | H | H | H | SiMe$_2$ | Cl | Cl | Zr |
| CH$_3$ | H | Cl | H | H | H | H | H | SiMe$_2$ | Cl | Cl | Zr |
| CH$_3$ | H | CH$_3$ | H | H | H | H | H | SiMe$_2$ | Cl | Cl | Zr |
| CH$_3$ | H | C$_2$H$_5$ | H | H | H | H | H | SiMe$_2$ | Cl | Cl | Zr |
| CH$_3$ | H | C$_6$H$_5$ | H | H | H | H | H | SiMe$_2$ | Cl | Cl | Zr |
| CH$_3$ | H | H | CH$_3$ | H | H | H | H | SiMe$_2$ | Cl | Cl | Zr |
| CH$_3$ | H | CH$_3$ | CH$_3$ | H | H | H | H | SiMe$_2$ | Cl | Cl | Zr |
| CH$_3$ | H | CH$_2$*$^1$ | CH$_3$ | H | H | H | CH$_2$*$^1$ | SiMe$_2$ | Cl | Cl | Zr |
| CH$_3$ | H | H | H | H | H | H | C$_6$H$_5$ | SiMe$_2$ | Cl | Cl | Zr |

-continued

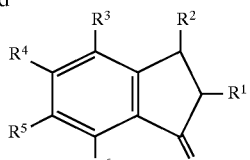

| R¹ | R² | R³ | R⁶ | R¹² | R¹³ | R¹⁴ | R¹⁵ | Y | X¹ | X² | M |
|---|---|---|---|---|---|---|---|---|---|---|---|
| H | H | H | H | H | H | H | H | SiMe₂ | Cl | Cl | Zr |
| CH₃ | H | H | H | H | H | H | H | SiMe₂ | Cl | Cl | Zr |
| CH₃ | H | H | H | H | H | H | H | SiPh₂ | Cl | Cl | Zr |
| CH₃ | CH₃ | H | H | H | H | H | H | SiMe₂ | Cl | Cl | Zr |
| CH₃ | H | CH₃ | H | H | H | H | H | SiMe₂ | Cl | Cl | Zr |
| CH₃ | H | CH₃ | CH₃ | H | H | H | H | SiMe₂ | Cl | Cl | Zr |
| CH₃ | H | CH₂*² | CH₂*² | CH₂*² | H | H | CH₂*² | SiMe₂ | Cl | Cl | Zr |
| CH₃ | H | CH₃ | CH₃ | CH₃ | H | H | CH₃ | SiMe₂ | Cl | Cl | Zr |

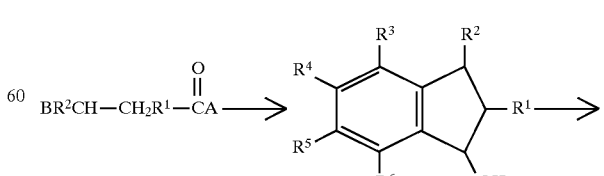

| R¹ | R² | R³ | R⁴ | Y | X¹ | X² | M |
|---|---|---|---|---|---|---|---|
| H | H | H | H | SiMe₂ | Cl | Cl | Zr |
| H | CH₃ | H | H | SiMe₂ | Cl | Cl | Zr |
| H | CH₃ | H | CH₃ | SiMe₂ | Cl | Cl | Zr |
| H | CH₃ | CH₃ | CH₃ | SiMe₂ | Cl | Cl | Zr |
| CH₃ | CH₃ | H | H | SiMe₂ | Cl | Cl | Zr |
| CH₃ | CH₃ | H | CH₃ | SiMe₂ | Cl | Cl | Zr |
| CH₃ | CH₃ | CH₃ | CH₃ | SiMe₂ | Cl | Cl | Zr |

*¹: R⁵ and R¹¹ are bonded to each other to form a five-membered ring.
*²: R³ and R¹², and R⁶ and R¹⁵ are bonded to each other to form a five-membered ring, respectively.
Me: methyl; Et: ethyl; Ph: phenyl.

Also employable in the invention are transition metal compounds wherein zirconium is replaced with titanium or hafnium in the above-mentioned compounds.

The transition metal compounds mentioned above are used generally in the form of racemic modification as the olefin polymerization catalyst component, but they can be used also in the form of R type or S type.

The indene derivative ligands for the transition metal compounds can be synthesized in accordance with ordinary organic synthesis through, for example, the reaction route described below.

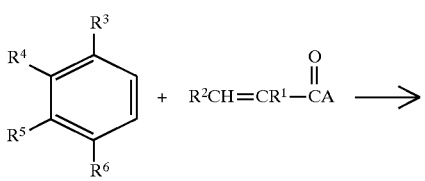

-continued

or $$R^2CH=CR^1COCCR^1=CHR^2$$

or

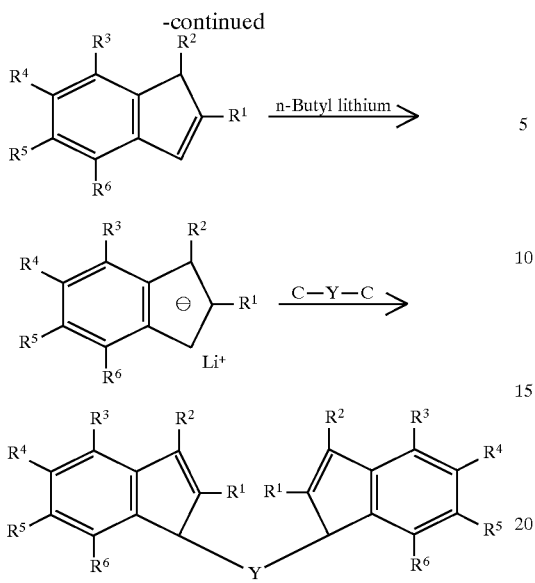

wherein A, B, and C are each a halogen atom.

The transition metal compounds used in the invention can be synthesized from these indene derivatives in accordance with conventionally known processes, for example, described in Japanese Patent Laid-Open Publication No. 268307/1992.

In the present invention, a transition metal compound (metallocene compound) represented by the following formula (C) is also employable.

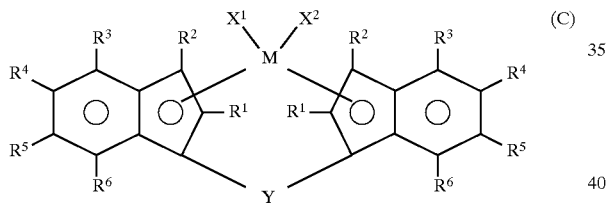

In the formula (C), M, $R^1$, $R^2$, $R^3$, $R^4$, $R^5$ and $R^6$ have the same meanings described for those in the aforesaid formula (B).

Of $R^3$, $R^4$, $R^5$ and $R^6$, at least two groups including $R^3$ are preferably alkyl groups, and it is more preferred that $R^3$ and $R^5$, or $R^3$ and $R^6$ are alkyl groups. These alkyl groups are preferably secondary or tertiary alkyl groups, and may be substituted with halogen atoms or silicon-containing groups. As the halogen atoms and the silicon-containing groups, there can be mentioned those substituents as described for $R^1$ and $R^2$.

Of the groups $R^3$, $R^4$, $R^5$ and $R^6$, other groups than the alkyl groups are each preferably hydrogen.

Examples of the hydrocarbon groups of 1 to 20 carbon atoms include straight chain and branched chain alkyl groups and cyclic alkyl groups, such as methyl, ethyl, n-propyl, i-propyl, n-butyl, sec-butyl, tert-butyl, pentyl, hexyl, cyclohexyl, heptyl, octyl, nonyl, dodecyl, eicosyl, norbornyl and adamantyl; and arylalkyl groups, such as benzyl, phenylethyl, phenylpropyl and tolylmethyl. These groups may contain a double bond or a triple bond.

Two groups selected from $R^3$, $R^4$, $R^5$ and $R^6$ may be bonded to each other to form a monocyclic or polycyclic hydrocarbon ring other than the aromatic ring.

Examples of the halogen atoms are those described for $R^1$ and $R^2$.

$X^1$, $X^2$, Y and $R^7$ have the same meanings described for those in the aforesaid formula (B).

Listed below are examples of the metallocene compounds (transition metal compounds) represented by the formula (C).

rac-Dimethylsilylene-bis(4,7-dimethyl-1-indenyl) zirconium dichloride, rac-Dimethylsilylene-bis(2,4,7-trimethyl-1-indenyl) zirconium dichloride, rac-Dimethylsilylene-bis(2,4,6-trimethyl-1-indenyl) zirconium dichloride, rac-Dimethylsilylene-bis(2,5,6-trimethyl-1-indenyl) zirconium dichloride, rac-Dimethylsilylene-bis(2,4,5,6-tetramethyl-1-indenyl) zirconium dichloride, rac-Dimethylsilylene-bis(2,4,5,6,7-pentamethyl-1-indenyl)zirconium dichloride, rac-Dimethylsilylene-bis(2-methyl-4-n-propyl-7-methyl-1-indenyl)zirconium dichloride, rac-Dimethylsilylene-bis(4-i-propyl-7-methyl-1-indenyl) zirconium dichloride, rac-Dimethylsilylene-bis(2-methyl-4-i-propyl-7-methyl-1-indenyl)zirconium dichloride, rac-Dimethylsilylene-bis(2-methyl-4-i-propyl-6-methyl-1-indenyl)zirconium dichloride, rac-Dimethylsilylene-bis(2-methyl-4-methyl-6-i-propyl-1-indenyl)zirconium dichloride, rac-Dimethylsilylene-bis(2-methyl-4-i-propyl-5-methyl-1-indenyl)zirconium dichloride, rac-Dimethylsilylene-bis(2-methyl-4,6-di(i-propyl)-1-indenyl)zirconium dichloride, rac-Dimethylsilylene-bis(2-methyl-4,6-di(i-propyl)-7-methyl-1-indenyl)zirconium dichloride, rac-Dimethylsilylene-bis(2-methyl-4-i-butyl-7-methyl-1-indenyl)zirconium dichloride, rac-Dimethylsilylene-bis(2-methyl-4-sec-butyl-7-methyl-1-indenyl)zirconium dichloride, rac-Dimethylsilylene-bis(2-methyl-4,6-di(sec-butyl)-1-indenyl)zirconium dichloride, rac-Dimethylsilylene-bis(2-methyl-4-tert-butyl-7-methyl-1-indenyl)zirconium dichloride, rac-Dimethylsilylene-bis(2-methyl-4-cyclohexyl-7-methyl-1-indenyl)zirconium dichloride, rac-Dimethylsilylene-bis(2-methyl-4-benzyl-7-methyl-1-indenyl)zirconium dichloride, rac-Dimethylsilylene-bis(2-methyl-4-phenylethyl-7-methyl-1-indenyl)zirconium dichloride, rac-Dimethylsilylene-bis(2-methyl-4-phenyldichloromethyl-7-methyl-1-indenyl)zirconium dichloride, rac-Dimethylsilylene-bis(2-methyl-4-chloromethyl-7-methyl-1-indenyl)zirconium dichloride, rac-Dimethylsilylene-bis(2-methyl-4-trimethylsilylmethyl-7-methyl-1-indenyl)zirconium dichloride, rac-Dimethylsilylene-bis(2-methyl-4-trimethylsiloxymethyl-7-methyl-1-indenyl)zirconium dichloride, rac-Diethylsilylene-bis(2-methyl-4-i-propyl-7-methyl-1-indenyl)zirconium dichloride, rac-Di(i-propyl)silylene-bis(2-methyl-4-i-propyl-7-methyl-1-indenyl)zirconium dichloride, rac-Di(n-butyl)silylene-bis(2-methyl-4-i-propyl-7-methyl-1-indenyl)zirconium dichloride,
rac-Di(cyclohexyl)silylene-bis(2-methyl-4-i-propyl-7-25 methyl-1-indenyl)zirconium dichloride,
rac-Methylphenylsilylene-bis(2-methyl-4-i-propyl-7-methyl-1-indenyl)zirconium dichloride,
rac-Diphenylsilylene-bis(2-methyl-4-i-propyl-7-methyl-1-indenyl)zirconium dichloride,
rac-Diphenylsilylene-bis(2-methyl-4,6-di(i-propyl)-1-indenyl)zirconium dichloride,
rac-Di(p-tolyl)silylene-bis(2-methyl-4-i-propyl-7-methyl-1-indenyl)zirconium dichloride,
rac-Di(p-chlorophenyl)silylene-bis(2-methyl-4-i-propyl-7-methyl-1-indenyl)zirconium dichloride,
rac-Dimethylsilylene-bis(2-methyl-4-i-propyl-7-methyl-1-indenyl)zirconium dibromide,
rac-Dimethylsilylene-bis(2-methyl-4-i-propyl-7-methyl-1-indenyl)zirconium dimethyl,
rac-Dimethylsilylene-bis(2-methyl-4-i-propyl-7-methyl-1-indenyl)zirconium methylchloride,
rac-Dimethylsilylene-bis(2-methyl-4-i-propyl-7-methyl-1-indenyl)zirconium-bis(methanesulfonato),
rac-Dimethylsilylene-bis(2-methyl-4-i-propyl-7-methyl-1-indenyl)zirconium-bis(p-phenylsulfinato),
rac-Dimethylsilylene-bis(2-methyl-3-methyl-4-i-propyl-6-methyl-1-indenyl)zirconium dichloride,
rac-Dimethylsilylene-bis(2-ethyl-4-i-propyl-6-methyl-1-indenyl)zirconium dichloride, and
rac-Dimethylsilylene-bis(2-phenyl-4-i-propyl-6-methyl-1-indenyl)zirconium dichloride.

Also employable in the invention are transition metal compounds wherein zirconium is replaced with titanium metal or hafnium in the above-mentioned compounds.

The transition metal compounds mentioned above are used generally in the form of racemic modification, but they can be used also in the form of R type or S type.

The indene derivative ligands for the transition metal compounds can be synthesized in accordance with ordinary organic synthesis through, for example, the aforementioned reaction route.

The transition metal compounds (metallocene compounds) represented by the formula (C) can be synthesized from these indene derivatives in accordance with conventionally known processes, for example, described in Japanese Patent Laid-Open Publication No. 268307/1992.

In the present invention, a transition metal compound (metallocene compound) represented by the following formula (D) is also employable.

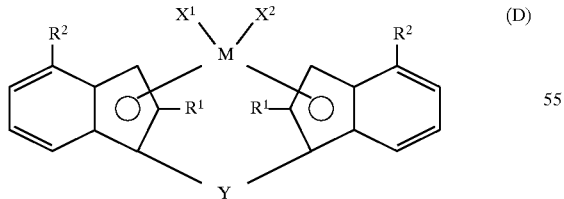

In the formula (D), M, $R^1$, $X^1$, $X^2$ and Y have the same meanings as described for those in the aforesaid formula (B) or (C).

$R^1$ is preferably a hydrocarbon group, more preferably a hydrocarbon group of 1 to 4 carbon atoms, e.g., methyl, ethyl, propyl and butyl.

$X^1$ and $X^2$ are each preferably a halogen atom or a hydrocarbon group of 1 to 20 carbon atoms.

$R^2$ is an aryl group of 6 to 16 carbon atoms, for example, phenyl, (α-naphthyl, β-naphthyl, anthracenyl, phenanthryl, pyrenyl, acenaphthyl, perinaphthenyl or aceanthrylenyl. Of these, phenyl or naphthyl is preferred. These aryl groups may be substituted with halogen atoms, hydrocarbon groups of 1 to 20 carbon atoms or halogenated hydrocarbon groups of 1 to 20 carbon atoms such as described for $R^1$.

Listed below are examples of the transition metal compounds (metallocene compounds) represented by the formula (D).

rac-Dimethylsilylene-bis(4-phenyl-1-indenyl)zirconium dichloride,
rac-Dimethylsilylene-bis(2-methyl-4-phenyl-1-indenyl)zirconium dichloride,
rac-Dimethylsilylene-bis(2-methyl-4-(α-naphthyl)-1-indenyl)zirconium dichloride,
rac-Dimethylsilylene-bis(2-methyl-4-(β-naphthyl)-1-indenyl)zirconium dichloride,
rac-Dimethylsilylene-bis(2-methyl-4-(1-anthracenyl)-1-indenyl)zirconium dichloride,
rac-Dimethylsilylene-bis(2-methyl-4-(2-anthracenyl)-1-indenyl)zirconium dichloride,
rac-Dimethylsilylene-bis(2-methyl-4-(9-anthracenyl)-1-indenyl)zirconium dichloride,
rac-Dimethylsiiylene-bis(2-methyl-4-(9-phenanthryl)-1-indenyl)zirconium dichloride,
rac-Dimethylsilylene-bis(2-methyl-4-(p-fluorophenyl)-1-indenyl)zirconium dichloride,
rac-Dimethylsilylene-bis(2-methyl-4-(pentafluorophenyl)-1-indenyl)zirconium dichloride,
rac-Dimethylsilylene-bis(2-methyl-4-(p-chlorophenyl)-1-indenyl)zirconium dichloride,
rac-Dimethylsilylene-bis(2-methyl-4-(m-chlorophenyl)-1-indenyl)zirconium dichloride,
rac-Dimethylsilylene-bis(2-methyl-4-(o-chlorophenyl)-1-indenyl)zirconium dichloride,
rac-Dimethylsilylene-bis(2-methyl-4-(o,p-dichlorophenyl)phenyl-1-indenyl)zirconium dichloride,
rac-Dimethylsilylene-bis(2-methyl-4-(p-bromophenyl)-1-indenyl)zirconium dichloride,
rac-Dimethylsilylene-bis(2-methyl-4-(p-tolyl)-1-indenyl)zirconium dichloride,
rac-Dimethylsilylene-bis(2-methyl-4-(m-tolyl)-1-indenyl)zirconium dichloride,
rac-Dimethylsilylene-bis(2-methyl-4-(o-tolyl)-1-indenyl)zirconium dichloride,
rac-Dimethylsilylene-bis(2-methyl-4-(o,o'-dimethylphenyl)-1-indenyl)zirconium dichloride,
rac-Dimethylsilylene-bis(2-methyl-4-(o-ethylphenyl)-1-indenyl)zirconium dichloride,
rac-Dimethylsilylene-bis(2-methyl-4-(p-i-propylphenyl)-1-indenyl)zirconium dichloride,
rac-Dimethylsilylene-bis(2-methyl-4-(p-benzylphenyl)-1-indenyl)zirconium dichloride,
rac-Dimethylsilylene-bis(2-methyl-4-(p-biphenyl)-1-indenyl)zirconium dichloride,
rac-Dimethylsilylene-bis(2-methyl-4-(m-biphenyl)-1-indenyl)zirconium dichloride,
rac-Dimethylsilylene-bis(2-methyl-4-(p-trimethylsilylphenyl)-1-indenyl)zirconium dichloride,
rac-Dimethylsilylene-bis(2-methyl-4-(m-trimethylsilylphenyl)-1-indenyl)zirconium dichloride, rac-Dimethylsilylene-bis(2-ethyl-4-phenyl-1-indenyl) zirconium dichloride,
rac-Diphenylsilylene-bis(2-ethyl-4-phenyl-1-indenyl) zirconium dichloride,
rac-Dimethylsilylene-bis(2-phenyl-4-phenyl-1-indenyl) zirconium dichloride,
rac-Dimethylsilylene-bis(2-n-propyl-4-phenyl-1-indenyl) zirconium dichloride,
rac-Diethylsilylene-bis(2-methyl-4-phenyl-1-indenyl) zirconium dichloride,
rac-Di-(i-propyl)silylene-bis(2-methyl-4-phenyl-1-indenyl)zirconium dichloride,
rac-Di-(n-butyl)silylene-bis(2-methyl-4-phenyl-1-indenyl)zirconium dichloride,
rac-Dicyclohexylsilylene-bis(2-methyl-4-phenyl-1-indenyl)zirconium dichloride,
rac-Methylphenylsilylene-bis(2-methyl-4-phenyl-1-indenyl)zirconium dichloride,
rac-Diphenylsilylene-bis(2-methyl-4-phenyl-1-indenyl) zirconium dichloride,
rac-Di(p-tolyl)silylene-bis(2-methyl-4-phenyl-1-indenyl) zirconium dichloride,
rac-Di(p-chlorophenyl)silylene-bis(2-methyl-4-phenyl-1-indenyl)zirconium dichloride,
rac-Methylene-bis(2-methyl-4-phenyl-1-indenyl) zirconium dichloride,
rac-Ethylene-bis(2-methyl-4-phenyl-1-indenyl)zirconium dichloride,
rac-Dimethylgermylene-bis(2-methyl-4-phenyl-1-indenyl)zirconium dichloride,
rac-Dimethylstannylene-bis(2-methyl-4-phenyl-1-indenyl)zirconium dichloride,
rac-Dimethylsilylene-bis(2-methyl-4-phenyl-1-indenyl) zirconium dibromide,
rac-Dimethylsilylene-bis(2-methyl-4-phenyl-1-indenyl) zirconium dimethyl,
rac-Dimethylsilylene-bis(2-methyl-4-phenyl-1-indenyl) zirconium methylchloride,
rac-Dimethylsilylene-bis(2-methyl-4-phenyl-1-indenyl) zirconium chloride $SO_2Me$, and
rac-Dimethylsilylene-bis(2-methyl-4-phenyl-1-indenyl) zirconium chloride $OSO_2Me$.

Also employable in the invention are transition metal compounds wherein zirconium is replaced with titanium or hafnium in the above-mentioned compounds.

The transition metal compounds represented by the formula (D) can be prepared in accordance with "Journal of Organometallic Chem.", 288(1985), pp. 63–67, and European Patent Publication No. 0,320,762 (specification and examples), for example, in the following manner.

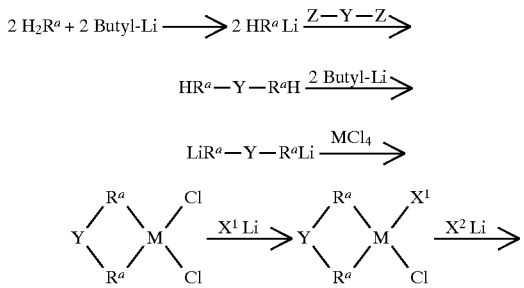

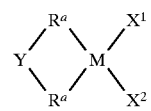

wherein Z is Cl, Br, I or o-tosyl,

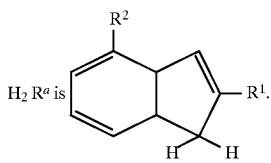

The transition metal compounds (D) are used generally in the form of racemic modification, but they can be used also in the form of R type or S type.

In the present invention, a compound represented by the following formula (E-1) can be also employed as the metallocene compound.

$$L^a MX_2 \qquad \text{(E-1)}$$

wherein, M is a metal of Group IV of the periodic table or a metal of lanthanide series;

$L^a$ is a derivative of delocalization π bond group and imparts restraint geometrical shape to the metal M active site; and the X's are each independently hydrogen, halogen, a hydrocarbon group of 20 or less carbon, silicon or germanium atoms, a silyl group or a germyl group.

Of the compounds of the formula (E-1), preferred are compounds represented by the following formula (E-2).

wherein M is titanium, zirconium or hafnium; X is the same as described above;

Cp is a substituted cyclopentadienyl group which is π bonded to M and has a substituent Z;

Z is oxygen, sulfur, boron or an element of Group IVA of the periodic table (e.g., silicon, germanium or tin);

Y is a ligand containing nitrogen, phosphorus, oxygen or sulfur; and

Z and Y may together form a condensed ring.

Listed below are examples of the compounds represented by the formula (E-2).

(Dimethyl(t-butylamide)(tetramethyl-$\eta^5$-cyclopentadienyl)silane)titanium dichloride, ((t-Butylamide) (tetramethyl-$\eta^5$-cyclopentadienyl) -1,2-ethanediyl)titanium dichloride, (Dibenzyl(t-butylamide)(tetramethyl-$\eta^5$-cyclopentadienyl)silane)titanium dichloride, (Dimethyl(t-butylamide)(tetramethyl-$\eta^5$-cyclopentadienyl)silane)dibenzyltitanium, (Dimethyl(t-butylamide)(tetramethyl-$\eta^5$-cyclopentadienyl)silane)dimethyltitanium, ((t-Butylamide) (tetramethyl-$\eta^5$-cyclopentadienyl)-1,2-ethanediyl)dibenzyltitanium, ((Methylamide)(tetramethyl-$\eta^5$-cyclopentadienyl)-1,2-ethanediyl)dineopentyltitanium, ((Phenylphosphide)(tetramethyl-$\eta^5$-cyclopentadienyl)-methylene)diphenyltitanium, (Dibenzyl(t-butylamide) (tetramethyl-$\eta^5$-cyclopentadienyl)silane)dibenzyltitanium, (Dimethyl(benzylamide)($\eta^5$-cyclopentadienyl)silane)di(trimethylsilyl)titanium, (Dimethyl(phenylphosphide)-(tetramethyl-$\eta^5$-cyclopentadienyl)silane)dibenzyltitanium, (Tetramethyl-$\eta^5$-cyclopentadienyl)-1,2-ethanediyl)dibenzyltitanium, (2-$\eta^5$-(Tetramethyl-cyclopentadienyl)-1-methyl-ethanolate(2-))dibenzyltitanium, (2-$\eta^5$-(Tetramethyl-cyclopentadienyl)-1-methyl-ethanolate(2-))dimethyltitanium, (2-((4a,4b,8a,9,9a-$\eta$)-9H-fluorene-9-yl)cyclohexanolate(2-))dimethyltitanium, and (2-((4a,4b,8a,9,9a-$\eta$)-9H-fluorene-9-yl)cyclohexanolate(2-))dibenzyltitanium.

In the present invention, the metallocene compounds mentioned above can be used in combination of two or more kinds.

Some examples of titanium compounds are mentioned above as the metallocene compounds, but compounds wherein titanium is replaced with zirconium or hafnium in the above-mentioned titanium compounds can be also exemplified.

Those compounds may be used alone or in combination of two or more kinds.

As the metallocene compounds (E-1) and (E-2), zirconocene compounds which have zirconium as the central metal atom and have at least two ligands containing a cyclopentadienyl skeleton. In the metallocene compounds, the central metal atom is preferably titanium.

The metallocene compounds may be used by diluting with hydrocarbons or halogenated hydrocarbons.

The metallocene compounds may be used by contacting with the particulate carrier compounds.

As the carrier compounds, there can be used inorganic carrier compounds such as $SiO_2$, $Al_2O_3$, $B_2O_3$, MgO, $ZrO_2$, CaO, $TiO_2$, ZnO, $SnO_2$, BaO and ThO; and resins such as polyethylene, polypropylene, poly-1-butene, poly-4-methyl-1-pentene and styrene-divinylbenzene copolymer. These carrier compounds may be used in combination of two or more kinds.

Next, the organoaluminum oxy-compound and the ionized ionic compound used for forming the catalyst (b) (catalyst comprising a metallocene compound of a transition metal selected from elements of Group IV of the periodic table, and an organoaluminum oxy compound or an ionized ionic compound) are described.

The organoaluminum oxy-compound used in the invention may be either aluminoxane conventionally known or a benzene-insoluble organoaluminum oxy-compound.

The conventionally known aluminoxane is represented by the following formula (1) or (2).

(1)

(2)

wherein R is a hydrocarbon group such as methyl, ethyl, propyl and butyl, preferably methyl or ethyl, particularly preferably methyl, and m is an integer of not less than 2, preferably an integer of 5 to 40.

This aluminoxane may be formed from mixed alkyloxy-aluminum units consisting of alkyloxyaluminum units represented by the formula ($OAl(R^1)$) and alkyloxyaluminum units represented by the formula ($OAl(R^2)$) (in these formulas, $R^1$ and $R^2$ are each the same hydrocarbon group as described for R, and $R^1$ and $R^2$ are different from each other).

The conventionally known aluminoxane can be prepared by, for example, the following procedures, and the aluminoxane is generally recovered in the form of an aromatic hydrocarbon solvent solution.

(1) An organoaluminum compound such as trialkylaluminum is added to a hydrocarbon solvent suspension of compounds containing adsorbed water or salts containing water of crystallization, e.g., magnesium chloride hydrate, copper sulfate hydrate, aluminum sulfate hydrate, nickel sulfate hydrate and cerous chloride hydrate, so as to allow the organoaluminum compound to react with the adsorbed water or the water of crystallization, and the reaction product is recovered as an aromatic hydrocarbon solvent solution.

(2) Water, ice or water vapor is allowed to directly act on an organoaluminum compound such as trialkylaluminum in a medium such as benzene, toluene, ethyl ether or tetrahydrofuran, and the reaction product is recovered as an aromatic hydrocarbon solvent solution.

Of the above procedures, the procedure (1) is preferably used.

Examples of the organoaluminum compounds used for preparing the solution of aluminoxane include the aforesaid organoaluminum compounds. More specifically, there can be mentioned:

trialkylaluminums, such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum, tridecylaluminum, tricyclohexylaluminum and tricyclooctylaluminum;

alkenylaluminums represented by the formula $(iC_4H_9)_x Al_y(C_5H_{10})_z$ (x, y and z are each a positive number, and $z \geq 2x$), such as isoprenylaluminum;

dialkylaluminum halides, such as dimethylaluminum chloride, diethylaluminum chloride, diethylaluminum bromide and diisobutylaluminum chloride;

dialkylaluminum hydrides, such as diethylaluminum hydride and diisobutylaluminurn hydride;

dialkylaluminum alkoxides, such as dimethylaluminum methoxide and diethylaluminum ethoxide; and dialkylaluminum aryloxides, such as diethylaluminum phenoxide.

Of these, preferred are trialkylaluminums.

The organoaluminum compounds mentioned above are used singly or in combination.

The benzene-insoluble organoaluminum oxy-compound used in the invention can be obtained by, for example, contacting the solution of aluminoxane with water or an active hydrogen-containing compound or contacting the organoaluminum compound with water.

In the benzene-insoluble organoaluminum oxy-compound used for the invention, a ratio of the absorbance at about 1,260 $cm^{-1}$ ($D_{1260}$) to the absorbance at about 1,220 $cm^{-1}$ ($D_{1220}$) obtained by the infrared spectroscopic analysis of the compound, ($D_{1260}/D_{1220}$), is not more than 0.09, preferably not more than 0.08, particularly preferably in the range of 0.04 to 0.07.

The benzene-insoluble organoaluminum oxy-compound is presumed to have alkyloxyaluminum units represented by the following formula:

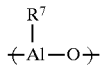

wherein $R^7$ is a hydrocarbon group of 1 to 12 carbon atoms. Examples of such hydrocarbon groups include methyl, ethyl, n-propyl, isopropyl, n-butyl, isobutyl, pentyl, hexyl, octyl, decyl, cyclohexyl and cyclooctyl. Of these, preferred are methyl and ethyl, and particularly preferred is methyl.

This benzene-insoluble organoaluminum oxy-compound may have, in addition to the alkyloxyaluminum units represented by the above formula, oxyaluminum units represented by the following formula:

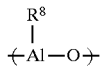

wherein $R^8$ is a hydrocarbon group of 1 to 12 carbon atoms, an alkoxy group of 1 to 12 carbon atoms, an aryloxy group of 6 to 20 carbon atoms, a hydroxyl group, halogen or hydrogen.

$R^8$ is different from $R^7$ in the aforesaid formula.

When the organoaluminum oxy-compound contains the oxyaluminum units, it is desired that the alkyloxyaluminum units are contained in an amount of not less than 30% by mol, preferably not less than 50% by mol, particularly preferably not less than 70% by mol.

The organoaluminum oxy-compound used in the invention may contain a small amount of an organic compound component of other metal than aluminum.

The ionized ionic compound used in the present invention includes Lewis acids, ionic compounds, borane compounds and carborane compounds.

The Lewis acids include, for example, a compound represented by the formula: $BR_3$ wherein each R is independently a phenyl group which may have substituents such as fluorine, methyl and trifluoromethyl, or a fluorine atom.

Examples of the compounds represented by the above formula include trifluoroboron, triphenylboron, tris(4-fluorophenyl)boron, tris(3,5-difluorophenyl)boron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris (3,5-dimethylphenyl)boron.

Examples of the ionic compounds include trialkyl-substituted ammonium salts, N,N-dialkylanilinium salts, dialkylammonium salts and triarylphsphonium salts.

Particular examples of the trialkyl-substituted ammonium salts include:
triethylammoniumtetra(phenyl)boron,
tripropylammoniumtetra(phenyl)boron,
tri(n-butyl)ammoniumtetra(phenyl)boron,
trimethylammoniumtetra(p-tolyl)boron,
trimethylammoniumtetra(o-tolyl)boron,
tributylammoniumtetra(pentafluorophenyl)boron,
tripropylammoniumtetra(o,p-dimethylphenyl)boron,
tributylammoniumtetra(m,m-dimethylphenyl)boron,
tributylammoniumtetra(p-trifluoromethylphenyl)boron, and
tri(n-butyl)ammoniumtetra(o-tolyl)boron.

Particular examples of the N,N,-dialkylanilinium salts include:
N,N-dimethylaniliniumtetra(phenyl)boron,
N,N-diethylaniliniumtetra(phenyl)boron, and
N,N-2,4,6-pentamethylaniliniumtetra(phenyl)boron.

Particular examples of the dialkylammonium salts include:
di(1-propyl)ammoniumtetra(pentafluorophenyl)boron, and
dicyclohexylammoniumtetra(phenyl)boron.

Also employable as the ionic compound (b) are triphenylcarbeniumtetrakis(pentafluorophenyl)borate, N,N-dimethylaniliniumtetrakis(pentafluorophenyl)borate and ferroceniumtetra(pentafluorophenyl)borate.

Further, also employable as the borane compound are the following compounds:
decaborane (14);
salts of anion, such as
bis(tri(n-butyl)ammonium)nonaborate,
bis(tri(n-butyl)ammonium)decaborate,
bis(tri(n-butyl)ammonium)undecaborate,
bis(tri(n-butyl)ammonium)dodecaborate,
bis(tri(n-butyl)ammonium)decachlorodecaborate, and
bis(tri(n-butyl)ammonium)dodecachlorododecaborate; and
salts of metallic borane anion, such as
tri(n-butyl)ammonium-bis(dodecahydridedodecaborate) cobaltate (III), and
bis(tri(n-butyl)ammonium)-bis(dodecahydridedodecaborate)nickelate (III).

Further, particular examples of carborane compounds include:
salts of anion, such as
4-carbanonaborane(14),
1,3-dicarbanonaborane(13),
6,9-dicarbadecaborane(14),
dodecahydride-1-phenyl-1,3-dicarbanonaborane,
dodecahydride-1-methyl-1,3-dicarbanonaborane, and
undecahydride-1,3-dimethyl-1,3-dicarbanonaborane,
7,8-dicarbaundecaborane(13),
2,7-dicarbaundecaborane(13),
undecahydride-7,8-dimethyl-7,8-dicarbaundecaborane,
dodecahydride-11-methyl-2,7-dicarbaundecaborane,
tri(n-butyl)ammonium-1-carbadecaborate,
tri(n-butyl)ammonium-1-carbaundecaborate,
tri(n-butyl)ammonium-1-carbadodecaborate,
tri(n-butyl)ammonium-1-trimethylsilyl-1-carbadecaborate, and
tri(n-butyl)ammoniumbromo-1-carbadodecaborate,
tri(n-butyl)ammonium-6-carbadecaborate(14),
tri(n-butyl)ammonium-6-carbadecaborate(12),
tri(n-butyl)ammonium-7-carbaundecaborate(13),
tri(n-butyl)ammonium-7,8-dicarbaundecaborate(12),
tri(n-butyl)ammonium-2,9-dicarbaundecaborate(12),
tri(n-butyl)ammoniumdodecahydride-8-methyl-7,9-dicarbaundecaborate,
tri(n-butyl)ammoniumundecahydride-8-ethyl-7,9-dicarbaundecaborate,
tri(n-butyl)ammoniumundecahydride-8-butyl-7,9-dicarbaundecaborate,
tri(n-butyl)ammoniumundecahydride-8-allyl-7,9-dicarbaundecaborate, tri(n-butyl)ammoniumundecahydride-9-trimethylsilyl-7, 8-dicarbaundecaborate, and tri(n-butyl)ammoniumundecahydride-4,6-dibromo-7-carbaundecaborate; and salts of metallic carborane anion, such as:

tri(n-butyl)ammoniumbis(nonahydride-1,3-dicarbanonaborate)cobaltate(III), tri(n-butyl)ammoniumbis(undecahydride-7,8-dicarbaundecaborate)ferrate(III), tri(n-butyl)ammoniumbis(undecahydride-7,8-dicarbaundecaborate)cobaltate(III), tri(n-butyl)ammoniumbis(undecahydride-7,8-dicarbaundecaborate)nickelate(III), tri(n-butyl)ammoniumbis(undecahydride-7,8-dicarbaundecaborate)cuprate(III), tri(n-butyl)ammoniumbis(undecahydride-7,8-dicarbaundecaborate)aurate(III), tri(n-butyl)ammoniumbis(nonahydride-7,8-dimethyl-7,8-dicarbaundecaborate)ferrate(III), tri(n-butyl)ammoniumbis(nonahydride-7,8-dimethyl-7,8-dicarbaundecaborate)chromate(III), tri(n-butyl)ammoniumbis(tribromooctahydride-7,8-dicarbaundecaborate)cobaltate(III), tris(tri(n-butyl)ammonium)bis(undecahydride-7-carbaundecaborate)chromate(III), bis(tri(n-butyl)ammonium)bis(undecahydride-7-carbaundecaborate)manganate(IV), bis(tri(n-butyl)ammonium)bis(undecahydride-7-carbaundecaborate)cobaltate(III), and bis(tri(n-butyl)ammonium)bis(undecahydride-7-carbaundecaborate)nickelate(IV).

The ionized ionic compounds mentioned above may be used in combination of two or more kinds.

In the present invention, the organoaluminum oxy-compound or the ionized ionic compound may be used by supporting it on the aforementioned carrier compound.

For preparing the catalyst (b), the aforementioned organoaluminum compound may be used together with the organoaluminum oxy-compound or the ionized ionic compound.

In the present invention, (i) ethylene, (ii) the α-olefin and (iii) the nonconjugated triene or tetraene (nonconjugated polyene) are copolymerized generally in a liquid phase in the presence of the catalyst (a) (catalyst comprising the soluble vanadium compound and the organoaluminum compound) or the catalyst (b) (catalyst comprising the metallocene compound of a transition metal selected from elements of Group IV of the periodic table and the organoaluminum oxy-compound or the ionized ionic compound). In the copolymerization, a hydrocarbon solvent is usually used, but an α-olefin such as propylene may be used as a solvent.

Examples of such hydrocarbon solvents include aliphatic hydrocarbons, such as pentane, hexane, heptane, octane, decane, dodecane and kerosine, and halogenated derivatives of these aliphatic hydrocarbons;

alicyclic hydrocarbons, such as cyclohexane, methylcyclopentane and methylcyclohexane, and halogenated derivatives of these alicyclic hydrocarbons; and aromatic hydrocarbons, such as benzene, toluene and xylene, and halogenated derivatives of these hydrocarbons, such as chlorobenzene. These solvents may be used in combination.

The ethylene (i), the α-olefin (ii) and the nonconjugated polyene (iii) may be copolymerized either batchwise or continuously. When the copolymerization is carried out continuously, the catalyst is used in the following concentration.

If the catalyst (a), i.e., catalyst comprising the soluble vanadium compound and the organoaluminum compound, is used in the invention, the concentration of the soluble vanadium compound in the polymerization system is in the range of usually 0.01 to 5 mmol/liter-polymerization volume, preferably 0.05 to 3 mmol/liter. The soluble vanadium compound is desirably fed as a solution in a concentration of not more than 10 times, preferably 1 to 7 times, more preferably 1 to 5 times, as much as the concentration of the soluble vanadium compound present in the polymerization system. The organoaluminum compound is fed in a molar ratio of the aluminum atom to the vanadium atom (Al/V) in the polymerization system of not less than 2, preferably 2 to 50, more preferably 3 to 20.

The soluble vanadium compound and the organoaluminum compound are generally fed after being diluted with the hydrocarbon solvent and/or the α-olefin (ii) in a liquid form and the nonconjugated triene or tetraene (nonconjugated polyene) (iii) in a liquid form. In this case, the soluble vanadium compound is desirably diluted in the above-mentioned concentration, and the organoaluminum compound is desirably fed after controlling the concentration to an optional concentration of not more than 50 times as much as the concentration of the organoaluminum compound in the polymerization system.

If the catalyst (b), i.e., catalyst comprising the metallocene compound and the organoaluminum oxy-compound or the ionized ionic compound (also referred to as "ionic ionized compound" or "ionic compound"), is used, the concentration of the metallocene compound in the polymerization system is in the range of usually 0.00005 to 0.1 mmol/liter-polymerization volume, preferably 0.0001 to 0.05 mmol/liter. The organoaluminum oxy-compound is fed in a molar ratio of the aluminum atom to the transition metal of the metallocene compound (Al/transition metal) in the polymerization system of 1 to 10,000, preferably 10 to 5,000.

In the case of using the ionized ionic compound, this compound is fed in a molar ratio of the ionized ionic compound to the metallocene compound (ionized ionic compound/metallocene compound) in the polymerization system of 0.5 to 20, preferably 1 to 10.

In the case of using the organoaluminum compound, this compound is used in such an amount that the concentration of the organoaluminum compound in the system becomes usually about 0 to 5 mmol/liter-polymerization volume, preferably about 0 to 2 mmol/liter.

When the ethylene (i), the α-olefin (ii) and the nonconjugated polyene (iii) are copolymerized in the presence of the catalyst (a) comprising the soluble vanadium compound and the organoaluminum compound, the copolymerization reaction is carried out under the conditions of a temperature of −50° to 100° C., preferably −30° to 80° C., more preferably −20° to 60° C., and a pressure of higher than 0 kg/cm$^2$ and not higher than 50 kg/cm$^2$, preferably higher than 0 kg/cm$^2$ and not higher than 20 kg/cm$^2$.

When the ethylene (i), the α-olefin (ii) and the nonconjugated polyene (iii) are copolymerized in the presence of the catalyst (b) comprising the metallocene compound and the organoaluminum oxy-compound or the ionized ionic compound, the copolymerization reaction is carried out under the conditions of a temperature of −20° to 150° C., preferably 0° to 120° C., more preferably 0° to 100° C., and a pressure of higher than 0 kg/cm$^2$ and not higher than 80 kg/cm$^2$, preferably higher than 0 kg/cm$^2$ and not higher than 50 kg/cm$^2$.

The reaction time (which is an average residence time in case of continuous copolymerization) varies depending upon the conditions such as catalyst concentration and polymerization temperature, but it is in the range of usually 5 minutes to 5 hours, preferably 10 minutes to 3 hours.

In the present invention, the ethylene (i), the α-olefin (ii) and the nonconjugated polyene (iii) are fed to the polymerization system in such amounts that the unsaturated copolymer of ethylene having the aforementioned specific composition is obtained. In the copolymerization, a molecular weight regulator such as hydrogen is also employable.

When the ethylene (i), the α-olefin (ii) and the nonconjugated polyene (iii) are copolymerized as described above, the unsaturated copolymer of ethylene is obtained in the form of usually a polymer solution containing it. This polymer solution is treated in a conventional manner to obtain an unsaturated copolymer of ethylene. (Graft modified product of unsaturated copolymer of ethylene)

The unsaturated copolymer of ethylene according to the invention can be used by modifying it through graft polymerization of the unsaturated copolymer of ethylene with a polar monomer.

The unsaturated copolymer of ethylene having been graft modified (sometimes referred to as "graft modified unsaturated copolymer of ethylene") can be obtained by allowing the unsaturated copolymer of ethylene to react with a polar monomer described below in the presence or the absence of a radical initiator.

The polar monomer is, for example, a hydroxyl group-containing ethylenic unsaturated compound, an amino group-containing ethylenic unsaturated compound, an epoxy group-containing ethylenic unsaturated compound, an aromatic vinyl compound, an unsaturated carboxylic acid or its derivative, an vinyl ester compound or vinyl chloride.

Particular examples of the hydroxyl group-containing ethylenic unsaturated compounds include (meth)acrylates, such as hydroxyethyl (meth)acrylate, 2-hydroxypropyl (meth)acrylate, 3-hydroxypropyl (meth)acrylate, 2-hydroxy-3-phenoxypropyl (meth)acrylate, 3-chloro-2-hydroxypropyl (meth)acrylate, glycerol mono(meth)acrylate, pentaerythritol mono(meth)acrylate, trimethylolpropane mono(meth)acrylate, tetramethylolethane mono(meth)acrylate, butanediol mono(meth)acrylate, polyethylene glycol mono (meth) acrylate and 2-(6-hydroxyhexanoyloxy) ethyl acrylate; 10-undecene-1-ol, 1-octene-3-ol, 2-methanolnorbornene, hydroxystyrene, hydroxyethyl vinyl ether, hydroxybutyl vinyl ether, N-methylolacrylamide, 2-(meth)acroyloxyethyl acid phosphate, glycerol monoallyl ether, allyl alcohol, allyloxyethanol, 2-butene-1,4-diol and glycerol monoalcohol.

The amino group-containing ethylenic unsaturated compound is a compound having an ethylenic double bond and an amino group, and such compound is, for example, a vinyl monomer having at least one amino group or substituted amino group represented by the following formula:

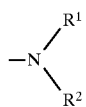

wherein $R^1$ is hydrogen, methyl or ethyl, and $R^2$ is hydrogen, an alkyl group having 1 to 12 carbon atoms (preferably 1 to 8 carbon atoms) or a cycloalkyl group having 6 to 12 carbon atoms (preferably 6 to 8 carbon atoms). The alkyl group and the cycloalkyl group may have a substituent.

Examples of the amino group-containing ethylenic unsaturated compounds include alkyl ester derivatives of acrylic acids or methacrylic acids, such as aminoethyl (meth)acrylate, propylaminoethyl (meth)acrylate, dimethylaminoethyl (meth)acrylate, aminopropyl (meth)acrylate, phenylaminoethyl methacrylate and cyclohexylaminoethyl methacrylate; vinyl amine derivatives, such as N-vinyldiethylamine and N-acetylvinylamine; allylamine derivatives, such as allylamine, methacrylamine, N-methylacrylamine, N,N-dimethylacrylamide and N,N-dimethylaminopropylacrylamide; acrylamide derivatives, such as acrylamide and N-methylacrylamide; aminostyrenes, such as p-aminostyrene; 6-aminohexylsuccinimide; and 2-aminoethylsuccinimide.

The epoxy group-containing ethylenic unsaturated compound is a monomer having at least one polymerizable unsaturated bond and at least one epoxy group in one molecule. Examples of such epoxy group-containing ethylenic unsaturated compounds include glycidyl acrylate and glycidyl methacrylate; dicarboxylic acid mono and dialkylglycidyl esters (number of carbon atoms of the alkyl group in the case of monoglycidyl ester: 1–12), such as mono and diglycidyl esters of maleic acid, mono and diglycidyl esters of fumaric acid, mono and diglycidyl esters of crotonic acid, mono and diglycidyl esters of tetrahydrophthalic acid, mono and diglycidyl esters of itaconic acid, mono and diglycidyl esters of butenetricarboxylic acid, mono and diglycidyl esters of citraconic acid, mono and diglycidyl esters of endo-cis-bicyclo[2,2,1]hepto-5-ene-2,3-dicarboxylic acid (nadic acid™), mono and diglycidyl esters of endo-cis-bicyclo[2,2,1]hepto-5-ene-2-methyl-2,3-dicarboxylic acid (methylnadic acids™), and mono and diglycidyl esters of allylsuccinic acid; alkylglycidyl esters of p-styrenecarboxylic acid, allylglycidyl ether, 2-methylallylglycidyl ether, styrene-p-glycidyl ether, 3,4-epoxy-1-butene, 3,4-epoxy-3-methyl-1-butene, 3,4-epoxy-1-pentene, 3,4-epoxy-3-methyl-1-pentene, 5,6-epoxy-1-hexene, and vinylcyclohexene monooxide.

The aromatic vinyl compound is, for example, a compound represented by the following formula:

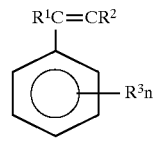

wherein $R^1$ and $R^2$ are each independently hydrogen or an alkyl group of 1 to 3 carbon atoms, such as methyl, ethyl, propyl or isopropyl, $R^3$ is a hydrocarbon group of 1 to 3 carbon atoms or a halogen atom, such as methyl, ethyl, propyl, isopropyl, chlorine, bromine or iodine, and n is usually an integer of 0 to 5, preferably an integer of 1 to 5.

Examples of such aromatic vinyl compounds include styrene, α-methylstyrene, o-methylstyrene, p-methylstyrene, m-methylstyrene, p-chlorostyrene, m-chlorostyrene, p-chloromethylstyrene. Heterocyclic aromatic vinyl compounds may also be utilized and include 4-vinylpyridine, 2-vinylpyridine, 5-ethyl-2-vinylpyridine, 2-methyl-5-vinylpyridine, 2-isopropenylpyridine, 2-vinylquinoline, 3-vinylisoquinoline, N-vinylcarbazole and N-vinylpyrrolidone.

Examples of the unsaturated carboxylic acids include unsaturated carboxylic acids, such as acrylic acid, methacrylic acid, maleic acid, fumaric acid, tetrahydrophthalic acid, itaconic acid, citraconic acid, crotonic acid, isocrotonic acid, norbornenedicarboxylic acid and bicyclo[2,2,1]hepto- 2-ene-5,6-dicarboxylic acid; acid anhydrides of these acids; and derivatives of these acids (e.g., acid halides, amides, imides and esters). Particular examples of such compounds include malenyl chloride, malenylimide, maleic anhydride, itaconic anhydride, citraconic anhydride, tetrahydrophthalic anhydride, bicyclo[2,2,1]hepto-2-ene-5,6-dicarboxylic anhydride, dimethyl maleate, monomethyl maleate, diethyl maleate, diethyl fumarate, dimethyl itaconate, diethyl citraconate, dimethyl tetrahydrophthalate, dimethyl bicyclo [2,2,1]hepto-2-ene-5,6-dicarboxylate, hydroxyethyl (meth) acrylate, hydroxypropyl (meth)acrylate, glycidyl (meth) acrylate, aminoethyl methacrylate and aminopropyl methacrylate. Of these, preferred are (meth)acrylic acid, maleic anhydride, hydroxyethyl (meth)acrylate, glycidyl methacrylate and aminopropyl methacrylate.

Examples of the vinyl ester compounds include vinyl acetate, vinyl propionate, vinyl n-butyrate, vinyl isobutyrate, vinyl pivalate, vinyl caproate, vinyl versatate, vinyl laurate, vinyl stearate, vinyl benzoate, vinyl p-t-butylbenzoate, vinyl salicylate and vinyl cyclohexanecaboxylate.

The polar monomer is used in an amount of usually 1 to 100 parts by weight, preferably 50 to 80 parts by weight, based on 100 parts by weight of the unsaturated copolymer of ethylene.

The radical initiator is, for example, an organic peroxide or an azo compound.

Examples of the organic peroxides include dicumyl peroxide, di-t-butyl peroxide, 2,5-dimethyl-2,5-bis(t-butylperoxy)hexane, 2,5-dimethyl-2,5-bis(t-butylperoxy) hexyne-3,1,3-bis(t-butylperoxyisopropyl)benzene, 1,1-bis (t-butylperoxy)valerate, benzoyl peroxide, t-butyl peroxybenzoate, acetyl peroxide, isobutyryl peroxide, octanoyl peroxide, decanoyl peroxide, lauroyl peroxide, 3,5,5-trimethylhexanoyl peroxide, 2,4-dichlorobenzoyl peroxide and m-toluyl peroxide. Examples of the azo compounds include azoisobutyronitrile and dimethylazoisobutyronitrile.

The radical initiator is desirably used in an amount of usually 0.001 to 10 parts by weight based on 100 parts by weight of the unsaturated copolymer of ethylene.

The radical initiator can be used by mixing it with the unsaturated copolymer of ethylene and the polar monomer, but it may be used after dissolving it in a small amount of an organic solvent. As the organic solvent, any organic solvents can be employed without specific limitation as far as they dissolve the radical initiator. Examples of the organic solvents include aromatic hydrocarbon solvents, such as benzene, toluene and xylene; aliphatic hydrocarbon solvents, such as pentane, hexane, heptane, octane, nonane and decane; alicyclic hydrocarbon solvents, such as cyclohexane, methylcyclohexane and decahydronaphthalene; chlorinated hydrocarbons, such as chlorobenzene, dichlorobenzene, trichlorobenzene, methylene chloride, chloroform, carbon tetrachloride and tetrahcloroethylene; alcohol solvents, such as methanol, ethanol, n-propanol, iso-propanol, n-butanol, sec-butanol and tert-butanol; ketone solvents, such as acetone, methyl ethyl ketone and methyl isobutyl ketone; ester solvents, such as ethyl acetate and dimethyl phthalate; and ether solvents, such as dimethyl ether, diethyl ether, di-n-amyl ether, tetrahydrofuran and dioxyanisole.

In the present invention, a reducing material may be used in the graft modification of the unsaturated copolymer of ethylene. The reducing material serves to enhance the graft amount in the graft modified unsaturated copolymer of ethylene obtained.

The reducing material includes not only iron(II) ion, chromium ion, cobalt ion, nickel ion, palladium ion, sulfite, hydroxylamine and hydrazine but also compounds containing groups such as —SH, $SO_3H$, —$NHNH_2$ and —COCH (OH)—.

Examples of such reducing materials include ferrous chloride, potassium bichromate, cobalt chloride, cobalt naphthenate, palladium chloride, ethanolamine, diethanolamine, N,N-dimethylaniline, hydrazine, ethylmercaptan, benzenesulfonic acid and p-toluenesulfonic acid.

The reducing material is used in an amount of usually 0.001 to 5 parts by weight, preferably 0.1 to 3 parts by weight, based on 100 parts by weight of the unsaturated copolymer of ethylene.

The graft modification of the unsaturated copolymer of ethylene can be carried out in a conventional manner. For example, the unsaturated copolymer of ethylene is dissolved in an organic solvent, and to the solution is then added the polar monomer and the radical initiator to react them at 70° to 200° C., preferably 80° to 190° C., for 0.5 to 15 hours, preferably 1 to 10 hours.

There is no specific limitation on the organic solvent used for graft modifying the unsaturated copolymer of ethylene, and any organic solvents can be used as far as they dissolve the unsaturated ethylene copolymer.

Examples of such organic solvents include aromatic hydrocarbon solvents such as benzene, toluene and xylene; and aliphatic hydrocarbon solvents such as pentane, hexane and heptane.

The unsaturated copolymer of ethylene can be reacted with the polar monomer in the absence of any solvent using an extruder or the like to prepare a graft modified unsaturated copolymer of ethylene. In this case, the reaction temperature is usually not lower than the melting point of the unsaturated copolymer of ethylene, specifically, in the range of 120° to 250° C. The reaction time under such temperature condition is usually in the range of 0.5 to 10 minutes.

In the graft modified unsaturated copolymer of ethylene thus prepared, the graft amount of the graft group derived from the polar monomer is in the range of usually 0.1 to 50% by weight, preferably 0.2 to 30% by weight.

The modified unsaturated copolymer of ethylene obtained as above is excellent in adhesion strength to metals and polar resins. Further, when the modified unsaturated copolymer of ethylene is blended with a polar resin, the polar resin can be improved in impact resistance, particularly, low-temperature impact resistance.

Furthermore, molded articles obtained from the modified unsaturated copolymer of ethylene (modified ethylene random copolymer) are excellent in printability and paintability onto the surfaces thereof. Moreover, if polyolefins are blended with the modified unsaturated copolymer of ethylene (modified ethylene random copolymer) together with fillers such as glass fibers or inorganic compounds, resin compositions improved in dispersibility of fillers can be obtained, whereby advantages given by using the fillers can be maintained and the resulting resin compositions are improved in mechanical strength.

(Vulcanizable rubber composition)

The rubber composition containing the unsaturated copolymer of ethylene according to the invention is a vulcanizable rubber composition. (The rubber composition of the invention is sometimes referred to as "vulcanizable rubber composition hereinafter.") This rubber composition can be used in the unvulcanized state, but if it is used as the vulcanized product, much more improved properties can be exhibited.

The vulcanizable rubber composition according to the invention can be vulcanized by heating it with a vulcanizing agent or irradiating it with electron rays without using a vulcanizing agent.

The vulcanizable rubber composition of the invention may appropriately contain other components according to the purpose in addition to the unsaturated copolymer of ethylene, and it is desired that the unsaturated copolymer of ethylene is contained in an amount of not less than 20% by weight, preferably not less than 25% by weight, based on the whole amount of the rubber composition. When the rubber composition contains the unsaturated copolymer of ethylene in the above range of amount, the composition exhibits favourable properties.

Examples of the other components which may be incorporated into the composition include various chemicals such as reinforcing agents, inorganic fillers, softening agents, antioxidants (stabilizers), processing aids, compounds which constitute a foaming system (e.g., foaming agent and foaming aid), plasticizers, colorants, blowing agents and other rubbers. The kinds and the amounts of the additives are properly determined depending on the purpose. Of the above additives, preferably used are reinforcing agent, inorganic filler, softening agent, etc. Details of these additives are described below.

Reinforcing agent and inorganic filler

Examples of the reinforcing agents include carbon blacks such as SRF, CPF, FEF, MAF, HAF, ISAF, SAF, FT and MT, surface treated materials obtained by surface treating of the above carbon blacks with silane coupling agents, silica, calcium carbonate, powdery talc and powdery silicic acid.

Examples of the inorganic fillers include precipitated calcium carbonate, ground limestone, talc and clay.

The rubber composition of the invention may contain the reinforcing agent and/or the inorganic filler in an amount of usually not more than 300 parts by weight, preferably 10 to 300 parts by weight, more preferably 10 to 200 parts by weight, based on 100 parts by weight of the unsaturated copolymer of ethylene.

From the rubber composition containing the reinforcing agent in the above-mentioned amount, a vulcanized rubber improved in mechanical properties such as tensile strength, tear strength and abrasion resistance can be obtained.

If the inorganic filler is added in the above-mentioned amount, the hardness can be improved without deteriorating other properties of the vulcanized rubber, and the cost can be lowered.

Softening agent

As the softening agents, those conventionally added to rubbers can be widely used, and examples thereof include:

petroleum type softening agents, such as process oil, lubricant, paraffin, liquid paraffin, petroleum asphalt and vaseline;

coal tar type softening agents, such as coal tar and coal tar pitch;

fatty oil type softening agents, such as castor oil, linseed oil, rapeseed oil and coconut oil;

waxes, such as tall oil, factice, beeswax, carnauba wax and lanolin;

fatty acids and fatty acid salts, such as ricinoleic acid, palmitic acid, barium stearate, calcium stearate and zinc laurate; and synthetic polymer materials, such as petroleum resin, atactic polypropylene and coumarone-indene resin.

Of these, preferred are petroleum type softening agents, and particularly preferred is process oil.

The softening agent may be contained in the rubber composition of the invention in an amount of usually not more than 200 parts by weight, preferably 10 to 200 parts by weight, more preferably 10 to 150 parts by weight, particularly preferably 10 to 100 parts by weight, based on 100 parts by weight of the unsaturated ethylene copolymer.

Antioxidant

The antioxidant is preferably contained in the rubber composition of the invention because the material life can be lengthened.

Examples of the antioxidants include:

aromatic secondary amine type stabilizers, such as phenylnaphthylamine, 4,4'-($\alpha,\alpha$-dimethylbenzyl) diphenylamine, and N,N'-di-2-naphthyl-p-phenylenediamine;

phenol type stabilizers, such as 2,6-di-t-butyl-4-methylphenol, and tetrakis-(methylene-3-(3',5'-di-t-butyl-4'-hydroxyphenyl)propionate)methane;

thioether type stabilizers, such as bis(2-methyl-4-(3-n-alkylthiopropionyloxy)-5-t-butylphenyl)sulfide;

benzimidazole type stabilizers, such as 2-mercaptobenzimidazole;

dithiocarbamate type stabilizers, such as nickel dibutyldithiocarbamate; and quinoline type stabilizers, such as a polymer from 2,2,4-trimethyl-1,2-dihydroquinoline. These stabilizers may be used in combination of two or more kinds.

The antioxidant may be used in an amount of not more than 5 parts by weight, preferably not more than 3 parts by weight, based on 100 parts by weight of the unsaturated copolymer of ethylene.

Processing aid

As the processing aids, those conventionally added to rubbers can be widely used. Examples thereof include various acids, such as ricinoleic acid, stearic acid, palmitic acid and lauric acid; salts of these higher fatty acids, such as barium stearate, zinc stearate and calcium stearate; and esters of the above acids.

The processing aid may be used in an amount of not more than 10 parts by weight, preferably not more than 5 parts by weight, based on 100 parts by weight of the unsaturated copolymer of ethylene.

Vulcanizing agent

When the rubber composition of the invention is vulcanized by heating, compounds which constitute a vulcanization system such as vulcanizing agent, vulcanization accelerator and vulcanization aid are generally added to the rubber composition.

Examples of the vulcanizing agents employable herein include sulfur, sulfur compounds and organic peroxides.

There is no specific limitation on the type of sulfur, and, for example, powdery sulfur, precipitated sulfur, colloidal sulfur, surface-treated sulfur and insoluble sulfur can be employed.

Examples of the sulfur compounds include sulfur chloride, sulfur dichloride, high-molecular weight polysulfide, morpholine disulfide, alkylphenol disulfide, tetramethylthiuram disulfide and selenium dimethyldithiocarbamate.

Examples of the organic peroxides include:

alkyl peroxides, such as dicumyl peroxide, di-t-butyl peroxide, di-t-butylperoxy-3,3,5-trimethylcyclohexane, t-butylcumyl peroxide, di-t-amyl peroxide, 2,5-dimethyl-2,5-di(t-butylperoxy)hexyne-3,2,5-dimethyl-2,5-di(benzoylperoxy)hexane, 2,5-dimethyl-2,5-di(t-butylperoxy)hexane, $\alpha,\alpha'$-bis(t-butylperoxy-m-isopropyl)benzene and t-butyl hydroperoxide;

peroxy esters such as t-butyl peroxyacetate, t-butyl peroxyisobutyrate, t-butyl peroxypivalate, t-butylperoxymaleic acid, t-butyl peroxyneodecanoate, t-butyl peroxybenzoate, and di-t-butyl peroxyphthalate; and ketone peroxides, such as dicyclohexanone peroxide.

These organic peroxides may be used in combination of two or more kinds.

Of these, preferred are organic peroxides having a temperature, at which the half-life period thereof is one minute, of 130° to 200° C., for example, dicumyl peroxide, di-t-butyl peroxide, di-t-butylperoxy-3,3,5-trimethylcyclohexane, t-butylcumyl peroxide, di-t-amyl peroxide and t-butyl hydroperoxide.

Of the above-mentioned various vulcanizing agents, sulfur or the sulfur compound, especially sulfur, is preferred in the invention, because particularly improved properties of the rubber composition can be exhibited.

When the vulcanizing agent is sulfur or the sulfur compound, it is used in an amount of 0.1 to 10 parts by weight, preferably 0.5 to 5 parts by weight, based on 100 parts by weight of the unsaturated ethylene copolymer.

When the vulcanizing agent is the organic peroxide, it is used in an amount of 0.0003 to 0.05 mol, preferably 0.001 to 0.03 mol, based on 100 g of the unsaturated ethylene copolymer.

Vulcanization accelerator

When sulfur or the sulfur compound is used as the vulcanizing agent, a vulcanization accelerator is preferably used in combination.

Examples of the vulcanization accelerators include:

sulfenamide compounds, such as N-cyclohexyl-2-benzothiazole sulfenamide (CBS), N-oxydiethylene-2-benzothiazole sulfenamide and N,N-diisopropyl-2-benzothiazole sulfenamide;

thiazole compounds, such as 2-mercaptobenzothiazole (MBT), 2-(2,4-dinitrophenyl)mercaptobenzothiazole, 2-(2,6-diethyl-4-morpholinothio)benzothiazole and dibenzothiazyl disulfide;

guanidine compounds, such as diphenylguanidine, triphenylguanidine, diorthonitrileguanidine, orthonitrile biguanide and diphenylguanidine phthaliate;

aldehyde amines or aldehyde-ammonia compounds, such as acetaldehyde-aniline reaction product, butylaldehyde-aniline condensate, hexamethylenetetramine and acetaldehyde ammonia;

imidazoline compounds, such as 2-mercaptoimidazoline;

thiourea compounds, such as thiocarbanilide, diethylthiourea, dubutylthiourea, trimethylthiourea and diorthotolylthiourea;

thiuram compounds, such as tetramethylthiuram monosulfide, tetramethylthiuram disulfide (TMTD), tetraethylthiuram disulfide, tetrabutylthiuram disulfide, pentamethylenethiuram tetrasulfide and dipentamethylenethiuram tetrasulfide (DPTT);

dithio acid salt compounds, such as zinc dimethyldithiocarbamate, zinc diethyldithiocarbamate, zinc di-n-butyldithiocarbamate, zinc ethylphenyldithiocabamate, zinc butylphenyldithiocarbamate, sodium dimethyldithiocarbamate, selenium dimethyldithiocarbamate and tellurium dimethyldithiocarbamate;

xanthate compounds, such as zinc dibutylxanthate; and zinc white.

The vulcanization accelerator is desirably used in an amount of 0.1 to 20 parts by weight, preferably 0.2 to 10 parts by weight, based on 100 parts by weight of the unsaturated ethylene copolymer.

Vulcanization aid

When the organic peroxide is used as the vulcanizing agent, a vulcanization aid is preferably used in an amount of 0.5 to 2 mol based on 1 mol of the organic peroxide, preferably almost in the equimolar amount.

Examples of the vulcanization aids include:

sulfur;

quinonedioxime compounds, such as p-quinonedioxime; and especially polyfunctional monomrs, such as:

(meth)acrylate compounds, such as trimethylolpropane triacrylate and polyethylene glycol dimethacrylate;

allyl compounds, such as diallyl phthalate and triallyl cyanurate;

maleimide compounds, such as m-phenylene bismaleimide; and divinylbenzene.

Foaming agent

When the rubber composition of the invention contains a compound which constitutes a foaming system, such as a foaming agent or a foaming aid, the composition can be subjected to foam molding.

As the foaming agents, those conventionally used in the foam molding of rubbers can be widely used. Particular examples thereof include inorganic foaming agents, such as sodium bicarbonate, sodium carbonate, ammonium bicarbonate, ammonium carbonate and ammonium nitrite; nitroso compounds, such as N,N'-dimethyl-N,N'-dinitrosoterephthalamide and N,N'-dinitrosopentamethylenetetramine; azo compounds, such as azodicarbonamide, azobisisobutyronitrile, azocyclohexylnitrile, azodiaminobenzene and barium azodicarboxylate; sulfonylhydrazide compounds, such as benzenesulfonylhydrazide, toluenesulfonylhydrazide, p,p'-oxybis(benzenesulfonylhydrazide) and diphenylsulfone-3, 3'-disulfonylhydrazide; azide compounds, such as calcium azide, 4,4-diphenyldisulfonylazide and p-toluenesulfonylazide.

Of these, preferred are nitroso compounds, azo compounds and azide compounds.

The foaming agent may be used in an amount of 0.5 to 30 parts by weight, preferably 1 to 20 parts by weight, based on 100 parts by weight of the unsaturated copolymer of ethylene. From the rubber composition containing the foaming agent in such amount, foamed products having an apparent specific gravity of 0.03 to 0.8 $g/cm^3$ can be produced.

In combination with the foaming agent, a foaming aid can be employed. When the foaming aid is used in combination, various effects such as lowering of decomposition temperature of the foaming agent, acceleration of decomposition thereof and uniformity of the resulting foam can be exerted. Examples of the foaming agents include organic acids, such as salicylic acid, phthalic acid, stearic acid and oxalic acid, urea and its derivative.

The foaming aid may be used in an amount of 0.01 to 10 parts by weight, preferably 0.1 to 5 parts by weight, based on 100 parts by weight of the unsaturated copolymer of ethylene.

Other rubber

The rubber composition of the invention may contain other known rubbers as long as the objects of the invention are not marred.

Examples of such rubbers include natural rubbers (NR); isoprene type rubbers, such as isoprene rubber (IR); and conjugated diene type rubbers, such as butadiene rubber (BR), styrene-butadiene rubber (SBR), acrylonitrile-butadiene rubber (NBR) and chloroprene rubber (CR).

Also employable are conventionally known ethylene-α-olefin copolymer rubbers, for example, ethylene-propylene random copolymer (EPR) and ethylene-α-olefin-polyene terpolymer other than the unsaturated copolymer of ethylene, such as EPDM.

The vulcanizable rubber composition of the invention can be prepared from the unsaturated copolymer of ethylene and the above-mentioned other components by conventional processes for preparing rubber blends. For example, the unsaturated copolymer of ethylene and other components are kneaded at 80° to 170° C. for 3 to 10 minutes using an internal mixer such as Banbury mixer, kneader and intermixer, then the vulcanizing agent and the vulcanization accelerator or the vulcanization aid are added if necessary, and the resulting mixture is kneaded at a roll temperature of 40° to 80° C. for 5 to 30 minutes using a roll (e.g., an open roll) or a kneader, followed by delivering. Thus, a rubber composition (rubber blend) in the form of usually ribbon or sheet can be obtained. If the temperature for kneading by the use of the internal mixer is low, the vulcanizing agent, the vulcanization accelerator and the foaming agent may be simultaneously kneaded.

(Vulcanized rubber)

A vulcanizate (vulcanized rubber) of the rubber composition of the invention can be obtained by generally preforming the unvulcanized rubber composition into a desired shape using various means such as an extrusion molding machine, a calender roll, a press, an injection molding machine and a transfer molding machine, and simultaneously or thereafter heating the preform in a vulcanizing bath or irradiating it with electron rays so as to vulcanize it.

When the rubber composition is vulcanized by heating, the rubber composition is preferably heated at a temperature of 150° to 270° C. for 1 to 30 minutes using a heating bath of hot air, glass bead fluidized bed, UHF (ultrahigh frequency electromagnetic wave), steam or LCM (molten salt bath).

When the rubber composition is vulcanized by irradiation with electron rays without using a vulcanizing agent, the preformed rubber composition is irradiated with electron rays having energy of 0.1 to 10 MeV, preferably 0.3 to 2 MeV at an absorbed dose of 0.5 to 35 Mrad, preferably 0.5 to 10 Mrad.

In the preforming and vulcanization, a mold may be used or may not be used. If a mold is not used, preforming and vulcanization of the rubber composition are generally carried out continuously.

The rubber composition thus preformed and vulcanized (vulcanized rubber) can be used for automotive industrial parts such as weatherstrip, door glass run channel, window frame, radiator hose, brake parts and wiper blade; industrial rubber parts such as rubber roll, belt, packing and hose; electrical insulating materials such as anode cap and grommet; civil engineering and building materials such as building gasket and civil engineering sheet; and rubberized fabrics.

The vulcanized foamed product obtained by foaming the rubber blend containing the foaming agent under heating can be used for heat insulating materials, cushioning materials, sealing materials, etc.

Next, a process for preparing the aforesaid branched chain polyene (Ib) (branched chain triene or tetraene (Ib)) is described in detail.

Process for preparing branched chain polyene (Ib)

Among the polyenes represented by the formula (H-1) for use in the invention, the branched chain triene or tetraene in which p=1 and q=0 can be synthesized by allowing ethylene to react with a conjugated diene compound (H-1a) represented by the following formula (H-1a).

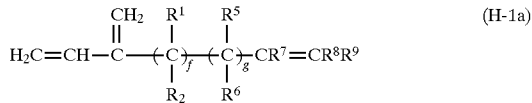

wherein f, g and $R^1$ to $R^9$ are the same as those in the formula (H-1).

A straight chain polyene compound represented by the following formula (H-1b), which is sometimes produced as a subproduct in the reaction of ethylene with the conjugated diene compound represented by the formula (H-1a), can be separated and removed usually by distillation. However, a mixture of the polyene (H-1) and the subproduct (H-1b) can be also used in polymerization without separation of (H-1b).

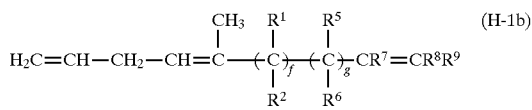

wherein f, g and $R^1$ to $R^9$ are the same as those in the formula (H-1a).

Furthermore, the branched chain polyene (Ib) used in the invention can be prepared by, for example, allowing a compound which has conjugated diene and is represented by the following formula (I-a) (hereinafter sometimes referred to as "conjugated diene compound (I-a)") to react with ethylene.

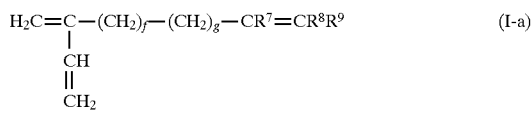

wherein f is an integer of 0 to 5, g is an integer of 1 to 6, $R^7$ is an alkyl group of 1 to 5 carbon atoms, and $R^8$ and $R^9$ are each independently hydrogen or an alkyl group of 1 to 5 carbon atoms.

Examples of the alkyl groups of 1 to 5 carbon atoms include the same groups as described in the aforesaid formula (Ib), such as methyl.

The conjugated diene compounds represented by the formula (I-a) are, for example, the following compounds (1) to (24):

(1) 3-methylene-1,5-heptadiene,
(2) 6-methyl-3-methylene-1,5-heptadiene,
(3) 6-methyl-3-methylene-1,5-octadiene,
(4) 6-ethyl-3-methylene-1,5-octadiene,
(5) 5,6-dimethyl-3-methylene-1,5-heptadiene,
(6) 5,6-dimethyl-3-methylene-1,5-octadiene,
(7) 3-methylene-1,5-nonadiene,
(8) 6-methyl-3-methylene-1,5-nonadiene,
(9) 6-methyl-5-propyl-3-methylene-1,5-heptadiene,
(10) 3-methylene-1,6-octadiene,
(11) 7-methyl-3-methylene-1,6-octadiene,
(12) 3-methylene-1,6-decadiene,
(13) 7-methyl-3-methylene-1,6-decadiene,
(14) 6,7-dimethyl-3-methylene-1,6-octadiene,
(15) 6,7-dimethyl-3-methylene-1,6-nonadiene,
(16) 6,7-dimethyl-3-methylene-1,6-decadiene,
(17) 7-methyl-6-ethyl-3-methylene-1,6-decadiene,
(18) 6,7-diethyl-3-methylene-1,6-nonadiene,

(19) 8-methyl-3-methylene-1,7-nonadiene,
(20) 7,8-dimethyl-3-methylene-1,7-nonadiene,
(21) 9-methyl-3-methylene-1,8-decadiene,
(22) 8,9-dimethyl-3-methylene-1,8-decadiene,
(23) 10-methyl-3-methylene-1,9-undecadiene, and
(24) 9,10-dimethyl-3-methylene-1,9-undecadiene.

Through the above reaction, the branched chain polyene (Ib) is obtained generally as a mixture of a trans form and a cis form. The trans form and the cis form can be separated from each other by distillation depending on the structure of the branched chain polyene (Ib), but a mixture of both isomers can be used in polymerization without separation. In certain cases, only one geometrical isomer can be obtained.

In the above reaction, a straight chain polyene compound represented by the following formula (I-b) is sometimes produced as a subproduct together with the branched chain polyene.

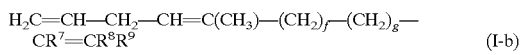

(I-b)

wherein f, g, $R^7$, $R^8$ and $R^9$ are the same as those in the formula (I-a).

This subproduct can be separated usually by distillation, but the mixture containing the subproduct can be used in polymerization without separation.

Though the conditions for the reaction of the conjugated diene compound (I-a) with ethylene vary according to the type of the compound (I-a) having conjugated diene, in general, the reaction is carried out at a temperature of usually 50° to 200° C., preferably 70° to 150° C., an ethylene pressure of 0.5 to 100 kg/cm², preferably 1 to 100 kg/cm², more preferably 5 to 70 kg/cm², for a reaction time of 0.5 to 30 hours. Ethylene may be fed to the reactor continuously or intermittently.

This reaction may be carried out in an atmosphere of inert gas such as nitrogen or argon. The reaction may be conducted without using any solvent, or may be conducted in the presence of an inert hydrocarbon solvent such as hexane, heptane, octane, nonane, decane, undecane, dodecane, tridecane, toluene or xylene.

This reaction is carried out generally in the presence of a catalyst. Especially when the reaction is carried out in the presence of a catalyst comprising a transition metal compound and an organoaluminum compound, the branched chain polyene (Ib) can be efficiently obtained.

Examples of such transition metal compounds include chlorides, bromides, acetylacetonato salts, 1,1,1,5,5,5-hexafluoroacetylacetonato salts and dipivaloylmethane salts of a transition metal selected from Group VIII of the periodic table such as iron, ruthenium, cobalt, rhodium, iridium, nickel and palladium. Of these, preferred are compounds (chlorides) of cobalt, iron, nickel, rhodium and palladium; particular preferred are compounds (chlorides) of cobalt; and most preferred is cobalt chloride.

The transition metal compound (e.g., transition metal chloride) can be used, as it is, in the reaction for preparing the catalyst. In the preparation of the catalyst, however, the transition metal compound is preferably used in the form of a transition metal complex in which an organic ligand is coordinated to the transition metal compound. That is, it is preferred that an organic compound (coordination compound) which is able to become a ligand of the transition metal is allowed to exist in the reaction system together with the transition metal compound, or a transition metal complex is preliminarily formed from the transition metal compound, followed by using it in the reaction for preparing a catalyst.

Examples of the coordination compounds include bis (diphenylphosphino)methane, 1,2-bis(diphenylphosphino) ethane, 1,3-bis(diphenylphosphino)propane, 1,4-bis (diphenylphosphino)butane, triethylphosphine, tributylphosphine, triphenylphosphine, cyclooctadiene and cyclooctatetraene.

Preferably used as the complex in which the organic ligand is coordinated to the transition metal compound are (1,2-bis(diphenylphosphino)ethane)cobalt(II) chloride, (1,2-bis(diphenylphosphino)ethane)nickel(II) chloride and bis (triphenylphosphine)nickel(II) chloride.

As the organoaluminum compound, the aforesaid ones can be used, and preferably used is triethylaluminum. The organoaluminum compound may be used as it is, or may be used in the form of a toluene solution or a hexane solution.

In the reaction of the compound (I-a) having conjugated diene with ethylene, the transition metal compound is used in an amount of preferably 0.001 to 10% by mol, more preferably 0.01 to 1% by mol, based on the amount of the compound (I-a) having a conjugated diene. The coordination compound is used in an amount of preferably 0 to 20 mol times, more preferably 0.1 to 5 times, as much as the amount of the transition metal compound.

The organoaluminum compound is used in an amount of preferably 1 to 200 mol times, particularly preferably 3 to 100 mol times, as much as the amount of the transition metal compound.

In the reaction system containing the compound (I-a) having conjugated diene and ethylene, the transition metal compound (or the transition metal complex) may be allowed to react with the organoaluminum compound in situ to prepare a catalyst, but it is preferred to use, as a catalyst, a reaction product which is preliminarily obtained by contacting the transition metal compound (or the transition metal complex) with the organoaluminum compound.

In more detail, the catalyst can be prepared by, for example, mixing the transition metal compound with the coordination compound in a solvent similar to the above-mentioned reaction solvent, e.g., decane, in an inert atmosphere, and then adding the organoaluminum compound, followed by stirring at room temperature.

For preparing the branched chain tetraene (Ib') (branched chain polyene (Ib')) used in the invention, in which there are four carbon-carbon double bonds in the formula (H-1) (in other words $R^9$ is —$(CH_2)n$—$CR^{10}$=$R^{11}R^{12}$ in the formula (H-1)), a conjugated diene compound represented by, for example, the following formula (I-aa) is used in place of the conjugated diene compound represented by the formula (I-a) in the above-mentioned reaction of ethylene with the conjugated diene compound represented by the formula (I-a).

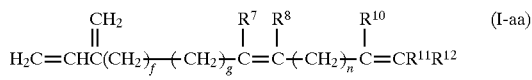

(I-aa)

wherein f is an integer of 0 to 5; g is an integer of 1 to 6, preferably an integer of 1 to 3; n is an integer of 1 to 5; $R^7$ to $R^{11}$ are each independently hydrogen or an alkyl group of 1 to 5 carbon atoms, preferably 1 to 3 carbon atoms; and $R^{12}$ is an alkyl group of 1 to 5 carbon atoms.

In this reaction, ethylene is desirably fed to the reactor under a pressure of usually 0.5 to 100 kg/cm², preferably 1 to 50 kg/cm². Other reaction conditions are the same as those in the reaction of ethylene with the conjugated diene compound represented by the formula (I-a).

In the reaction of ethylene with the conjugated diene compound (I-aa), a straight chain polyene compound represented by the following formula (I-bb) is sometimes produced as a subproduct together with the branched chain polyene (Ib'), and this subproduct can be separated and removed in the same manner as described above. However, the mixture obtained can be used in polymerization without separation of the subproduct.

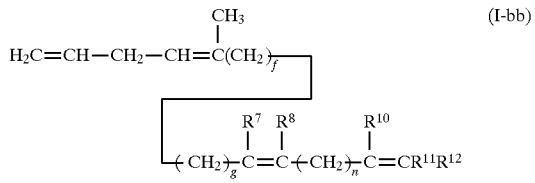

(I-bb)

wherein f, g, n and $R^7$ to $R^{12}$ are the same as those in the formula (I-aa).

EFFECT OF THE INVENTION

According to the present invention, an unsaturated copolymer of ethylene which is excellent in weathering resistance, heat resistance and ozone resistance and has a high vulcanizing rate can be obtained.

EXAMPLE

The present invention will be further described with reference to the following examples, but it should be construed that the invention is in no way limited to those examples.

Reference Example 1
(Synthesis of 6,10-dimethyl-1,5,9-undecatriene (DMUT)) (p=0, q=1, f=1, g=2, total number of hydrogen atoms directly bonded to the carbon atoms adjacent to all the carbon-to-carbon double bonds: 17)

(DMUT)

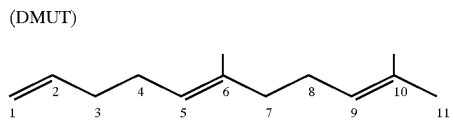

To a 1-liter three-necked flask equipped with a stirrer, a Dimroth condenser, a dropping funnel and a thermometer were introduced 25.5 g (1.05 g.atom) of flaky metallic magnesium, 200 ml of anhydrous diethyl ether and 200 mg of 1,2-dibromoethane with stirring in a nitrogen atmosphere, and thereto was dropwise added a small amount of a solution of allyl bromide (127 g, 1.05 mol) in anhydrous diethyl ether (200 ml).

After the exothermic reaction of the content in the flask was initiated and allylmagnesium bromide (Grignard reagent) began to be produced, to the flask was added 400 ml of anhydrous diethyl ether, and was further dropwise added the rest of the anhydrous diethyl ether solution of allyl bromide under cooling in an ice bath over a period of 5 hours (flask internal temperature: not higher than 5° C.). After the dropwise addition of the anhydrous diethyl ether solution of allyl bromide was completed, the mixture was stirred for 0.5 hour to obtain an allylmagnesium bromide solution.

The insoluble portion remaining in the allylmagnesium bromide solution was removed by decantation, and the solution was transferred into a 2-liter three-necked flask in a nitrogen atmosphere.

While the three-necked flask containing the allylmagnesium bromide solution was cooled in an ice bath, to the flask was dropwise added a solution of geranyl bromide (150 g, 0.69 mol) in anhydrous diethyl ether (200 ml) over a period of 2 hours with keeping the flask internal temperature at not higher than 5° C.

After the dropwise addition of the anhydrous diethyl ether solution of geranyl bromide was completed, the mixture was further stirred at room temperature for 8 hours.

With cooling the reaction mixture in an ice bath, to the mixture was dropwise added slowly a saturated ammonium chloride aqueous solution and were further added diethyl ether and water to separate the mixture into an organic phase and an aqueous phase.

The organic phase was washed with a saturated sodium hydrogencarbonate solution and a saturated saline solution and then dried over anhydrous magnesium sulfate.

The solvent was evaporated from the dried product and the residue was subjected to vacuum distillation. Thus, 104 g of the aimed product (6,10-dimethyl-1,5,9-undecatriene (DMUT)) was obtained (yield: 85%, based on geranyl bromide).

The state and the properties of the 6,10-dimethyl-1,5,9-undecatriene (DMUT) are described below.

State: colorless, oily; Boiling point: 58°–60° C./2 mmHg; MS spectrum: 178 ($M^+$: molecule ion peak); $^1$H-NMR spectrum ($CDCl_3$ solution):; δ1.64 (6H, singlet); 1.70 (3H, singlet); 2.1 (8H, multiplet); 5.0 (4H, multiplet); 5.8 (1H, multiplet); IR spectrum (neat, $cm^{-1}$) 3075, 2970, 2920, 2850, 1640, 1440, 1380, 1105, 995, 905

Reference Example 2
(Synthesis of 5,9-dimethyl-1,4,8-decatriene (DMDT)) (p=0, q=1, f=0, g=2, total number of hydrogen atoms directly bonded to the carbon atoms adjacent to all the carbon-to-carbon double bonds: 15)

(DMDT)

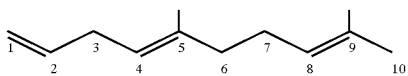

To a 1-liter three-necked flask equipped with a stirrer, a Dimroth condenser, a dropping funnel and a thermometer was introduced 500 ml (0.435 mol) of an anhydrous tetrahydrofuran solution of vinylmagnesium bromide (0.87 mol/liter) in a nitrogen atmosphere, and the content in the flask was cooled in an ice bath.

Then, with stirring the content in the flask, 100 ml of an anhydrous tetrahydrofuran solution of geranyl bromide (75 g, 0.346 mol) was dropwise added to the flask over a period of 30 minutes, and the mixture was stirred for 8 hours.

While the reaction mixture was cooled in an ice bath, to the flask was dropwise added slowly a saturated ammonium chloride aqueous solution and were further added diethyl ether and water to separate the mixture into an organic phase and an aqueous phase.

The organic phase was washed with a saturated sodium hydrogencarbonate solution and a saturated saline solution and then dried over anhydrous magnesium sulfate.

The solvent was evaporated from the dried product and the residue was subjected to vacuum distillation. Thus, 21.9 g of the aimed product (5,9-dimethyl-1,4,8-decatriene (DMDT)) was obtained (yield: 39%, based on geranyl bromide).

The state and the properties of the 5,9-dimethyl-1,4,8-decatriene (DMDT) are described below.

State: colorless, oily; Boiling point: 56°–58° C./2 mmHg MS spectrum: 164 (M+); $^1$H-NMR spectrum ($CDCl_3$ solution):; δ1.64 (6H, singlet); 1.70 (3H, singlet); 2.04 (4H, singlet); 2.76 (2H, multiplet); 5.0 (4H, multiplet); 5.8 (1H, multiplet); IR spectrum (neat):; 3075, 2970, 2920, 2850, 1640, 1440, 1380, 1105, 995, 905

Example 1

In a 2-liter polymerizer equipped with a stirring blade, terpolymerization reaction of ethylene, propylene and the 6,10-dimethyl-1,5,9-undecatriene (DMUT) synthesized in Reference Example 1 was continuously carried out.

The terpolymerization reaction was conducted in a manner described below.

To the polymerizer were continuously fed, from the top thereof, a toluene solution of DMUT at a feed rate of 0.5 l/hr so that the concentration in the polymerizer became 80 mmol/l, a toluene solution of bis(1,3-dimethylcyclopentadienyl)zirconium dichloride as a catalyst at a feed rate of 0.5 l/hr so that the zirconium concentration in the polymerizer became 0.02 mmol/l, a toluene solution of methylaluminoxane (—Al(Me)—O—) as a cocatalyst at a feed rate of 0.5 l/hr so that the aluminum concentration in the polymerizer became 10.0 mmol/l, and toluene at a feed rate of 0.5 l/hr.

On the other hand, the polymer solution was continuously drawn out from the top of the polymerizer so that the polymer solution in the polymerizer was kept constant in an amount of 1 liter and the average residence time became 30 minutes.

Further, to the polymerization system were fed ethylene at a feed rate of 100 l/hr and propylene at a feed rate of 140 l/hr using bubble tube. The copolymerization reaction was carried out at 20° C. by circulating a cooling medium through a jacket provided outside the polymerizer.

Through the copolymerization reaction under the above conditions, a polymer solution containing an ethylene-propylene-DMUT copolymer was obtained.

The polymer solution was deashed using hydrochloric acid and then introduced into a large amount of methanol to precipitate the polymer (ethylene-propylene-DMUT copolymer), followed by vacuum drying at 100° C. for 24 hours.

Thus, an ethylene-propylene-DMUT copolymer was obtained in an amount of 123 g per hour (polymer concentration: 61.5 g/liter).

In the ethylene-propylene-DMUT copolymer, the ethylene units were contained in amounts of 71.3% by mol, the propylene units were contained in amounts of 27.6% by mol, the DMUT units were contained in amounts of 1.1% by mol, and the molar ratio of the ethylene units to the propylene units was 72/28 (ethylene units/propylene units). The intrinsic viscosity ($\eta$) (measured in Decalin at 135° C., the same shall apply hereinafter) of this ethylene-propylene-DMUT copolymer was 1.5 dl/g.

Then, a composition containing 100 parts by weight of the ethylene-propylene-DMUT copolymer obtained above, 5 parts by weight of zinc white No. 1, 1 part by weight of stearic acid, 80 parts by weight of N330 (trade name: Seast 3, available from Tokai Carbon K.K.), 50 parts by weight of oil (trade name: Sunthene 4240, available from Sun Oil K.K.), 1.0 part by weight of a vulcanization accelerator A (trade name: Nocceler TT, available from Ouchi Shinko Kagaku K.K.), 0.5 part by weight of a vulcanization accelerator B (trade name: Nocceler M, available from Ouchi Shinko Kagaku K.K.) and 1.5 parts by weight of sulfur as shown in Table 1 was kneaded by means of a 6-inch open roll, to obtain an unvulcanized rubber blend.

The vulcanizing rate of the rubber blend was evaluated. As a result, T90 was 4.7 minutes.

The result is set forth in Table 2.

The evaluation of the vulcanizing rate was carried out in the following manner. As a measuring device, JSR curelastometer 3 type (produced by Japan Synthetic Rubber Co., Ltd.) was used. A difference between the minimum value ML and the maximum value MH of the torque obtained from the vulcanization curve was taken as ME (MH−ML=ME), and the vulcanizing rate was evaluated based on the period of time required for attaining 90% ME, i.e., T90 (minute).

Further, the unvulcanized rubber blend having a composition shown in Table 1 was press molded under the conditions of a temperature of 160° C. and a molding time of T90 (minute)+5 minutes. T90 (minute) of the unvulcanized rubber blend, and modulus at 100%, 200% and 300% (M100, M200 and M300), tensile strength ($T_B$), elongation ($E_B$) and hardness ($H_S$) of the resulting vulcanized rubber were measured. These properties were measured in accordance with JIS K 6301.

The results are set forth in Table 2.

TABLE 1

| Composition of unvulcanized rubber blend | part(s) by weight |
|---|---|
| Ethylene-propylene-DMUT copolymer | 100 |
| Zinc white No. 1 | 5 |
| Stearic acid | 1 |
| N330 (Seast 3, from Tokai Carbon K.K.) | 80 |
| Oil (Sunthene 4240, from Sun Oil K.K.) | 50 |
| Vulcanization accelerator A (Nocceler TT, from Ouchi Shinko Kagaku K.K.) | 1.0 |
| Vulcanization accelerator B (Nocceler M, from Ouchi Shinko Kagaku K.K.) | 0.5 |
| Sulfur | 1.5 |

Example 2

An ethylene-propylene-DMDT copolymer was obtained in an amount of 110 g per hour (polymer concentration: 55.0 g/liter) in the same manner as described in Example 1 except that the DMDT synthesized in Reference Example 2 was used in place of the DMUT.

In the ethylene-propylene-DMDT copolymer, the ethylene units were contained in amounts of 69.0% by mol, the propylene units were contained in amounts of 28.5% by mol, the DMDT units were contained in amounts of 2.5% by mol, and the molar ratio of the ethylene units to the propylene units was 71/29 (ethylene units/propylene units). The intrinsic viscosity ($\eta$) of this ethylene-propylene-DMDT copolymer was 1.42 dl/g.

Then, an unvulcanized rubber blend was obtained in the same manner as described in Example 1 except that the ethylene-propylene-DMDT copolymer obtained above was used in place of the ethylene-propylene-DMUT copolymer of Example 1.

The vulcanizing rate of the rubber blend was evaluated. As a result, T90 was 5.2 minutes.

Further, the unvulcanized rubber blend obtained in the same composition of Table 1 except that the ethylene-propylene-DMUT copolymer of Example 1 was replaced with the ethylene-propylene-DMDT copolymer obtained above was press molded under the conditions of a temperature of 160° C. and a molding time of T90 (minute)+5 minutes. T90 (minute) of the unvulcanized rubber blend, and modulus at 100%, 200% and 300% (M100, M200 and M300), tensile strength ($T_B$), elongation ($E_B$) and hardness ($H_S$) of the resulting vulcanized rubber were measured.

The results are set forth in Table 2.

Comparative Example 1
(5-ethylidene-2-norbornene (ENB))
(total number of hydrogen atoms directly bonded to the carbon atoms adjacent to all the carbon-to-carbon double bonds: 7)

In a 2-liter polymerizer equipped with a stirring blade, copolymerization reaction of ethylene, propylene and 5-ethylidene-2-norbornene (ENB) was continuously carried out.

This copolymerization reaction was conducted in a manner described below.

To the polymerizer were continuously fed, from the top thereof, a hexane solution of ENB (7.1 g/l) at a feed rate of 0.5 l/hr, a hexane solution of $VO(OC_2H_5)Cl_2$ (0.8 mmol/l) as a catalyst at a feed rate of 0.5 l/hr, a hexane solution of ethylaluminum sesquichloride $(Al(C_2H_5)_{1.5}Cl_{1.5})$ (8.0 mmol/l) as a cocatalyst at a feed rate of 0.5 l/hr, and hexane at a feed rate of 0.5 l/hr.

On the other hand, the polymer solution was continuously drawn out from the top of the polymerizer so that the polymer solution in the polymerizer was kept constant in an amount of 1 liter. Further, to the polymerization system were fed ethylene at a feed rate of 120 l/hr, propylene at a feed rate of 180 l/hr and hydrogen at a feed rate of 5 l/hr using bubble tube. The copolymerization reaction was carried out at 30° C. by circulating a cooling medium through a jacket provided outside the polymerizer.

Through the copolymerization reaction under the above conditions, a polymer solution containing an ethylene-propylene-ENB copolymer was obtained.

The polymer solution was deashed using hydrochloric acid and then introduced into a large amount of methanol to precipitate the polymer (ethylene-propylene-ENB copolymer), followed by vacuum drying at 100° C. for 24 hours.

Thus, an ethylene-propylene-ENB copolymer was obtained in an amount of 64.8 g per hour.

In the ethylene-propylene-ENB copolymer, the ethylene units were contained in amounts of 66.8% by mol, the propylene units were contained in amounts of 31.4% by mol, the ENB units were contained in amounts of 1.8% by mol, and the molar ratio of the ethylene units to the propylene units was 68/32 (ethylene units/propylene units). The intrinsic viscosity ($\eta$) of this ethylene-propylene-ENB copolymer was 2.2 dl/g.

Using the ethylene-propylene-ENB copolymer, the vulcanizing rate was evaluated in the same manner as described in Example 1. As a result, T90 was 11.2 minutes.

The result is set forth in Table 2.

Example 3

In a 2-liter polymerizer equipped with a stirring blade and a gas-blowing tube, terpolymerization reaction of ethylene, propylene and the DMUT obtained in Reference Example 1 was carried out.

The terpolymerization reaction was conducted in a manner described below.

In a stream of nitrogen, to the polymerizer were introduced 800 ml of dehydrated and dried toluene and DMUT so that the DMUT concentration in the system became 120 mmol/l. The temperature of the solution in the polymerizer was kept at 20° C., and to the polymerizer were continuously fed ethylene at a feed rate of 100 l/hr and propylene at a feed rate of 140 l/hr.

To the polymerizer were further introduced 11.1 ml of a toluene solution of methylaluminoxane (0.72 mmol/ml in terms of aluminum atom) and 3.2 ml of a toluene solution of bis(1,3-dimethylcyclopentadienyl)zirconium dichloride (0.005 mmol/ml) to initiate the polymerization.

After the polymerization was conducted at 20° C. for 80 minutes, a small amount of isobutyl alcohol was added to the polymerizer so as to terminate the polymerization. The polymer solution obtained was washed (deashed) with hydrochloric acid and then introduced into a large amount of methanol to precipitate an ethylene-propylene-DMUT copolymer.

Then, the ethylene-propylene-DMUT copolymer thus precipitated was recovered and dried under reduced pressure at 100° C. for 24 hours.

Thus, 64.6 g of an ethylene-propylene-DMUT copolymer was obtained.

In the ethylene-propylene-DMUT copolymer, the ethylene units were contained in amounts of 68.5% by mol, the propylene units were contained in amounts of 28.3% by mol, the DMUT units were contained in amounts of 3.2% by mol, and the molar ratio of the ethylene units to the propylene units was 71/29 (ethylene units/propylene units). The intrinsic viscosity ($\eta$) of this ethylene-propylene-DMUT copolymer was 1.35 dl/g.

Then, an unvulcanized rubber blend was obtained in the same manner as described in Example 1 except that the ethylene-propylene-DMUT copolymer obtained above was used in place of the ethylene-propylene-DMUT copolymer of Example 1.

The vulcanizing rate of the rubber blend was evaluated in the same manner as described in Example 1. As a result, T90 was 4.1 minutes.

Further, the unvulcanized rubber blend obtained in the same composition of Table 1 except that the ethylene-propylene-DMUT copolymer of Example 1 was replaced with the ethylene-propylene-DMUT copolymer obtained above was press molded under the conditions of a temperature of 160° C. and a molding time of T90 (minute)+5 minutes. T90 (minute) of the unvulcanized rubber blend, and modulus at 100%, 200% and 300% (M100, M200 and M300), tensile strength ($T_B$), elongation ($E_B$) and hardness ($H_S$) of the resulting vulcanized rubber were measured.

The results are set forth in Table 2.

TABLE 2

| Example No. | Ex. 1 | Ex. 2 | Ex. 3 | Comp. Ex. 1 |
|---|---|---|---|---|
| Vulcanization properties | | | | — |
| | | | | — |
| M100 (kgf/cm$^2$) | 25 | 27 | 30 | — |
| M200 (kgf/cm$^2$) | 59 | 66 | 70 | — |
| M300 (kgf/cm$^2$) | 79 | 87 | 93 | — |
| $T_B$ (kgf/cm$^2$) | 145 | 141 | 135 | — |
| $E_B$ (kgf/cm$^2$) | 520 | 440 | 400 | — |
| $H_S$ (JIS A) | 65 | 66 | 67 | — |
| Vulcanizing rate | | | | |
| T90 (minutes) | 4.7 | 5.2 | 4.1 | 11.2 |

Reference Example 3
(Preparation of catalyst)

In an argon atmosphere, to a 50-ml flask equipped with a stirrer were introduced 43 mg (0.33 mmol) of anhydrous cobalt(II) chloride, 263 mg (0.66 mmol) of 1,2-bis(diphenylphosphino)ethane and 23 ml of anhydrous decane, and they were stirred at 25° C. for 2 hours. Then, 17 ml of a triethylaluminum/toluene solution (triethylaluminum: 17 mmol, concentration: 1 mol/liter) was added at 25° C., and the mixture was stirred for 2 hours to obtain a catalyst.

(Synthesis of 4-ethylidene-8-methyl-1,7-nonadiene (EMN)) (p=1, q=0, f=1, g=1, total number of hydrogen atoms directly bonded to the carbon atoms adjacent to all the carbon-to-carbon double bonds: 15)

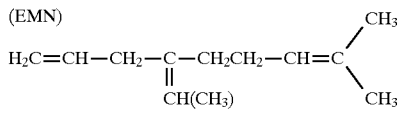

(EMN)

To a 300-ml stainless steel (SUS316) autoclave were introduced 100 g (734 mmol) of 7-methyl-3-methylene-1,6-octadiene (β-myrcene) and the whole amount of the catalyst prepared above in an argon atmosphere, and the autoclave was sealed. Then, the autoclave was connected with an ethylene bomb, through which ethylene was introduced, so as to pressurize the autoclave up to 35 kg/cm². Thereafter, the autoclave was heated to 95° C., and ethylene was intermittently replenished five times to perform the reaction for 15 hours in total.

After the reaction was completed, the autoclave was cooled and released. The reaction mixture obtained was poured into 100 ml of water to separate the mixture into an organic phase and an aqueous phase. From the organic phase, a low-boiling substance portion was removed by means of an evaporator, followed by vacuum precision distillation of 20 plates.

Thus, 83 g of the aimed product (EMN) was obtained (yield: 69%). Further, 16 g of 5,9-dimethyl-1,4,8-decatriene was produced as a subproduct (yield: 13%).

The results of analysis of the 4-ethylidene-8-methyl-1,7-nonadiene (EMN) are described below.

Boiling point: 103°–105° C./30 mmHg;
GC-MS (gas chromatography-mass spectrometric analysis): M/z 164 (m⁺: molecule ion peak), 149, 123, 95, 69, 41, 27; Infrared absorption spectrum (neat, cm⁻¹); Absorption peak: 3080, 2975, 2925, 2850, 1670, 1640, 1440, 1380, 1235, 1110, 995, 910, 830; $^1$H-NMR spectrum (solvent: CDCl₃)

The absorption peaks are set forth in Table 3.

TABLE 3

| ppm (δ) | (Number of protons, Peak) |
|---|---|
| 1.59 | (3H, doublet, J = 7 Hz) |
| 1.60 | (3H, singlet) |
| 1.68 | (3H, singlet) |
| 2.00 | (2H, multiplet) |
| 2.06 | (2H, multiplet) |
| 2.80 | (2H, doublet, J = 7 Hz) |
| 4.9–5.2 | (3H, multiplet) |
| 5.30 | (1H, quartet, J = 7 Hz) |
| 5.75 | (1H, multiplet) |

Example 4

In a 2-liter polymerizer equipped with a stirring blade, terpolymerization reaction of ethylene, propylene and the mixture containing principally 4-ethylidene-8-methyl-1,7-nonadiene (EMN) synthesized in Reference Example 3 (hereinafter referred to as EMN) was continuously carried out.

The terpolymerization reaction was conducted in a manner described below.

To the polymerizer were continuously fed, from the top thereof, a toluene solution of EMN at a feed rate of 0.2 l/hr so that the concentration in the polymerizer became 180 mmol/l, a toluene solution of bis(1,3-dimethylcyclopentadienyl)zirconium dichloride as a catalyst at a feed rate of 0.1 l/hr so that the zirconium concentration in the polymerizer became 0.02 mmol/l, a toluene solution of methylaluminoxane (—Al(Me)—O—) as a cocatalyst at a feed rate of 0.2 l/hr so that the aluminum concentration in the polymerizer became 10.0 mmol/l, and toluene at a feed rate of 0.5 l/hr.

On the other hand, the polymer solution was continuously drawn out from the top of the polymerizer so that the polymer solution in the polymerizer was kept constant in an amount of 1 liter and the average residence time became 60 minutes.

Further, to the polymerization system were fed ethylene at a feed rate of 100 l/hr and propylene at a feed rate of 140 l/hr using bubble tube. The copolymerization reaction was carried out at 20° C. by circulating a cooling medium through a jacket provided outside the polymerizer.

Through the copolymerization reaction under the above conditions, a polymer solution containing an ethylene-propylene-EMN copolymer was obtained.

The polymer solution was deashed using hydrochloric acid and then introduced into a large amount of methanol to precipitate the polymer (ethylene-propylene-EMN copolymer), followed by vacuum drying at 100° C. for 24 hours.

Thus, an ethylene-propylene-EMN copolymer was obtained in an amount of 32 g per hour.

In the ethylene-propylene-EMN copolymer, the ethylene units were contained in amounts of 72.9% by mol, the propylene units were contained in amounts of 26.2% by mol, the EMN units were contained in amounts of 0.9% by mol, and the molar ratio of the ethylene units to the propylene nits was 74/26 (ethylene units/propylene units). The intrinsic viscosity (η) of this ethylene-propylene-EMN copolymer was 1.7 dl/g.

Then, a composition containing 100 parts by weight of the ethylene-propylene-EMN copolymer obtained in Example 4, 5 parts by weight of zinc white No. 1, 1 part by weight of stearic acid, 80 parts by weight of N330 (trade name: Seast 3, available from Tokai Carbon K.K.), 50 parts by weight of oil (trade name: Sunthene 4240, available from Sun Oil K.K.), 1.0 part by weight of a vulcanization accelerator A (trade name: Nocceler TT, available from Ouchi Shinko Kagaku K.K.), 0.5 part by weight of a vulcanization accelerator B (trade name: Nocceler M, available from Ouchi Shinko Kagaku K.K.) and 1.5 parts by weight of sulfur as shown in Table 4 was kneaded by means of a 6-inch open roll, to obtain an unvulcanized rubber blend.

The vulcanizing rate of the rubber blend was evaluated in the same manner as in Example 1. As a result, T90 was 6.3 minutes as shown in Example 4.

Further, the unvulcanized rubber blend having a composition shown in Table 4 was press molded under the conditions of a temperature of 160° C. and a molding time of T90 (minute)+5 minutes. T90 (minute) of the unvulcanized rubber blend, and modulus at 100%, 200% and 300% (M100, M200 and M300), tensile strength ($T_B$), elongation ($E_B$) and 5 hardness ($H_S$) of the resulting vulcanized rubber were measured in the same manner as in Example 1.

The results are set forth in Table 5.

TABLE 4

| Composition of unvulcanized rubber blend | part(s) by weight |
|---|---|
| Ethylene-propylene-EMN copolymer | 100 |
| Zinc white No. 1 | 5 |
| Stearic acid | 1 |
| N330 (Seast 3, from Tokai Carbon K.K.) | 80 |
| Oil (Sunthene 4240, from Sun Oil K.K.) | 50 |
| Vulcanization accelerator A (Nocceler TT, from Ouchi Shinko Kagaku K.K.) | 1.0 |
| Vulcanization accelerator B (Nocceler M, from Ouchi Shinko Kagaku K.K.) | 0.5 |
| Sulfur | 1.5 |

Example 5

Polymerization was carried out in the same manner as described in Example 4 except that the components were continuously fed to the polymerizer so that the concentrations of EMN, zirconium and aluminum became 250 mmol/l, 0.04 mmol/l and 20 mmol/l, respectively, the feed rates of ethylene and propylene were varied to 120 l/hr and 120 l/hr, respectively, and the polymerization temperature was varied to 10° C., to obtain an ethylene-propylene-EMN copolymer in an amount of 62 g per hour.

In the ethylene-propylene-EMN copolymer, the ethylene units were contained in amounts of 65.6% by mol, the propylene units were contained in amounts of 33.0% by mol, the EMN units were contained in amounts of 1.4% by mol, and the molar ratio of the ethylene units to the propylene units was 67/33 (ethylene units/propylene units). The intrinsic viscosity ($\eta$) of this copolymer was 1.7 dl/g.

Then, a rubber blend (rubber composition) was prepared in the same manner as described in Example 4 except that the ethylene-propylene-EMN copolymer obtained above was used in place of the ethylene-propylene-EMN copolymer obtained in Example 4. The vulcanizing rate of the rubber blend and the vulcanization properties of the resulting vulcanized rubber were evaluated.

The results are set forth in Table 5.

Example 6
(Preparation of catalyst solution)

To a glass flask thoroughly purged with nitrogen was introduced 5.6 mg of rac-dimethylsilylenebis{1-(2-methyl-4,5-benzoindenyl)}zirconium dichloride, and thereto was added 2.6 ml of a toluene solution of methylaluminoxane (Al=1.12 mol/liter) to obtain a catalyst solution.
(Polymerization)

To a 2-liter stainless steel autoclave thoroughly purged with nitrogen were introduced 900 ml of heptane and 25 ml of EMN (4-ethylidene-8-methyl-1,7-nonadiene), and was further introduced propylene so that the pressure in the system became 3.4 kg/cm$^2$-G at 50° C. Then, ethylene was fed until the pressure became 8 kg/cm$^2$-G. Thereafter, 1 mmol of triisobutylaluminum and 0.54 ml (0.002 mmol in terms of Zr) of the catalyst component prepared above was pressed into the system with nitrogen to initiate the polymerization. Then, only ethylene was continuously fed to keep the total pressure at 8 kg/cm$^2$-G, and the polymerization was continued at 50° C. for 15 minutes. A small amount of ethanol was added to the system to terminate the polymerization, followed by purging of the unreacted monomer.

The polymer solution obtained was introduced into a large excess amount of methanol to precipitate a polymer. The polymer was recovered by filtration and mixed with stabilizers (30 mg of Irganox 1010 available from Ciba-Geigy and 60 mg of Mark 329K available from Asahi Denka K.K.). The mixture was dried overnight at 120° C. under reduced pressure.

As a result, 57 g of an ethylene-propylene-EMN copolymer containing 61.8% by mol of ethylene units, 36.6% by mol of propylene units and 1.6% by mol of EMN units and having a molar ratio of the ethylene units to the propylene units of 62.8/37.2 (ethylene units/propylene units) and an intrinsic viscosity ($\eta$) of 2.1 dl/g was obtained.

Then, a rubber blend (rubber composition) was prepared in the same manner as described in Example 4 except that the ethylene-propylene-EMN copolymer obtained above was used in place of the ethylene-propylene-EMN copolymer obtained in Example 4. The vulcanizing rate of the rubber blend and the vulcanization properties of the resulting vulcanized rubber were evaluated.

The results are set forth in Table 5.

Example 7

Polymerization was carried out in the same manner as described in Example 6 except that 1-butene was introduced in place of propylene so that the pressure became 3.5 kg/cm$^2$-G at 50° C. and the polymerization time was varied to 30 minutes.

As a result, 48 g of an ethylene-1-butene-EMN copolymer containing 66.5% by mol of ethylene units, 31.9% by mol of 1-butene units and 1.5% by mol of EMN units and having a molar ratio of the ethylene units to the 1-butene units of 67.6/32.4 (ethylene units/1-butene units) and an intrinsic viscosity ($\eta$) of 1.6 dl/g was obtained.

Then, a rubber blend (rubber composition) was prepared in the same manner as described in Example 4 except that the ethylene-butene-EMN copolymer obtained above was used in place of the ethylene-propylene-EMN copolymer obtained in Example 4. The vulcanizing rate of the rubber blend and the vulcanization properties of the resulting vulcanized rubber were evaluated.

The results are set forth in Table 5.

Example 8

Polymerization was carried out in the same manner as described in Example 6 except that the amount of heptane used was varied to 500 ml, 500 ml of 1-octene was introduced in place of propylene and the polymerization time was varied to 30 minutes.

As a result, 45 g of an ethylene-1-octene-EMN copolymer containing 64.3% by mol of ethylene units, 33.6% by mol of 1-octene units and 2.1% by mol of EMN units and having a molar ratio of the ethylene units to the 1-octene units of 65.7/34.3 (ethylene units/1-octene units) and an intrinsic viscosity ($\eta$) of 1.5 d/g was obtained.

Then, a rubber blend (rubber composition) was prepared in the same manner as described in Example 4 except that the ethylene-1-octene-EMN copolymer obtained above was used in place of the ethylene-propylene-EMN copolymer obtained in Example 4. The vulcanizing rate of the rubber blend and the vulcanization properties of the resulting vulcanized rubber were evaluated.

The results are set forth in Table 5.

Example 9
(Preparation of catalyst solution)

To a glass flask thoroughly purged with nitrogen was introduced 6.5 mg of rac-dimethylsilylenebis{1-(2-methyl-4-phenyl-indenyl)}zirconium dichloride, and thereto was added 3.1 ml of a toluene solution of methylaluminoxane (Al=1.12 mol/liter) to obtain a catalyst solution.

(Polymerization)

Polymerization was carried out in the same manner as described in Example 6 except that the amount of EMN used was varied to 20 ml, the pressure of propylene was varied to 2.3 kg/cm$^2$-G, the catalyst solution prepared above was used in an amount of 0.60 ml (0.002 mmol in terms of Zr), and the polymerization time was varied to 10 minutes.

As a result, 61 g of an ethylene-propylene-EMN copolymer containing 64.8% by mol of ethylene units, 33.9% by mol of propylene units and 1.3% by mol of EMN units and having a molar ratio of the ethylene units to the propylene units of 65.7/34.3 (ethylene units/propylene units) and an intrinsic viscosity ($\eta$) of 1.8 dl/g was obtained.

Then, a rubber blend (rubber composition) was prepared in the same manner as described in Example 4 except that the ethylene-propylene-EMN copolymer obtained above was used in place of the ethylene-propylene-EMN copolymer obtained in Example 4. The vulcanizing rate of the rubber blend and the vulcanization properties of the resulting vulcanized rubber were evaluated.

The results are set forth in Table 5.

Comparative Example 2

In a 2-liter polymerizer equipped with a stirring blade, copolymerization reaction of ethylene, propylene and 5-ethylidene-2-norbornene (ENB) was continuously carried out.

The copolymerization reaction was conducted in a manner described below.

To the polymerizer were continuously fed, from the top thereof, a hexane solution of ENB (7.1 g/l) at a feed rate of 0.5 l/hr, a hexane solution of VO(OC$_2$H$_5$)Cl$_2$ (0.8 mmol/l) as a catalyst at a feed rate of 0.5 l/hr, a hexane solution of ethylaluminum sesquichloride (Al(C$_2$H$_5$)$_{1.5}$Cl$_{1.5}$) (8.0 mmol/l) as a cocatalyst at a feed rate of 0.5 l/hr, and hexane at a feed rate of 0.5 l/hr.

On the other hand, the polymer solution was continuously drawn out from the top of the polymerizer so that the polymer solution in the polymerizer was kept constant in an amount of 1 liter. Further, to the polymerization system were fed ethylene at a feed rate of 120 l/hr, propylene at a feed rate of 180 l/hr and hydrogen at a feed rate of 5 l/hr using bubble tube. The copolymerization reaction was carried out at 30° C. by circulating a cooling medium through a jacket provided outside the polymerizer.

Through the polymerization reaction under the above conditions, a polymer solution containing an ethylene-propylene-ENB copolymer was obtained.

The polymer solution was deashed using hydrochloric acid and then introduced into a large amount of methanol to precipitate the polymer (ethylene-propylene-ENB copolymer), followed by vacuum drying at 100° C. for 24 hours.

Thus, an ethylene-propylene-ENB copolymer was obtained in an amount of 64.8 g per hour.

In the ethylene-propylene-ENB copolymer, the ethylene units were contained in amounts of 66.8% by mol, the propylene units were contained in amounts of 31.4% by mol, the ENB units were contained in amounts of 1.8% by mol, and the molar ratio of the ethylene units to the propylene units was 68/32 (ethylene units/propylene units). The intrinsic viscosity ($\eta$) of this ethylene-propylene-ENB copolymer was 2.2 dl/g.

Then, a rubber blend was prepared in the same manner as described in Example 4 except that the ethylene-propylene-ENB copolymer obtained above was used in place of the copolymer obtained in Example 4. The vulcanizing rate of the rubber blend and the vulcanization properties of the resulting vulcanized rubber were evaluated.

The results are set forth in Table 5.

TABLE 5

| Example No. | Ex. 4 | Ex. 5 | Ex. 6 | Ex. 7 | Ex. 8 | Ex. 9 | Comp. Ex. 2 |
|---|---|---|---|---|---|---|---|
| Vulcanization Properties | | | | | | | |
| M100 (kgf/cm$^2$) | 29 | 31 | 30 | 32 | 29 | 30 | 30 |
| M200 (kgf/cm$^2$) | 70 | 73 | 74 | 77 | 72 | 70 | 74 |
| M300 (kgf/cm$^2$) | 85 | 89 | 95 | 110 | 87 | 85 | 117 |
| T$_B$ (kgf.cm$^2$) | 137 | 131 | 151 | 162 | 129 | 127 | 168 |
| E$_B$ (kgf.cm$^2$) | 380 | 310 | 480 | 490 | 310 | 480 | 400 |
| H$_S$ (JIS A) | 66 | 67 | 66 | 68 | 67 | 68 | 68 |
| Vulcanizing Rate | | | | | | | |
| T90 (min.) | 6.3 | 5.0 | 4.6 | 5.1 | 5.4 | 4.8 | 11.2 |

Example 10

To a 2-liter stainless steel autoclave thoroughly purged with nitrogen were introduced 900 ml of heptane and 20 ml of EMN (4-ethylidene-8-methyl-1,7-nonadiene), and was further introduced propylene so that the pressure in the system became 3.5 kg/cm$^2$-G. Then, ethylene was introduced until the pressure became 8 kg/cm$^2$-G.

Thereafter, 1 mmol of triisobutylaluminum, 0.004 mmol of triphenylcarbeniumtetrakis(pentafluorophenyl)borate and 0.001 mmol of (dimethyl(t-butylamide) (tetramethylcyclopentadienyl)silane)titanium dichloride were pressed into the system with nitrogen to initiate the polymerization. Then, only ethylene was continuously fed so that the total pressure was kept at 8kg/cm$^2$-G, and the polymerization was continued at 80° C. for 10 minutes.

The subsequent operation was carried out in the same manner as described in Example 6.

As a result, 55 g of an ethylene-propylene-EMN copolymer containing 63.5% by mol of ethylene units, 35.0% by mol of propylene units and 1.5% by mol of EMN units and having a molar ratio of the ethylene units to the propylene units of 64.5/35.5 (ethylene units/propylene units) and an intrinsic viscosity ($\eta$) of 3.1 dl/g was obtained.

The vulcanizing rate of the copolymer was evaluated in the same manner as described in Example 4. As a result, T90 was 5.0 minutes.

Reference Example 4
(Synthesis of 13-ethyl-9-methyl-1,9,12-pentadecatriene (EMPDT))

(p=0, q=1, f=5, g=1, total number of hydrogen atoms directly bonded to the carbon atoms adjacent to all the carbon-to-carbon double bonds: 13)

(EMPDT) 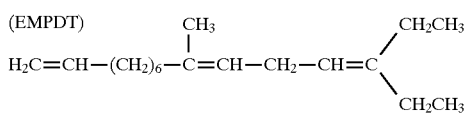

To a 1-liter three-necked flask equipped with a stirrer, a Dimroth condenser, a dropping funnel and a thermometer were introduced 24 g (1.0 g.atom) of flaky metallic magnesium, 200 ml of anhydrous diethyl ether and 200 mg of 1,2-dibromoethane with stirring in a nitrogen atmosphere, and thereto was dropwise added a small amount of a solution of allyl bromide (127 g, 1.05 mol) in anhydrous diethyl ether (200 ml).

After the exothermic reaction of the content in the flask is initiated and allylmagnesium bromide began to be produced, 300 ml of anhydrous diethyl ether was added, and the rest of the anhydrous diethyl ether solution of allyl bromide was dropwise added under cooling in an ice bath over a period of 1.5 hours (flask internal temperature: not higher than 5° C.). The mixture was further stirred for 0.5 hour to obtain an allylmagnesium bromide solution. The insoluble portion remaining in the allylmagnesium bromide solution was removed by decantation, and the solution was transferred into a 2-liter three-necked flask.

With cooling the three-necked flask in an ice bath, to the flask was dropwise added a solution of 1-bromo-10-ethyl-6-methyl-6,9-dodecadiene (201 g, 0.70 mol) in anhydrous diethyl ether (200 ml) at an internal temperature of not higher than 5° C. over a period of 2 hours.

After the dropwise addition was completed, the mixture was further stirred at room temperature for 6 hours. While the reaction mixture was cooled in an ice bath, to the mixture was dropwise added slowly a saturated ammonium chloride aqueous solution and were further added diethyl ether and water to separate the mixture into an organic phase and an aqueous phase.

The organic phase was washed with a saturated sodium hydrogencarbonate solution and a saturated saline solution and then dried over anhydrous magnesium sulfate.

The solvent was evaporated and the residue was subjected to vacuum distillation, to obtain the aimed product (134 g of 13-ethyl-9-methyl-1,9,12-pentadecatriene) (yield: 77%, based on 1-bromo-10-ethyl-6-methyl-6,9-dodecadiene).

State: colorless, oily; Boiling point: 125°–127° C./1 mmHg; FD-MS: m/z 248 (M+); $^1$H-NMR spectrum (CDCl$_3$ solution): 1.05 (6H, triplet, J=7 Hz); 1.60 (3H, singlet); 1.2–1.5 (8H, multiplet); 2.0–2.2 (8H, multiplet); 2.75 (2H, triplet, J=7 Hz); 4.95 (1H, doublet, J=10 Hz); 5.00 (1H, doublet, J=17 Hz); 5.10 (2H, multiplet); 5.80 (1H, multiplet)

The reaction formula of the above reaction is described below.

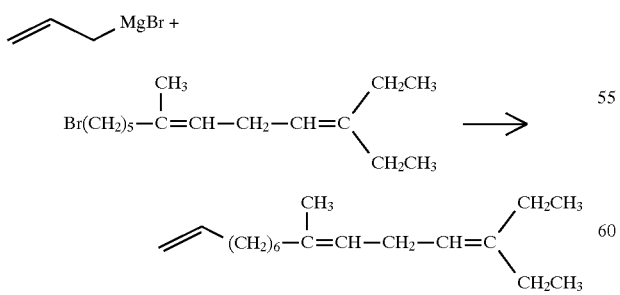

Example 11

Polymerization was carried out in the same manner as described in Example 6 except that 35 ml of the EMPDT (13-ethyl-9-methyl-1,9,12-pentadecatriene) obtained above was used in place of EMN.

As a result, 45 g of an ethylene-propylene-EMPDT copolymer containing 62.8% by mol of ethylene units, 35.9% by mol of propylene units and 1.3% by mol of EMPDT units and having a molar ratio of the ethylene units to the propylene units of 63.6/36.4 (ethylene units/propylene units) and an intrinsic viscosity ($\eta$) of 1.9 dl/g was obtained.

The vulcanizing rate of the copolymer was evaluated in the same manner as described in Example 4. As a result, T90 was 6.2 minutes.

Reference Example 5

(Synthesis of 5,9,13-trimethyl-1,4,8,12-tetradecatetraene (MTDT))
(p=0, q=1, f=0, g=2, total number of hydrogen atoms directly bonded to the carbon atoms adjacent to all the carbon-to-carbon double bonds: 22)

(MTDT) 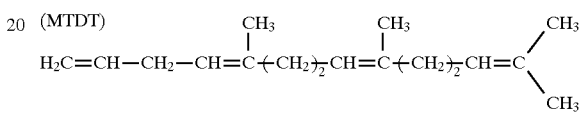

To a 1-liter three-necked flask equipped with a stirrer, a Dimroth condenser, a dropping funnel and a thermometer was introduced 500 ml (0.435 mol) of an anhydrous tetrahydrofuran solution of vinyl magnesium (0.87 mol/l) in a nitrogen atmosphere, and the flask was cooled in an ice bath. Then, 100 ml of an anhydrous tetrahydrofuran solution of farnesyl bromide (100 g, 0.35 mol) was dropwise added with stirring over a period of 30 minutes, followed by stirring at room temperature for 5 hours.

With cooling the reaction mixture in an ice bath, to the mixture was dropwise added slowly a saturated ammonium chloride aqueous solution and were further added diethyl ether and water to separate the mixture into an organic phase and an aqueous phase. The organic phase was washed with a saturated sodium hydrogencarbonate solution and a saturated saline solution and then dried over anhydrous magnesium sulfate. The solvent was evaporated and the residue was subjected to vacuum distillation, to obtain 26 g of the aimed product (5,9,13-trimethyl-1,4,8,12-tetradecatetraene) (yield: 32%, based on farnesyl bromide).

State: colorless, oily; Boiling point: 117°–120° C./1 mmHg; FD-MS spectrum: 232 (M$^+$); $^1$H-NMR spectrum (CDCl$_3$ solution): 1.60 (6H, singlet); 1.68 (6H, singlet); 2.05 (8H, multiplet); 2.75 (2H, triplet, J=7 Hz); 4.96 (1H, doublet, J=10 Hz); 5.01 (1H, doublet, J=17 Hz); 5.10 (3H, multiplet); 5.80 (1H, multiplet)

The reaction formula of the above reaction is described below.

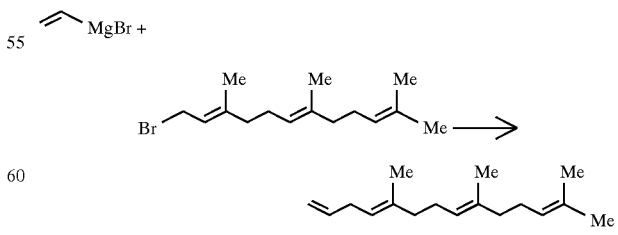

Example 12

Polymerization was carried out in the same manner as described in Example 6 except that 35 ml of the MTDT (5,9,13-trimethyl-1,4,8,12-tetradecatetraene) obtained above was used in place of the EMN.

As a result, 42 g of an ethylene-propylene-MTDT copolymer containing 61.0% by mol of ethylene units, 37.6% by mol of propylene units and 1.4 by mol of MTDT units and having a molar ratio of the ethylene units to the propylene units of 61.9/38.1 (ethylene units/propylene units) and an intrinsic viscosity (η) of 2.0 dl/g was obtained.

The vulcanizing rate of the copolymer was evaluated in the same manner as described in Example 4. As a result, T90 was 5.8 minutes.

Reference Example 6
(Synthesis of 8,14,15-trimethyl-1,7,14-hexadecatriene (MHDT))
(p=0, q=1, f=3, g=5, total number of hydrogen atoms directly bonded to the carbon atoms adjacent to all the carbon-to-carbon double bonds: 20)

(MHDT)

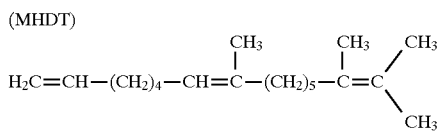

To a 1-liter three-necked flask equipped with a stirrer, a Dimroth condenser, a dropping funnel and a thermometer were introduced 24 g (1.0 g.atom) of flaky metallic magnesium, 200 ml of anhydrous diethyl ether and 200 mg of 1,2-dibromoethane with stirring in a nitrogen atmosphere, and thereto was dropwise added a small amount of a solution of allyl bromide (127 g, 1.05 mol) in anhydrous diethyl ether (200 ml).

After the exothermic reaction of the content in the flask was initiated and allylmagnesium bromide began to be produced, 370 ml of anhydrous diethyl ether was added, and the rest of the anhydrous diethyl ether solution of allyl bromide was dropwise added under cooling in an ice bath over a period of 2 hours (flask internal temperature: not higher than 5° C.). The mixture was further stirred for 0.5 hour to obtain an allylmagnesium bromide solution. The insoluble portion remaining in the allylmagnesium bromide solution was removed by decantation, and the solution was transferred into a 2-liter three-necked flask in a nitrogen atmosphere.

With cooling the three-necked flask in an ice bath, to the flask was dropwise added a solution of 1-bromo-5,11,12-trimethyl-4,11-tridecadiene (211 g, 0.70 mol) in anhydrous diethyl ether (200 ml) at an internal temperature of not higher than 5° C. over a period of 2 hours.

After the dropwise addition was completed, the mixture was further stirred at room temperature for 6 hours. While the reaction mixture was cooled in an ice bath, to the mixture was dropwise added slowly a saturated ammonium chloride aqueous solution and were further added diethyl ether and water to separate the mixture into an organic phase and an aqueous phase.

The organic phase was washed with a saturated sodium hydrogencarbonate solution and a saturated saline solution and then dried over anhydrous magnesium sulfate.

The solvent was evaporated and the residue was subjected to vacuum distillation, to obtain 130 g of the aimed product (8,14,15-trimethyl-1,7,14-hexadecatriene) (yield: 71%, based on 1-bromo-5,11,12-trimethyl-4,11-tridecadiene).

The state and the properties of the 8,14,15-trimethyl-1,7, 14-hexadecatriene are described below.

State: colorless, oily; Boiling point: 130°–133° C./1 mmHg FD-MS: m/z 262 ($M^+$); $^1$H-NMR spectrum ($CDCl_3$ solution): 1.60 (3H, singlet); 1.61 (3H, singlet); 1.65 (3H, singlet); 1.68 (3H, singlet); 1.2–1.5 (10H, multiplet); 2.0 (8H, multiplet); 4.95 (1H, doublet, J=10 Hz); 5.02 (1H, doublet, J=17 Hz); 5.17 (1H, multiplet); 5.80 (1H, multiplet)

The reaction formula of the above reaction is described below.

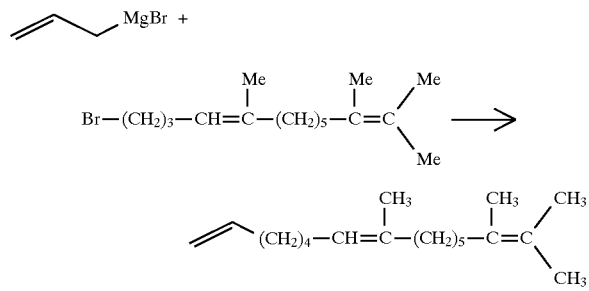

Example 13

Polymerization was carried out in the same manner as described in Example 6 except that 35 ml of the MHDT (8,14,15-trimethyl-1,7,14-hexadecatriene) obtained above was used in place of the EMN.

As a result, 49 g of an ethylene-propylene-MHDT copolymer containing 63.0% by mol of ethylene units, 35.8% by mol of propylene units and 1.2% by mol of MHDT units and having a molar ratio of the ethylene units to the propylene units of 63.8/36.2 (ethylene units/propylene units) and an intrinsic viscosity (η) of 1.8 dl/g was obtained.

The vulcanizing rate of the copolymer was evaluated in the same manner as described in Example 4. As a result, T90 was 6.0 minutes.

Reference Example 7
(Synthesis of 4-ethylidene-12-methyl-1,11-pentadecadiene (EMPD))
(p=1, q=0, f=1, g=5, total number of hydrogen atoms directly bonded to the carbon atoms adjacent to all the carbon-to-carbon double bonds: 14)

(EMPD)

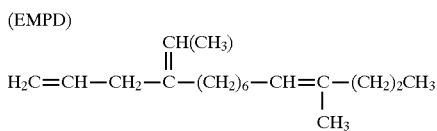

In a nitrogen atmosphere, to a 300-ml stainless steel (SUS316) autoclave were introduced 110 g (0.5 mol) of 11-methyl-3-methylene-1,10-tetradecadiene, 264 mg (0.5 mmol) of a complex preliminarily isolated as (1,2-bis (diphenylphosphino)ethane)cobalt(II) chloride and 10 ml of a toluene solution of triethylaluminum (triethylaluminum: 10 mmol, concentration: 1 mol/liter), and they were stirred at room temperature for 30 minutes.

The autoclave was sealed and then connected with an ethylene bomb, through which ethylene was introduced, so as to pressurize the autoclave up to 10 kg/cm$^2$. Thereafter, the autoclave was heated slowly to 90° C., and ethylene was intermittently replenished two times to perform the reaction at 90° C. for 4 hours in total.

After cooling, the autoclave was released, and the reaction mixture obtained was poured into 100 ml of water to separate the mixture into an organic phase and an aqueous phase. From the organic phase, a low-boiling substance portion was removed by means of an evaporator, followed by vacuum precision distillation of 20 plates.

Thus, 88 g of the aimed product (4-ethylidene-12-methyl-1,11-pentadecadiene) was obtained (yield: 71%) Further, 22 g of 5,13-dimethyl-1,4,12-hexadecatriene (isomer) was produced as a subproduct (yield: 18%).

The physiochemical data of the 4-ethylidene-12-methyl-1,11-pentadecadiene are described below.

State: colorless, oily; Boiling point: 120°–125° C./1 mmHg; Result of FD-MS analysis: m/z 248 (M$^+$: molecule ion peak); $^1$H-NMR spectrum (CDCl$_3$ solution): 0.90 (3H, triplet, J=7 Hz); 1.2–1.5 (10H, multiplet); 1.60 (3H, doublet, J=7 Hz); 1.70 (3H, triplet, J=7 Hz); 2.0 (6H, multiplet); 2.80 (2H, doublet, J=7 Hz); 4.9–5.2 (3H, multiplet); 5.28 (1H, quartet, J=7 Hz); 5.77 (1H, multiplet);

The reaction formula of the above reaction is described below.

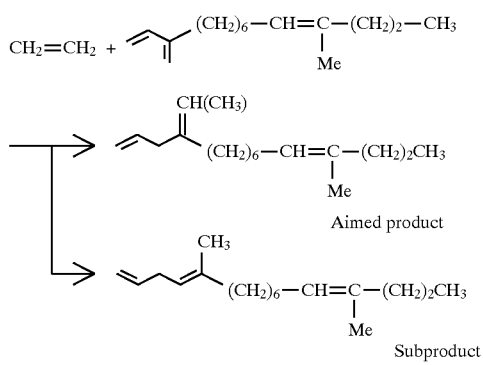

Example 14

Polymerization was carried out in the same manner as described in Example 6 except that 35 ml of the EMPD (4-ethylidene-12-methyl-1,11-pentadecadiene) obtained above was used in place of the EMN.

As a result, 47 g of an ethylene-propylene-EMPD copolymer containing 60.9% by mol of ethylene units, 37.6% by mol of propylene units and 1.5% by mol of EMPD units and having a molar ratio of the ethylene units to the propylene units of 61.8/38.2 (ethylene units/propylene units) and an intrinsic viscosity ($\eta$) of 1.9 dl/g was obtained.

The vulcanizing rate of the copolymer was evaluated in the same manner as described in Example 4. As a result, T90 was 5.7 minutes.

Reference Example 8
(Preparation of catalyst)

In an argon atmosphere, to a 300-ml flask equipped with a magnetic stirrer were introduced 1.05 g (2.00 mmol) of (1,2-bis(diphenylphosphino)ethane)cobalt(II) chloride and 100 ml of anhydrous decane, and they were stirred at 25° C. for 30 minutes. Then, at the same temperature, to the mixture was further added 100 ml of a hexane solution of triethylaluminum (triethylaluminum: 100 mmol, concentration: 1 mol/liter), and the mixture was further stirred for 2 hours to prepare a catalyst.
(Synthesis of 4-ethylidene-8,12-dimethyl-1,7,11-tridecatriene (EDT, the aforesaid compound (47)))
(p=1, q=1, f=2, g=2, total number of hydrogen atoms directly bonded to the carbon atoms adjacent to all the carbon-to-carbon double bonds: 22)

To a 1-liter stainless steel (SUS316) autoclave were introduced 204.3 g (1,00 mol) of 7,11-dimethyl-3-methylene-1,6,10-dodecatriene (β-farnesene, available from Tokyo Kasei Kogyo K.K.) and the whole amount of the catalyst prepared above, and the autoclave was sealed. Then, ethylene was fed until the pressure in the autoclave became 10 kg/cm$^2$. Thereafter, the autoclave was heated to 95° C. and ethylene was intermittently replenished eight times to perform reaction for 15 hours in total.

After the reaction was completed, the autoclave was cooled and released. The reaction mixture obtained was poured into 300 ml of water to separate the mixture into an organic phase and an aqueous phase. From the organic phase, a low-boiling substance portion was removed by means of an evaporator, followed by vacuum precision distillation using a packed column of 20 plates.

Thus, 153 g of the aimed product (EDT) was obtained as a colorless liquid (yield: 66%). Further, 26 g of 5,9,13-trimethyl-1,4,8,12-tetradecatriene was obtained as a subproduct (yield: 11%).

Boiling point: 116°–125° C./2 mmHg; (boiling point of a mixture of 4-ethylidene-8,12-dimethyl-1,7,11-tridecatriene and 5,9,13-trimethyl-1,4,8,12-tetradecatriene); GC-MS: 232 (M$^+$: molecule ion peak), 217, 189, 163, 148, 121, 107, 95, 81, 69; Infrared absorption spectrum (neat, cm$^{-1}$); 3070, 2960, 2920, 2850, 1670, 1640, 1440, 1380, 1235, 1150, 1105, 995, 960, 910, 830; Proton NMR spectrum (90 MHz, bichloroform solution, ppm); 1.58 (3H, doublet, J=7 Hz); 1.60 (6H, singlet); 1.69 (3H, singlet); 2.01 (8H, multiplet); 2.78 (2H, doublet, J=7 Hz); 4.9–6.0 (6H, multiplet)

Reference Example 9

A catalyst was prepared in the same manner as described in Reference Example 8 except that 0.26 g (2.00 mmol) of anhydrous cobalt(II) chloride was suspended at 25° C. in 100 ml of anhydrous decane in place of the (1,2-bis(diphenylphosphino)ethane)cobalt(II) chloride preliminarily prepared, then to the suspension was added 1.59 g (4.00 mmol) of 1,2-bis(diphenylphosphino)ethane was added, the mixture was stirred at 25° C. for 2 hours, and to the mixture was added 100 ml of a hexane solution of triethylaluminum (triethylaluminum: 100 mmol, concentration: 1 mol/liter) at 25° C., followed by stirring for 2 hours.

Using the catalyst obtained above, the reaction was carried out in the same manner as described in Reference Example 8.

As a result, 4-ethylidene-8,12-dimethyl-1,7,11-tridecatriene was obtained (yield: 60%), and 5,9,13-trimethyl-1,4,8,12-tetradecatriene was obtained as a subproduct (yield: 8%).

Reference Example 10

The reaction was carried out in the same manner as described in Reference Example 8 except that 1.05 g (2.00 mmol) of (1,2-bis(diphenylphosphino)ethane)nickel(II) chloride preliminarily prepared was used in place of the (1,2-bis(diphenylphosphino)ethane)cobalt(II) chloride preliminarily prepared.

As a result, 4-ethylidene-8,12-dimethyl-1,7,11-tridecatriene was obtained (yield: 43%), and 5,9,13-trimethyl-1,4,8,12-tetradecatriene was obtained as a subproduct (yield: 7%)

What is claimed is:

1. An unsaturated copolymer of ethylene wherein (A) said copolymer is a random copolymer of:
 (i) ethylene,
 (ii) an α-olefin of 3 to 20 carbon atoms, and
 (iii) at least one straight chain or branched chain nonconjugated triene or tetraene having one vinyl group in the molecule represented by the following formula (H-1)

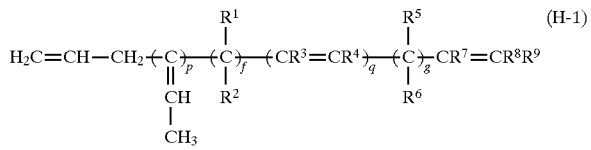

wherein
p and q are each 0 or 1, with the proviso that each of p and q is not 0 at the same time,
f is an integer of 0 to 5, with the proviso that when p and q are each 1, f is not 0,
g is an integer of 2 to 6,
$R^1$, $R^2$, $R^3$, $R^4$, $R^5$, $R^6$ and $R^7$ are each hydrogen or an alkyl group of 1 to 5 carbon atoms,
$R^8$ is an alkyl group of 1 to 5 carbon atoms, and
$R^9$ is hydrogen, an alkyl group of 1 to 5 carbon atoms or a group represented by the formula $-(CH_2)_n-CR^{10}=CR^{11}R^{12}$, where n is an integer of 1 to 5, $R^{10}$ and $R^{11}$ are each hydrogen or an alkyl group of 1 to 5 carbon atoms, and $R^{12}$ is alkyl group of 1 to 5 carbon atoms, with the proviso that when p and q are each 1, $R^9$ is hydrogen or an alkyl group of 1 to 5 carbon atoms;

(B) said copolymer comprises:
 (i) constituent units from said ethylene in an amount of 30 to 92% by mol,
 (ii) constituent units from said α-olefin of 3 to 20 carbon atoms in an amount of 6 to 70% by mol, and
 (iii) constituent units from said nonconjugated triene or tetraene, represented by the following formula (H-2)

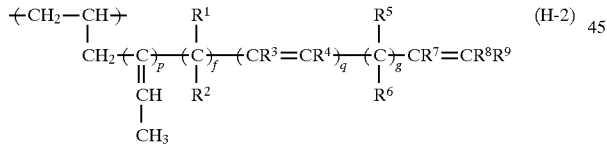

wherein p, q, f, g and $R^1$ to $R^9$ have the same meanings as described for said formula (H-1), in an amount of 0.1 to 30% by mol, in which
 (iv) a molar ratio of said constituent units from said ethylene (i) to said constituent units from said α-olefin of 3 to 20 carbon atoms (ii) is in the range of 40/60 to 92/8; and (C) said copolymer has an intrinsic viscosity (η), as measured in decahydronaphthalene at 135° C., of 0.05 to 10 dl/g.

2. The unsaturated copolymer of ethylene as claimed in claim 1, wherein the nonconjugated triene or tetraene (iii) in (A) is represented by the following formula (Ia), and the constituent units derived from the nonconjugated triene or tetraene (iii) in (B) are represented by the following formula (IIa):

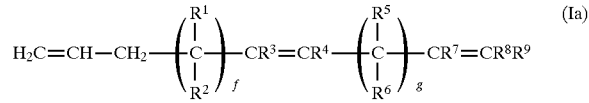

wherein f is an integer of 0 to 5, g is an integer of 2 to 6; $R^1$, $R^2$, $R^3$, $R^4$, $R^5$, $R^6$ and $R^7$ are each hydrogen or an alkyl group of 1 to 5 carbon atoms; $R^8$ is an alkyl group of 1 to 5 carbon atoms; and $R^9$ is hydrogen, an alkyl group of 1 to 5 carbon atoms or a group represented by the formula $-(CH_2)_n-CR^{10}=CR^{11}R^{12}$, where n is an integer of 1 to 5, $R^{10}$ and $R^{11}$ are each hydrogen or an alkyl group of 1 to 5 carbon atoms, and $R^{12}$ is an alkyl group of 1 to 5 carbon atoms;

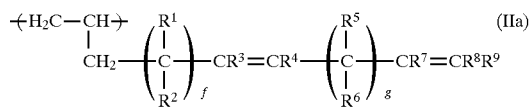

wherein f, g and $R^1$ to $R^9$ have the same meanings as described in the formula (Ia).

3. The unsaturated copolymer of ethylene as claimed in claim 2, wherein $R^1$, $R^2$, $R^5$ and $R^6$ in the formulas (Ia) and (IIa) are each hydrogen.

4. The unsaturated copolymer of ethylene as claimed in claim 1, wherein the nonconjugated triene or tetraene (iii) in (A) is represented by the following formula (Ib), and the constituent units derived from the nonconjugated triene or tetraene (iii) in (B) are represented by the following formula (IIb):

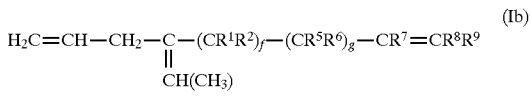

wherein f is an integer of 0 to 5; g is an integer of 2 to 6; $R^1$, $R^2$, $R^5$, $R^6$ and $R^7$ are each hydrogen or an alkyl group of 1 to 5 carbon atoms; $R^8$ is an alkyl group of 1 to 5 carbon atoms; and $R^9$ is hydrogen, an alkyl group of 1 to 5 carbon atoms or a group represented by the formula $-(CH_2)_n-CR^{10}=CR^{11}R^{12}$, where n is an integer of 1 to 5, $R^{10}$ and $R^{11}$ are each hydrogen or an alkyl group of 1 to 5 carbon atoms, and $R^{12}$ is an alkyl group of 1 to 5 carbon atoms;

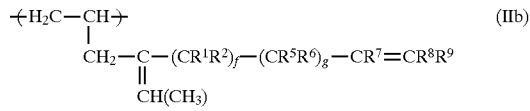

wherein f, g, $R^1$, $R^2$ and $R^5$ to $R^9$ have the same meanings as described in the formula (Ib).

5. The unsaturated copolymer of ethylene as claimed in claim 4, wherein $R^1$, $R^2$, $R^5$ and $R^6$ in the formulas (Ib) and (IIb) are each hydrogen.

6. The unsaturated copolymer of ethylene as claimed in claim 4, wherein the nonconjugated tetraene (iii) in (A) is represented by the following formula (Ib'), and the constituent units derived from the nonconjugated tetraene (iii) in (B) is represented by the following formula (IIb'):

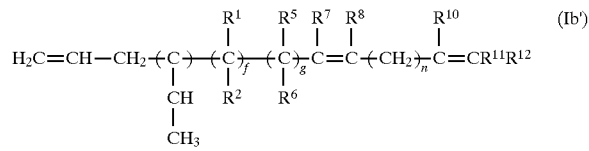

wherein f is an integer of 0 to 5, g is an integer of 2 to 6; $R^1$, $R^2$, $R^5$, $R^6$ and $R^7$ are each hydrogen or an alkyl group of 1 to 5 carbon atoms; $R^8$ is an alkyl group of 1 to 5 carbon atoms; n is an integer of 1 to 5; $R^{10}$ and $R^{11}$ are each hydrogen or an alkyl group of 1 to 5 carbon atoms, and $R^{12}$ is an alkyl group of 1 to 5 carbon atoms;

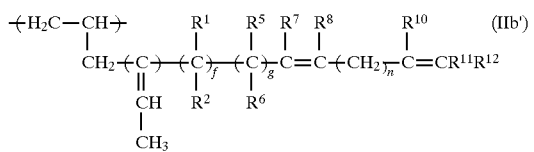 (IIb')

wherein f, g, n, $R^1$, $R^2$, $R^5$ to $R^8$ and $R^{10}$ to $R^{12}$ have the same meanings as described in the formula (Ib').

7. The unsaturated copolymer of ethylene as claimed in claim 6, wherein $R^1$, $R^2$, $R^5$ and $R^6$ in the formulas (Ib') and (IIb') are each hydrogen.

8. The unsaturated copolymer of ethylene as claimed in claim 4, wherein the nonconjugated triene or tetraene (iii) in (A) is represented by the following formula (Ic), and the constituent units derived from the nonconjugated triene or tetraene (iii) in (B) are represented by the following formula (IIc):

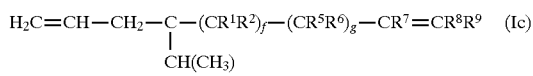

wherein f is an integer of 0 to 5; g is an integer of 2 to 6; $R^1$, $R^2$, $R^5$, $R^6$ and $R^7$ are each hydrogen or an alkyl group of 1 to 5 carbon atoms; $R^8$ is an alkyl group of 1 to 5 carbon atoms; and $R^9$ is hydrogen or an alkyl group of 1 to 5 carbon atoms;

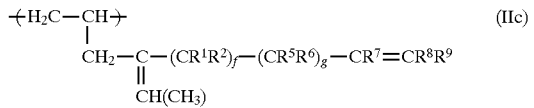 (IIc)

wherein f, g, $R^1$, $R^2$ and $R^5$ to $R^9$ have the same meanings as described in the formula (Ic).

9. The unsaturated copolymer of ethylene as claimed in claim 8, wherein $R^1$, $R^2$, $R^5$ and $R^6$ in the formulas (Ic) and (IIc) are each hydrogen.

10. The unsaturated copolymer of ethylene as claimed in claim 1, wherein the total number of the hydrogen atoms directly bonded to the carbon atoms adjacent to all the carbon-to-carbon double bonds in the nonconjugated triene or tetraene (iii) in (A) is 9 to 33.

11. The unsaturated copolymer of ethylene as claimed in claim 1, wherein the total number of the hydrogen atoms directly bonded to the carbon atoms adjacent to all the carbon-to-carbon double bonds in the nonconjugated triene or tetraene (iii) in (A) is 12 to 33.

12. The unsaturated copolymer of ethylene as claimed in claim 1, wherein the total number of the hydrogen atoms directly bonded to the carbon atoms adjacent to all the carbon-to-carbon double bonds in the nonconjugated triene or tetraene (iii) in (A) is 14 to 33.

13. A rubber composition comprising:

an unsaturated copolymer of ethylene as claimed in claim 1, and at least one component selected from the following agents (a), (b) and (c):
  (a) a reinforcing agent in an amount of not more than 300 parts by weight based on 100 parts by weight of said unsaturated copolymer of ethylene,
  (b) a softening agent in an amount of not more than 200 parts by weight based on 100 parts by weight of said unsaturated copolymer of ethylene, and
  (c) a vulcanizing agent.

* * * * *